United States Patent
Fujii et al.

(10) Patent No.: US 10,525,058 B2
(45) Date of Patent: Jan. 7, 2020

(54) UREA DERIVATIVE OR PHARMACOLOGICALLY ACCEPTABLE SALT THEREOF

(71) Applicant: KYORIN PHARMACEUTICAL CO., LTD., Tokyo (JP)

(72) Inventors: Kiyoshi Fujii, Tochigi (JP); Kentaro Umei, Toyko (JP); Hiroyasu Takahashi, Miyagi (JP); Mitsuhito Shibasaki, Tochigi (JP); Kohei Ohata, Tochigi (JP)

(73) Assignee: KYORIN PHARMACEUTICAL CO., LTD, Tokyo (JP)

( * ) Notice: Subject to any disclaimer, the term of this patent is extended or adjusted under 35 U.S.C. 154(b) by 0 days.

(21) Appl. No.: 15/576,350

(22) PCT Filed: May 26, 2016

(86) PCT No.: PCT/JP2016/002557
§ 371 (c)(1),
(2) Date: Nov. 22, 2017

(87) PCT Pub. No.: WO2016/189876
PCT Pub. Date: Dec. 1, 2016

(65) Prior Publication Data
US 2018/0207153 A1    Jul. 26, 2018

(30) Foreign Application Priority Data

May 27, 2015 (JP) .................................. 2015-107227

(51) Int. Cl.

| | | |
|---|---|---|
| *C07D 307/22* | (2006.01) | |
| *C07D 487/22* | (2006.01) | |
| *A61K 31/4985* | (2006.01) | |
| *C07D 487/04* | (2006.01) | |
| *C07D 263/26* | (2006.01) | |
| *C07D 207/273* | (2006.01) | |
| *C07D 498/04* | (2006.01) | |
| *C07D 211/76* | (2006.01) | |
| *A61K 31/343* | (2006.01) | |
| *A61K 31/381* | (2006.01) | |

(52) U.S. Cl.
CPC ........ *A61K 31/4985* (2013.01); *A61K 31/343* (2013.01); *A61K 31/381* (2013.01); *C07D 207/273* (2013.01); *C07D 211/76* (2013.01); *C07D 263/26* (2013.01); *C07D 307/22* (2013.01); *C07D 487/04* (2013.01); *C07D 498/04* (2013.01)

(58) Field of Classification Search
CPC ........................... C07D 307/22; C07D 487/22
See application file for complete search history.

(56) References Cited

FOREIGN PATENT DOCUMENTS

| WO | 2005/047899 A2 | 5/2005 | |
|---|---|---|---|
| WO | 2009/077954 A1 | 6/2009 | |
| WO | 2009/077990 A1 | 6/2009 | |
| WO | 2010/143158 A1 | 12/2010 | |
| WO | 2011/163502 A1 | 12/2011 | |
| WO | 2012/066488 A2 | 5/2012 | |
| WO | 2012/074785 A1 | 6/2012 | |
| WO | 2012/077049 A1 | 6/2012 | |
| WO | 2012/077051 A1 | 6/2012 | |
| WO | 2012/109544 A1 | 8/2012 | |
| WO | 2012/125305 A1 | 9/2012 | |
| WO | 2013/062947 A1 | 5/2013 | |
| WO | 2013/063214 | 5/2013 | |
| WO | 2013/070600 A1 | 5/2013 | |
| WO | 2013/071203 A1 | 5/2013 | |
| WO | WO 2013063214 * | 5/2013 | ............... A61K 9/66 |
| WO | 2013/171687 A1 | 11/2013 | |
| WO | 2013/171694 A1 | 11/2013 | |

(Continued)

OTHER PUBLICATIONS

Hecht. The Journal of Pharmacology and Experimental Therapeutics, 2009, 328(2), 426-434. (Year: 2009).*
"Syphilis-prevention", http://www.webmd.com/sexual-conditions/tc/syphilis-prevention?print=true, 2007, accessed Apr. 9, 2010. (Year: 2007).*
Tae et al, Airway activation of formyl peptide receptors inhibits Th1 and Th17 cell responses via inhibition of mediator release from immune and inflammatory cells and maturation of dendritic cells. The Journal of Immunology. Feb. 15, 2012;188(4):1799-1808.
Summers et al, Singh N, Peters AM, Chilvers ER. Neutrophil kinetics in health and disease. Trends in immunology. Aug. 1, 2010;31(8):318-324.

(Continued)

*Primary Examiner* — Noble E Jarrell
(74) *Attorney, Agent, or Firm* — BakerHostetler

(57) ABSTRACT

The present invention provides a urea derivative or a pharmacologically acceptable salt thereof that has a formyl peptide receptor like 1 (hereinafter may be abbreviated as FPRL1) agonist effect, a pharmaceutical composition containing the urea derivative or the pharmacologically acceptable salt thereof, and a pharmaceutical use thereof. It has been found that a urea derivative represented by the general formula (I) below or a pharmacologically acceptable salt thereof has a superior FPRL1 agonist effect. Compound (I) or a pharmacologically acceptable salt thereof is highly useful for treatment, prevention, or suppression of inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

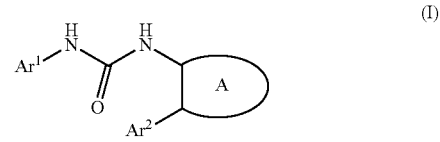

(I)

13 Claims, No Drawings
Specification includes a Sequence Listing.

(56) References Cited

FOREIGN PATENT DOCUMENTS

| WO | 2014/206966 A1 | 12/2014 |
|---|---|---|
| WO | 2015/005305 A1 | 1/2015 |
| WO | 2015/007830 A1 | 1/2015 |
| WO | 2015/009545 A1 | 1/2015 |
| WO | 2015/019325 A1 | 2/2015 |
| WO | 2015/079692 | 6/2015 |
| WO | 2016/095089 | 6/2016 |

OTHER PUBLICATIONS

Sogawa et al, Inhibition of neutrophil migration in mice by mouse formyl peptide receptors 1 and 2 dual agonist: indication of cross-desensitization in vivo. Immunology. Mar. 1, 2011;132(3):441-450.

Schepetkin et al, Gastrin-releasing peptide/neuromedin B receptor antagonists PD176252, PD168368, and related analogs are potent agonists of human formyl-peptide receptors. Molecular pharmacology. Jan. 1, 2011;79(1):77-90.

Nanamori et al, A novel nonpeptide ligand for formyl peptide receptor-like 1. Molecular pharmacology. Nov. 1, 2004;66(5):1213-1222.

Murphy et al, A structural homologue of the N-formyl peptide receptor_ Characterization and chromosome mapping of a peptide chemoattractant receptor family. Journal of Biological Chemistry. Apr. 15, 1992;267(11):7637-7643.

Li et al, The synthetic peptide WKYMVm attenuates the function of the chemokine receptors CCR5 and CXCR4 through activation of formyl peptide receptor-like 1. Blood. May 15, 2001;97(10):2941-2947.

Le Y, Murphy PM, Wang JM. Formyl-peptide receptors revisited. Trends in immunology. Nov. 1, 2002;23(11):541-548.

Krishnamoorthy et al, Resolvin D1 binds human phagocytes with evidence for proresolving receptors. Proceedings of the National Academy of Sciences. Jan. 26, 2010;107(4):1660-1665.

Kirpotina et al, Identification of novel small-molecule agonists for human formyl peptide receptors and pharmacophore models of their recognition. Molecular pharmacology. Jan. 1, 2009:mol-109.

Kim, et al., "PLoS One," vol. 7, No. 1: e30522, 2012.

Kim, et al., "Experimental & Molecular Medicine," 2013, vol. 13, No. 45: e40.

Kim et al, The agonists of formyl peptide receptors prevent development of severe sepsis after microbial infection. The Journal of Immunology. Oct. 1, 2010;185(7):4302-4310.

He et al, Characterization of Quin-C1 for its anti-inflammatory property in a mouse model of bleomycin-induced lung injury. Acta Pharmacologica Sinica. May 2011;32(5):601-610.

Gavins, Are formyl peptide receptors novel targets for therapeutic intervention in ischaemia—reperfusion injury?. Trends in pharmacological sciences. Jun. 1, 2010;31(6):266-276.

Frohn et al, New 'chemical probes' to examine the role of the hFPRL1 (or ALXR) receptor in inflammation. Bioorganic & medicinal chemistry letters. Dec. 1, 2007;17(23):6633-6637.

Dufton et al, Anti-inflammatory role of the murine formyl-peptide receptor 2: ligand-specific effects on leukocyte responses and experimental inflammation. The Journal of Immunology. Mar. 1, 2010;184(5):2611-2619.

Cilibrizzi et al, C. 6-methyl-2, 4-disubstituted pyridazin-3 (2H)-ones: a novel class of small-molecule agonists for formyl peptide receptors. Journal of medicinal chemistry. Jul. 29, 2009;52(16):5044-5057.

Cattaneo et al, Distinct signaling cascades elicited by different formyl peptide receptor 2 (FPR2) agonists. International journal of molecular sciences. Apr. 2, 2013;14(4):7193-7230.

Bürli et al, Potent hFPRL1 (ALXR) agonists as potential anti-inflammatory agents. Bioorganic & medicinal chemistry letters, 16(14), pp. 3713-3718, 2006.

* cited by examiner

SEQUENCE LISTING

<160> NUMBER OF SEQ ID NOS: 6

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      5' primer

<400> SEQUENCE: 1
cgaagcttca ccatggaaac caacttctcc actcctctga atg                          43

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      3' primer

<400> SEQUENCE: 2
cgctcgagtc atattgcctt tatttcaatg tcttcagg                                38

<210> SEQ ID NO 3
<211> LENGTH: 1056
<212> TYPE: DNA
<213> ORGANISM: Homo sapiens

<400> SEQUENCE: 3
atggaaacca acttctccac tcctctgaat gaatatgaag aagtgtccta tgagtctgct        60
ggctacactg ttctgcggat cctcccattg gtggtgcttg ggtcaccttt tgtcctcggg       120
gtcctgggca atgggcttgt gatctgggtg gctggattcc ggatgacacg cacagtcacc       180
accatctgtt acctgaacct ggccctggct gacttttctt tcacggccac attaccattc       240
ctcattgtct ccatggccat gggagaaaaa tggccttttg gctggttcct gtgtaagtta       300
attcacatcg tggtggacat caacctcttt ggaagtgtct tcttgattgg tttcattgca       360
ctggaccgct gcatttgtgt cctgcatcca gtctgggccc agaaccaccg cactgtgagt       420
ctggccatga aggtgatcgt cggaccttgg attcttgctc tagtccttac cttgccagtt       480
ttcctctttt tgactacagt aactattcca aatggggaca catactgtac tttcaacttt       540
gcatcctggg gtggcacccc tgaggagagg ctgaaggtgg ccattaccat gctgacagcc       600
agagggatta tccggtttgt cattggcttt agcttgccga tgtccattgt tgccatctgc       660
tatgggctca ttgcagccaa gatccacaaa aagggcatga ttaaatccag ccgtcccta       720 cgggtcctca ctgctgtggt ggcttctttc ttcatctgtt ggtttccctt tcaactggtt       780
gcccttctgg gcaccgtctg gctcaaagag atgttgttct atggcaagta caaaatcatt       840
gacatcctgg ttaacccaac gagctccctg gccttcttca cagctgcct caaccccatg       900 ctttacgtct ttgtgggcca agacttccga gagagactga tccactccct gcccaccagt       960
ctggagaggg ccctgtctga ggactcagcc ccaactaatg cacggctgc caattctgct      1020 tcacctcctg cagagactga gttacaggca atgtga                                1056

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic

```
                                 5' primer

<400> SEQUENCE: 4
cgaagcttca ccatggcccg ctcgctgac                                    29

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgctcgagtc acagcaggtt gatctcgtcc                                   30

<210> SEQ ID NO 6
<211> LENGTH: 1125
<212> TYPE: DNA
<213> ORGANISM: Homo sapiens

<400> SEQUENCE: 6
atggcccgct cgctgacctg gcgctgctgc ccctggtgcc tgacggagga tgagaaggcc    60
gccgcccggg tggaccagga gatcaacagg atcctcttgg agcagaagaa gcaggaccgc   120
ggggagctga agctgctgct tttgggccca ggcgagagcg ggaagagcac cttcatcaag   180
cagatgcgga tcatccacgg cgccggctac tcggaggagg agcgcaaggg cttccggccc   240
ctggtctacc agaacatctt cgtgtccatg cgggccatga tcgaggccat ggagcggctg   300
cagattccat tcagcaggcc cgagagcaag caccacgcta gcctggtcat gagccaggac   360
ccctataaag tgaccacgtt tgagaagcgc tacgctgcgg ccatgcagtg gctgtggagg   420
gatgccggca tccgggccta ctatgagcgt cggcgggaat tccacctgct cgattcagcc   480
gtgtactacc tgtcccacct ggagcgcatc accgaggagg gctacgtccc acagctcag   540 gacgtgctcc gcagccgcat gcccaccact ggcatcaacg agtactgctt ctccgtgcag   600
aaaaccaacc tgcggatcgt ggacgtcggg ggccagaagt cagagcgtaa gaaatggatc   660
cattgtttcg agaacgtgat cgccctcatc tacctggcct cactgagtga atacgaccag   720
tgcctggagg agaacaacca ggagaaccgc atgaaggaga gcctcgcatt gtttgggact   780
atcctggaac taccctggtt caaaagcaca tccgtcatcc tctttctcaa caaaaccgac   840
atcctggagg agaaaatccc cacctcccac ctggctacct atttccccag tttccagggc   900
cctaagcagg atgctgaggc agccaagagg ttcatcctgg acatgtacac gaggatgtac   960
accgggtgcg tggacggccc cgagggcagc aagaagggcg cacgatcccg acgcctcttc  1020
agccactaca catgtgccac agacacacag aacatccgca aggtcttcaa ggacgtgcgg  1080
gactcggtgc tcgcccgcta cctggacgag atcaacctgc tgtga               1125
```

UREA DERIVATIVE OR PHARMACOLOGICALLY ACCEPTABLE SALT THEREOF

CROSS-REFERENCE TO RELATED APPLICATIONS

This application is the National Stage of International Patent Application No. PCT/JP2016/002557 filed May 26, 2016, which claims priority from Japanese Patent Application No. 2015-107227 filed May 27, 2015, the disclosures of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 2, 2017, is named 082867_000151_SL.txt and is 4,256 bytes in size.

TECHNICAL FIELD

The present invention relates to a urea derivative or a pharmacologically acceptable salt thereof that are useful as pharmaceuticals and have a formyl peptide receptor like 1 (hereinafter may be abbreviated as FPRL1) agonist effect, a pharmaceutical composition containing the urea derivative or the pharmacologically acceptable salt thereof, and a pharmaceutical use thereof.

BACKGROUND ART

FPRL1 (formyl peptide receptor like 1, also known as Lipoxin A4 Receptor, ALXR, and $FPR^2$) is a G protein-coupled receptor cloned as a subtype of N-formyl peptide receptors (FPRs) by Murphy et al. (Non-Patent Literature 1). The FPRL1 was discovered as a receptor that mediates calcium mobilization in response to high concentration of fMLF (formyl methionine leucyl phenylalanine peptide).

Expression of FPRL1 has been found in neutrophils, monocytes, T-lymphocytes, dendritic cells, etc. (Non-Patent Literature 2), but the role of FPRL1 in a living body is complicated and has therefore not been elucidated sufficiently (Non-Patent Literature 3). However, in a paw edema model and an arthritis model using FPRL1 deficient mice, it has been recognized that the reactions become worse (Non-Patent Literature 4). Therefore, it is considered that FPRL1 contributes to the resolution of the inflammation.

Endogenous lipid mediators such as Lipoxin A4 (LXA4) and Resolvin D1 (RvD1) and peptides such as WKYMVm have been reported as agonists that bind to FPRL1 (Non-Patent Literatures 5 and 6).

Such FPRL1 agonists can reduce neutrophil chemotaxis in vitro (Non-Patent Literatures 7 and 8). Although neutrophils perform host defense, they cause vascular injury, result in an increase in vascular permeability and edema, followed by release of chemotactic factors, and thereby contribute to inflammation (Non-Patent Literature 9). Therefore, it is considered that the FPRL1 agonists exhibit an anti-inflammatory effect.

For example, it has been confirmed that peptide agonists exhibit an inhibitory effect on intestinal inflammation (Non-Patent Literature 10), an inhibitory effect on airway inflammation (Non-Patent Literature 11), an inhibitory effect on septicemia (Non-Patent Literature 12), and an inhibitory effect on a cancer model (Non-Patent Literature 13). It has also been recognized that QuinC1, a non-peptide low-molecular weight compound, inhibits bleomycin-induced lung inflammation (Non-Patent Literature 14).

Therefore, FPRL1 can be considered as a target of various diseases such as inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders. Therefore, the FPRL1 agonists can be promising therapeutic agent for these diseases.

Known examples of the non-peptide low-molecular weight compound exhibiting FPRL1 agonist activity include quinazolinones (Non-Patent Literature 15), pyrazolones (Non-Patent Literature 16), benzimidazoles (Non-Patent Literature 17), aminoazoles (Patent Literatures 1, 2, 3, 4, and 5), spiro[2,4]heptanes (Patent Literature 6, 7, 8, 9, and 10), pyridazinones (Non-Patent Literature 18), cycloalkyl and cycloalkenyl-1,2-dicarboxylic acids (Patent Literature 11), dihydronaphthalenes (Patent Literature 12), pyrrolidine-2,5-diones (Patent Literature 13), thiazoles (Patent Literature 14), and urea derivatives (Patent Literatures 15, 16, 17, 18, 19, 20, 21, and 22) (Non-Patent Literatures 19 and 20).

However, the basic chemical structures of these compounds are different from those of the compounds of the present invention. It is obvious that the above compounds are not included in the claims of the present application.

CITATION LIST

Non Patent Literature

[NPL 1] Murphy P. M., et al., "The Journal of Biological Chemistry," 1992, vol. 267, pp. 7637-7643
[NPL 2] Gavins F. N. E, et al., "Trends in Pharmacological Sciences," 2010, vol. 31, pp. 266-276
[NPL 3] Cattaneo F., et al., "International Journal of Molecular Sciences," 2013, vol. 14, No. 4, pp. 7193-7230
[NPL 4] Dufton N, et al., "The Journal of Immunology," 2010, vol. 184, pp. 2611-2619
[NPL 5] Le Y, et al., "Trends in immunology," 2002, vol. 23, No. 11, pp. 541-548
[NPL 6] Krishnamoorthy S, "Proceedings of the National Academy of Sciences," 2010, vol. 107, No. 4, pp. 1660-1665
[NPL 7] Li B. Q, et al., "Blood," 2001, vol. 97, pp. 2941-2947
[NPL 8] Sogawa Y, et al., "Immunology," 2011, vol. 132, pp. 441-450
[NPL 9] Summers C, et al., "Trends in Immunology," 2010, vol. 31, pp. 318-324
[NPL 10] Kim S. D, et al., "Experimental & Molecular Medicine," 2013, vol. 13, No. 45: e40.
[NPL 11] Tae Y. M, et al., "The Journal of Immunology," 2012, vol. 188, pp. 1799-1808
[NPL 12] Kim S. D, et al., "The Journal of Immunology," 2010, vol. 185, pp. 4302-4310
[NPL 13] Kim S. D, et al., "PLoS ONE," vol. 7, No. 1: e30522.
[NPL 14] Min H. E, et al., "Acta Pharmacologica Sinica" 2011, vol. 32, pp. 601-610
[NPL 15] Nanamori M, et al., "Molecular Pharmacology," 2004, vol. 66, pp. 1213-1222
[NPL 16] Burli R. W, et al., "Bioorganic & Medicinal Chemistry Letters," 2006, vol. 16, pp. 3713-3718
[NPL 17] Frohn M, et al., "Bioorganic & Medicinal Chemistry Letters," 2007, vol. 17, pp. 6633-6637

[NPL 18] Cilibrizzi A, et al., "Journal of Medicinal Chemistry," 2009, vol. 52, pp. 5044-5057
[NPL 19] Kirpotina L. N, et al., "Molecular Pharmacology," 2010, vol. 77, pp. 159-170
[NPL 20] Schepetkin I. A, et al., "Molecular Pharmacology," 2011, vol. 79, pp. 77-90

Patent Literature

[PL 1] WO2009/077990
[PL 2] WO2009/077954
[PL 3] WO2010/143158
[PL 4] WO2012/077049
[PL 5] WO2012/077051
[PL 6] WO2012/066488
[PL 7] WO2013/171687
[PL 8] WO2013/171694
[PL 9] WO2014/206966
[PL 10] WO2015/007830
[PL 11] WO2011/163502
[PL 12] WO2012/125305
[PL 13] US130018067
[PL 14] WO 2015/005305
[PL 15] WO2005/047899
[PL 16] WO2012/074785
[PL 17] WO2012/109544
[PL 18] WO2013/062947
[PL 19] WO2013/070600
[PL 20] WO2013/071203
[PL 21] WO2015/009545
[PL 22] WO2015/019325

SUMMARY OF INVENTION

Technical Problem

At present, no compound has been found which has a superior FPRL1 agonist effect as a prophylactic or therapeutic agent for various disease states described above and can be used as a sufficiently satisfactory pharmaceutical.

It is an object of the present invention to provide a compound having an FPRL1 agonist effect.

Solution to Problem

The present inventors have conducted extensive studies and found that a urea compound represented by the general formula (I) below (this compound may be referred to as a compound (I)) or a pharmacologically acceptable salt thereof has a superior FPRL1 agonist effect and is sufficiently satisfactory as a pharmaceutical, and thus the present invention has been completed.

Accordingly, the present invention is as follows.

[1] A compound represented by the general formula (I) or a pharmacologically acceptable salt thereof:

[Chem.1]

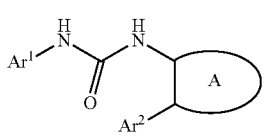

(I)

wherein, in the formula (I), $Ar^1$ is a phenyl group optionally having substituent(S), a monocyclic aromatic heterocyclyl group optionally having substituent(S), or a bicyclic aromatic heterocyclyl group having 9 or 10 atoms and optionally having substituent(s);

$Ar^2$ is a phenyl group optionally having substituent(S) (provided that when A is A1, the phenyl group whose substituent(s) is only halogen atom(s) is excluded), a monocyclic aromatic heterocyclyl group optionally having substituent(S), or a bicyclic aromatic heterocyclyl group having 9 or 10 atoms and optionally having substituent(s);

A is a group selected from the group consisting of the following A1), A2), A3), A4), and A5):

[Chem.2]

A1)

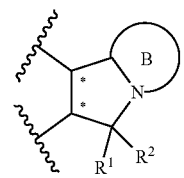

A2)

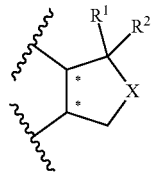

A3)

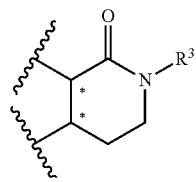

A4)

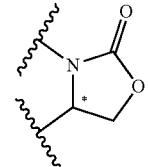

A5)

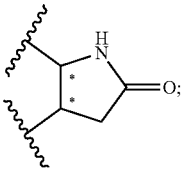

wherein $R^1$ and $R^2$ are independently a hydrogen atom or a $C_1$ to $C_6$ alkyl group optionally having substituent(S), or $R^1$ and $R^2$ together form a $C_2$ to $C_6$ alkylene group;

$R^3$ is a hydrogen atom or a $C_1$ to $C_6$ alkyl group optionally having substituent(S);

X is an oxygen atom, a sulfur atom, or $SO_2$;

B is a heterocyclyl group optionally having substituent (S); and each carbon atom marked with an asterisk is an asymmetric carbon atom.

[2] The compound according to [1] or a pharmacologically acceptable salt thereof,
wherein
in the formula (I), A is a group selected from the group consisting of the following A1a), A1b), and A1c):

[Chem.3]

A1a)

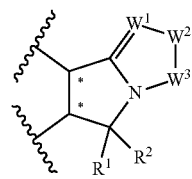

A1b)

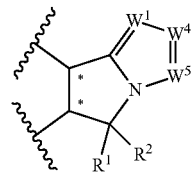

A1c)

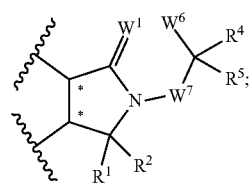

wherein W¹ is C—R⁶ or a nitrogen atom;
W² is CR⁷R⁸ or N—R⁹;
W³ is CR¹⁰R¹¹ or C=O;
W⁴ is C—R¹² or a nitrogen atom;
W⁵ is C—R¹³ or a nitrogen atom;
W⁶ is CR¹⁴R¹⁵, an oxygen atom, or C=O;
W⁷ is CR¹⁶R¹⁷ or C=O;
R⁴, R⁵, R⁷, R⁸, R¹⁰, R¹¹, R¹⁴, R¹⁵, R¹⁶, and R¹⁷ are independently a hydrogen atom or a $C_1$ to $C_6$ alkyl group optionally having substituent(S), or R⁴ and R⁵, R⁷ and R⁸, R¹⁰ and R¹¹, R¹⁴ and R¹⁵, or R¹⁶ and R¹⁷ may together form a $C_3$ to $C_6$ cycloalkyl group or a 3- to 10-membered heterocycloalkyl group; and
R⁶, R⁹, R¹², and R¹³ are independently a hydrogen atom, a halogen atom, a cyano group, a hydroxy group, a $C_1$ to $C_6$ alkyl group optionally having substituent(S), a $C_1$ to $C_6$ alkoxy group optionally having substituent(S), a $C_1$ to $C_6$ alkoxycarbonyl group optionally having substituent(S), a $C_1$ to $C_6$ acyl group optionally having substituent(S), a $C_1$ to $C_6$ alkylsulfanyl group optionally having substituent(S), a $C_1$ to $C_6$ alkylsulfinyl group optionally having substituent(S), a $C_1$ to $C_6$ alkylsulfonyl group optionally having substituent(S), a heterocyclyl group optionally having substituent(S), —CONR¹⁸R¹⁹, or —NR¹⁸R¹⁹, wherein when R⁶, R⁹, R¹², and/or R¹³ are —CONR¹⁸R¹⁹ or —NR¹⁸R¹⁹, R¹⁸ is a hydrogen atom, a $C_1$ to $C_6$ alkyl group optionally having substituent(S), a $C_1$ to $C_6$ acyl group optionally having substituent (S), or a $C_1$ to $C_6$ alkylsulfonyl group optionally having substituent(S), and R¹⁹ is a hydrogen atom or a $C_1$ to $C_6$ alkyl group optionally having substituent(S), or R¹⁸ and R¹⁹ together form 3- to 10-membered heterocycloalkyl group.

[3] The compound according to [1] or [2] or a pharmacologically acceptable salt thereof, wherein
in the formula (I), A is a group selected from the group consisting of the following A1ba), A1bb), A1bc), A1ca), A1cb), A1cc), A1cd), A2), A3), A4), and A5):

[Chem.4]

A1ba)

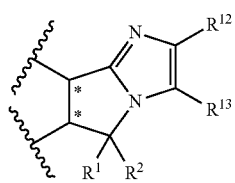

A1bb)

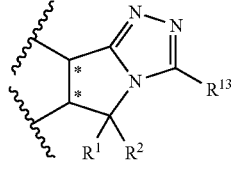

A1bc)

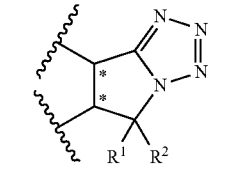

A1ca)

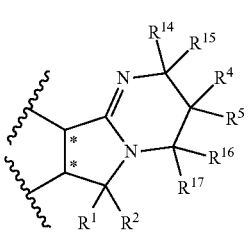

A1cb)

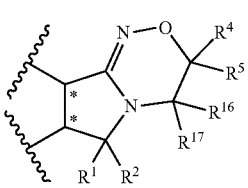

A1cc)

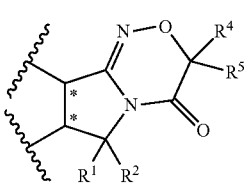

-continued

A1cd)

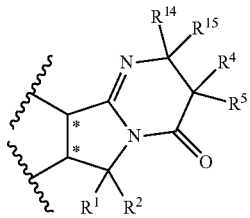

A2)

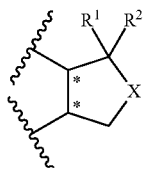

A3)

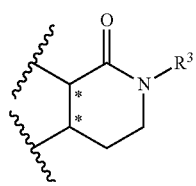

A4)

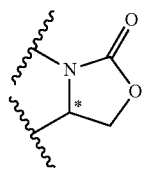

A5)

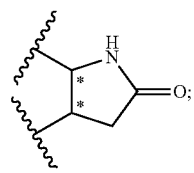

wherein $R^1$ and $R^2$ are independently a hydrogen atom or a $C_1$ to $C_3$ alkyl group;

$R^3$ is a hydrogen atom or a $C_1$ to $C_3$ alkyl group;

$R^4$, $R^5$, $R^{14}$, $R^{15}$, $R^{16}$, and $R^{17}$ are independently a hydrogen atom or a $C_1$ to $C_6$ alkyl group, or $R^4$ and $R^5$, $R^{14}$ and $R^{15}$, or $R^{16}$ and $R^{17}$ may together form a $C_3$ to $C_6$ cycloalkyl group or a 3- to 10-membered heterocycloalkyl group;

$R^{12}$ and $R^{13}$ are independently a hydrogen atom, a halogen atom, a cyano group, a hydroxy group, a $C_1$ to $C_3$ alkyl group, a $C_1$ to $C_6$ alkoxy group, a $C_1$ to $C_6$ alkoxy-carbonyl group, a $C_1$ to $C_6$ acyl group, a $C_1$ to $C_6$ alkylsulfanyl group, a $C_1$ to $C_6$ alkyl-sulfinyl group, a $C_1$ to $C_6$ alkylsulfonyl group, —$CONR^{18}R^{19}$, or —$NR^{18}R^{19}$, wherein when $R^{12}$ and/or $R^{13}$ are —$CONR^{18}R^{19}$ or —$NR^{18}R^{19}$, $R^{18}$ is a hydrogen atom, a $C_1$ to $C_6$ alkyl group, a $C_1$ to $C_6$ acyl group, or a $C_1$ to $C_6$ alkylsulfonyl group, and $R^{19}$ is a hydrogen atom or a $C_1$ to $C_6$ alkyl group, or $R^{18}$ and $R^{19}$ together form 3- to 10-membered heterocycloalkyl group; and X is an oxygen atom or $SO_2$.

[4] The urea compound according to any one of [1] to [3] or a pharmacologically acceptable salt thereof, wherein in the formula (I), $Ar^2$ is a group selected from the group consisting of the following B1), B2), B3), and B4):

[Chem.5]

B1)

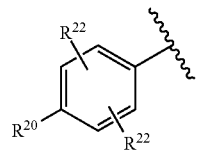

B2)

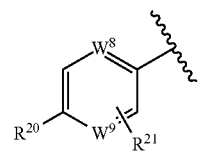

B3)

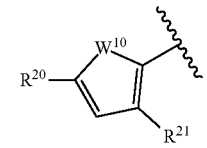

B4)

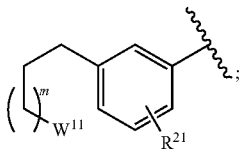

wherein one of $W^8$ and $W^9$ is a nitrogen atom, and the other one is CH or a nitrogen atom;

$W^{10}$ is an oxygen atom, a sulfur atom, or N—$R^{22}$;

$W^{11}$ is C=O, $CH_2$, $CF_2$, CHOH, N—$R^{23}$, an oxygen atom, or a sulfur atom;

$R^{20}$ is a hydrogen atom, a halogen atom, a hydroxy group, a cyano group, a $C_1$ to $C_6$ alkyl group optionally having substituent(S), a $C_1$ to $C_6$ alkoxy group optionally having substituent(S), a halo-$C_1$ to $C_6$ alkoxy group having substituent(S), a $C_1$ to $C_6$ acyl group optionally having substituent(S), a $C_1$ to $C_6$ alkylsulfanyl group optionally having substituent(S), a $C_1$ to $C_6$ alkylsulfinyl group optionally having substituent(S), a $C_1$ to $C_6$ alkylsulfonyl group optionally having substituent(S), a heterocyclyl group optionally having substituent(S), —$CONR^{18}R^{19}$, or —$NR^{18}R^{19}$, wherein when $R^{20}$ is —$CONR^{18}R^{19}$ or —$NR^{18}R^{19}$, $R^{18}$ is a hydrogen atom, a $C_1$ to $C_6$ alkyl group optionally having substituent(S), a $C_1$ to $C_6$ acyl group optionally having substituent(S), or a $C_1$ to $C_6$ alkyl-sulfonyl group optionally having substituent(S), and $R^{19}$ is a hydrogen atom or a $C_1$ to $C_6$ alkyl group optionally having substituent(S), or $R^{18}$ and $R^{19}$ together form 3- to 10-membered heterocycloalkyl group;

$R^{21}$ is a hydrogen atom, a halogen atom, a hydroxy group, a cyano group, a $C_1$ to $C_6$ alkyl group optionally having substituent(S), or a $C_1$ to $C_6$ alkoxy group optionally having substituent(S);

$R^{22}$ is a hydrogen atom, a halogen atom, or a $C_1$ to $C_6$ alkyl group optionally having substituent(S);

m is 0 or 1; and provided that when $Ar^2$ is B1), $R^{20}$, $R^{21}$, and $R^{22}$ are not a combination of a hydrogen atom and a halogen atom.

[5] The compound according to any one of [1] to [4] or a pharmacologically acceptable salt thereof, wherein in the formula (I), $Ar^1$ is a group selected from the group consisting of the following C1), C2), C3), and C4):

[Chem.6]

C1) 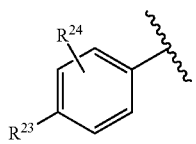

C2) 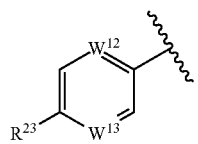

C3) 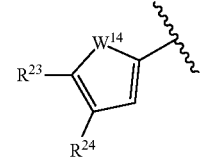

C4) 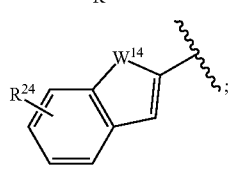

wherein one of $W^{12}$ and $W^{13}$ is a nitrogen atom, and the other one is CH or a nitrogen atom;

$W^{14}$ is an oxygen atom, a sulfur atom or $N-R^{22}$;

$R^{23}$ is a hydrogen atom, a halogen atom, a cyano group, a $C_1$ to $C_6$ alkyl group optionally having substituent(S), a $C_1$ to $C_6$ alkoxy group optionally having substituent(S), a $C_3$ to $C_6$ cycloalkyl group optionally having substituent(S), a $C_1$ to $C_6$ acyl group optionally having substituent(S), a $C_2$ to $C_6$ alkenyl group optionally having substituent(S), a $C_2$ to $C_6$ alkynyl group optionally having substituent(S), a $C_1$ to $C_6$ alkoxycarbonyl group optionally having substituent(S), a $C_1$ to $C_6$ alkylsulfanyl group optionally having substituent(S), a $C_1$ to $C_6$ alkylsulfinyl group optionally having substituent (S), a $C_1$ to $C_6$ alkylsulfonyl group optionally having substituent(S), an aryloxy group optionally having substituent (S), a heterocyclyl group optionally having substituent(S), $-CONR^{18}R^{19}$, or $-NR^{18}R^{19}$, wherein when $R^{23}$ is $-CONR^{18}R^{19}$ or $-NR^{18}R^{19}$, $R^{18}$ is a hydrogen atom, a $C_1$ to $C_6$ alkyl group optionally having substituent(S), a $C_1$ to $C_6$ acyl group optionally having substituent(S), or a $C_1$ to $C_6$ alkylsulfonyl group optionally having substituent(S), and $R^{19}$ is a hydrogen atom or a $C_1$ to $C_6$ alkyl group optionally having substituent(S), or $R^{18}$ and $R^{19}$ together form 3- to 10-membered hetero-cycloalkyl group; and $R^{24}$ is a hydrogen atom, a halogen atom, a hydroxy group, or a $C_1$ to $C_6$ alkyl group.

[6] The urea compound according to any one of [1] to [5] or a pharmacologically acceptable salt thereof, wherein in the formula (I), $Ar^2$ is a group selected from the group consisting of the following B1a), B3a), and B4a):

[Chem.7]

B1a) 

B3a) 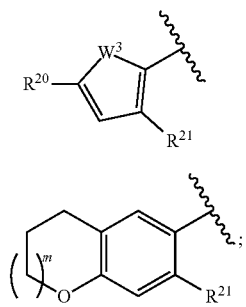

B4a) 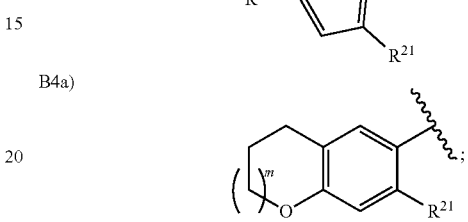

wherein $R^{20}$ is a fluorine atom, a chlorine atom, a cyano group, a $C_1$ to $C_6$ alkyl group, a $C_1$ to $C_6$ alkoxy group, a halo-$C_1$ to $C_6$ alkoxy group, a $C_1$ to $C_6$ alkylsulfanyl group, a $C_1$ to $C_6$ alkylsulfinyl group, $-CONR^{18}R^{19}$, or $-NR^{18}R^{19}$, wherein when $R^{20}$ is $-CONR^{18}R^{19}$ or $-NR^{18}R^{19}$, $R^{18}$ is a hydrogen atom, a $C_1$ to $C_6$ alkyl group, a $C_1$ to $C_6$ acyl group, or a $C_1$ to $C_6$ alkylsulfonyl group, and $R^{19}$ is a hydrogen atom or a $C_1$ to $C_6$ alkyl group, or $R^{18}$ and $R^{19}$ together form 3- to 10-membered heterocycloalkyl group;

$R^{21}$ is a hydrogen atom or a halogen atom;

$R^{22}$ is a hydrogen atom or a halogen atom;

m is 0 or 1; and provided that when $Ar^2$ is B1a), $R^{20}$, $R^{21}$, and $R^{22}$ are not a combination of a hydrogen atom and a halogen atom.

[7] The compound according to any one of [1] to [6] or a pharmacologically acceptable salt thereof, wherein in the formula (I), $Ar^1$ is C1):

[Chem.8]

C1) 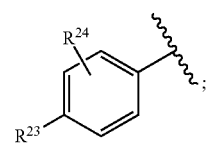

wherein $R^{23}$ is a hydrogen atom, a halogen atom, a cyano group, a trifluoromethyl group, or a $C_1$ to $C_3$ alkyl group; and $R^{24}$ is a hydrogen atom, a halogen atom, or a hydroxy group.

[8] The urea compound according to any one of [1] to [7] or a pharmacologically acceptable salt thereof, wherein in the formula (I), Ar² is B1aa):

[Chem.9]
B1aa)

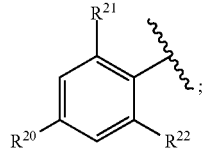

wherein $R^{20}$ is a cyano group, an ethyl group, or a $C_1$ to $C_3$ alkoxy group;
$R^{21}$ is a hydrogen atom, a fluorine atom, or a chlorine atom; and
$R^{22}$ is a hydrogen atom, a fluorine atom, or a chlorine atom.

[9] The compound according to [1] or a pharmacologically acceptable salt thereof, wherein
the compound represented by the formula (I) is
(±)-cis-1-(4-chlorophenyl)-3-[4-(4-methoxyphenyl)-tetrahydrofuran-3-yl]urea,
(±)-cis-1-(3-fluorophenyl)-3-[4-(4-methoxyphenyl)-tetrahydrofuran-3-yl]urea,
(±)-cis-1-(2-fluorophenyl)-3-[4-(4-methoxyphenyl)-tetrahydrofuran-3-yl]urea,
(±)-cis-1-(2,4-difluorophenyl)-3-[4-(4-methoxyphenyl)-tetrahydrofuran-3-yl]urea,
(±)-cis-1-(3,4-difluorophenyl)-3-[4-(4-methoxyphenyl)-tetrahydrofuran-3-yl]urea,
(±)-cis-1-(4-cyanophenyl)-3-[4-(4-methoxyphenyl)-tetrahydrofuran-3-yl]urea,
(±)-cis-1-(5-chlorothiophen-2-yl)-3-[4-(4-methoxy-phenyl)tetrahydrofuran-3-yl]urea,
(±)-cis-1-[4-(2,6-difluoro-4-methoxyphenyl)tetrahydrofuran-3-yl]-3-(4-fluorophenyl) urea,
(±)-trans-1-(4-chlorophenyl)-3-[4-(4-methoxyphenyl)tetrahydrofuran-3-yl]urea,
(±)-1-(4-chlorophenyl)-3-[4-(4-methoxyphenyl)-1,1-dioxidotetrahydrothiophen-3-yl] urea,
(±)-trans-1-(4-chlorophenyl)-3-[4-(4-methoxyphenyl)-2-oxopiperidin-3-yl]urea,
(+)-cis-1-(4-chlorophenyl)-3-[4-(4-methoxyphenyl)tetrahydrofuran-3-yl]urea,
(+)-cis-1-(4-fluorophenyl)-3-[4-(4-methoxyphenyl)tetrahydrofuran-3-yl]urea,
(+)-cis-1-(4-fluorophenyl)3-[4-(4-methoxyphenyl)-2,2-dimethyltetrahydrofuran-3-yl] urea,
(±)-cis-1-[4-(4-chlorophenyl)tetrahydrofuran-3-yl]-3-(4-fluorophenyl)urea,
(±)-cis-1-[4-(4-fluorophenyl)tetrahydrofuran-3-yl]-3-(4-fluorophenyl)urea,
(±)-cis-1-[4-(4-cyanophenyl)tetrahydrofuran-3-yl]-3-(4-fluorophenyl)urea,
(±)-1-(4-chlorophenyl)-3-[4-(4-methoxyphenyl)-2-oxoxazolidin-3-yl]urea,
(±)-trans-1-(4-fluorophenyl)-3-[3-(4-methoxyphenyl)-5-oxopyrrolidin-2-yl]urea,
(−)-1-[(6R*,7S*)-6-(2,6-difluoro-4-methoxyphenyl)-3-methyl-6,7-dihydro-5H-pyrrolo[2,1-c][1,2,4]triazol-7-yl]-3-(4-fluorophenyl)urea,
(−)-1-[(6R*,7S*)-6-(2,6-difluoro-4-methoxyphenyl)-6,7-dihydro-5H-pyrrolo[1,2-a]imidazol-7-yl]-3-(4-fluorophenyl)urea,
(−)-1-(4-fluorophenyl)-3-[(6R*,7S*)-6-(4-methoxyphenyl)-6,7-dihydro-5H-pyrrolo[1,2-d]tetrazol-7-yl]urea,
(−)-1-[(6R*,7S*)-6-(2,6-difluoro-4-methoxyphenyl)-6,7-dihydro-5H-pyrrolo[1,2-d]tetrazol-7-yl]-3-(4-fluorophenyl)urea,
(−)-1-[(6R*,7S*)-6-(6-fluoro-2,3-dihydrobenzofuran-5-yl)-6,7-dihydro-5H-pyrrolo[1,2-d]tetrazol-7-yl]-3-(4-fluorophenyl)urea,
(−)-1-[(7R*,8S*)-7-(2,6-difluoro-4-methoxyphenyl)-2,3,4,6,7,8-hexahydropyrrolo[1,2-a]pyrimidin-8-yl]-3-(4-fluorophenyl)urea,
1-[(7R*,8S*)-7-(2,6-difluoro-4-methoxyphenyl)-4,6,7,8-tetrahydro-3H-pyrrolo[2,1-c][1,2,4]oxadiazin-8-yl]-3-(4-fluorophenyl)urea,
(−)-1-[(7R*,8S*)-7-(2,6-difluoro-4-methoxyphenyl)-4-oxo-4,6,7,8-tetrahydro-3H-pyrrolo[2,1-c][1,2,4]oxadiazin-8-yl]-3-(4-fluorophenyl)urea,
(−)-1-[(7R*,8S*)-7-(2,6-difluoro-4-methoxyphenyl)-4-oxo-2,3,4,6,7,8-hexahydropyrrolo[1,2-a]pyrimidin-8-yl]-3-(4-fluorophenyl)urea, or
1-(4-fluorophenyl)-3-[(7R*,8S*)-7-(4-methoxyphenyl)-4-oxo-4,6,7,8-tetrahydro-3H-pyrrolo[2,1-c] [1,2,4]oxadiazin-8-yl]urea.

[10] A pharmaceutical comprising, as an active ingredient, the compound according to any one of [1] to [9] or a pharmacologically acceptable salt thereof.

[11] An FPRL1 agonist comprising, as an active ingredient, the compound according to any one of [1] to [9] or a pharmacologically acceptable salt thereof.

[12] A method of treatment or prevention of inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders, comprising administering the compound according to any one of [1] to [9] or a pharmacologically acceptable salt thereof.

[13] Use of the compound according to any one of [1] to [9] or a pharmacologically acceptable salt thereof to produce a pharmaceutical for treatment or prevention of inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders.

[14] A pharmaceutical composition containing the compound according to any one of [1] to [9] or a pharmacologically acceptable salt thereof and a pharmaceutically acceptable carrier, used for prevention or treatment of inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders.

Advantageous Effects of Invention

The compound (I) or a pharmacologically acceptable salt thereof exhibited superior agonist activity in, for example, a test of calcium influx into FPRL1-overexpressing cells. The compound (I) and salts thereof strongly suppressed lipopolysaccharide-induced neutrophilic infiltration into the lungs of mice. In addition, the compound (I) and salts thereof have low toxicity and are therefore safe. Therefore, the compound (I) according to the present invention or a pharmacologically acceptable salt thereof is useful as a therapeutic or prophylactic agent for inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

In addition, the compound (I) according to the present invention or a pharmacologically acceptable salt thereof is highly useful for treatment, prevention, or suppression of various disease states associated with the FPRL1 (such as Behcet's disease, Sweet disease, systemic lupus erythematosus (SLE), Wegener's granulomatosis, virus infection, diabetes, amputations, cancers, bacterial infection, physical external injuries, physical disorders including exposure to radiation, vasoconstriction, anaphylactic reactions, allergic reactions, rhinitis, shocks (endotoxic, hemorrhagic, traumatic, splanchnic ischemia, and circulatory shocks), rheumatoid arthritis, gout, psoriasis, benign prostatic hyperplasia, myocardial ischemia, myocardial infarction, brain injuries, pulmonary diseases, COPD, COAD, COLD, acute lung injury, acute respiratory distress syndrome, chronic bronchitis, pulmonary emphysema, asthma (allergic asthma and non-allergic asthma), cystic pulmonary fibrosis, nephropathy, renal glomerular diseases, ulcerative colitis, IBD, Crohn's disease, periodontitis, pains, Alzheimer's disease, AIDS, uveitic glaucoma, conjunctivitis, Sjoegren's syndrome, and rhinitis).

Description of Embodiments

Terms in the present description will be described.

The term "halogen atom" as used herein means a fluorine atom, a chlorine atom, a bromine atom, or an iodine atom. Preferably, the halogen atom is a fluorine atom or a chlorine atom.

The monocyclic aromatic heterocyclyl group in the term "monocyclic aromatic heterocyclyl group optionally having substituent(s)" as used herein means a 5- or 6-membered aromatic heterocyclyl group containing, in its ring, 1 to 4 atoms selected from sulfur, oxygen, and nitrogen atoms. Examples of the monocyclic aromatic heterocyclyl group may include a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyridyl group, a pyridazinyl group, a pyrimidinyl group, a pyrazinyl group and the like.

The bicyclic aromatic heterocyclyl group having 9 or 10 atoms in the term "bicyclic aromatic heterocyclyl group having 9 or 10 atoms and optionally having substituent(s)" as used herein means a bicyclic aromatic heterocyclyl group having 9 or 10 atoms containing 1 to 4 atoms selected from sulfur, oxygen, and nitrogen atoms. Examples of the bicyclic aromatic heterocyclyl group having 9 or 10 atoms may include a benzofuranyl group, an isobenzofuranyl group, a benzoxazolyl group, a benzisoxazolyl group, a benzothiazolyl group, a benzisothiazolyl group, a benzimidazolyl group, a benzothiophenyl group, an indolyl group, an isoindolyl group, an indazolyl group, a thiazolopyridyl group, an oxazolopyrazinyl group, a purinyl group, a quinolizinyl group, an isoquinolyl group, a quinolyl group, a phthalazinyl group, a naphthyridinyl group, a quinoxalinyl group, a quinazolinyl group and the like.

The $C_1$ to $C_6$ alkoxy group in the terms "$C_1$ to $C_6$ alkoxy group optionally having substituent(s)" and "$C_1$ to $C_6$ alkoxy group" as used herein means a linear or branched alkoxy group having 1 to 6 carbon atoms. Examples of the $C_1$ to $C_6$ alkoxy group may include a methoxy group, an ethoxy group, a propoxy group, an isopropoxy group, an isobutoxy group, a butoxy group, a sec-butoxy group, a tert-butoxy group, a pentyloxy group, a hexyloxy group and the like. Preferred examples may include a methoxy group and an ethoxy group.

The $C_1$ to $C_6$ alkyl group in the terms "$C_1$ to $C_6$ alkyl group optionally having substituent(s)" and "$C_1$ to $C_6$ alkyl group" as used herein means a linear or branched alkyl group having 1 to 6 carbon atoms and optionally having substituent(s). Examples of the $C_1$ to $C_6$ alkyl group may include a methyl group, an ethyl group, a propyl group, an isopropyl group, a butyl group, an isobutyl group, a sec-butyl group, a tert-butyl group, a pentyl group, an isopentyl group, a neopentyl group, a 1-methylbutyl group, a 2-methylbutyl group, a 1,2-dimethylpropyl group, a hexyl group, an isohexyl group and the like.

The $C_1$ to $C_6$ acyl group in the terms "$C_1$ to $C_6$ acyl group optionally having substituent(s)" and "$C_1$ to $C_6$ acyl group" as used herein means an acyl group derived from a linear or branched aliphatic carboxylic acid having 1 to 6 carbon atoms. Examples of the $C_1$ to $C_6$ acyl group may include a formyl group, an acetyl group, a propanoyl group, a butanoyl group, a pentanoyl group, a hexanoyl group and the like.

The $C_1$ to $C_6$ alkylsulfanyl group in the terms "$C_1$ to $C_6$ alkylsulfanyl group optionally having substituent(s)" and "$C_1$ to $C_6$ alkylsulfanyl group" as used herein means a linear or branched alkylsulfanyl group having 1 to 6 carbon atoms or a cyclic alkylsulfanyl group having 3 to 6 carbon atoms. Examples of the $C_1$ to $C_6$ alkylsulfanyl group may include a methylsulfanyl group, an ethylsulfanyl group, a propylsulfanyl group, an isopropylsulfanyl group, a butylsulfanyl group, an isobutylsulfanyl group, a secbutylsulfanyl group, a tert-butylsulfanyl group, a cyclopropylsulfanyl group, a cyclobutylsulfanyl group, a cyclopentylsulfanyl group and the like.

The $C_1$ to $C_6$ alkylsulfinyl group in the terms "$C_1$ to $C_6$ alkylsulfinyl group optionally having substituent(s)" and "$C_1$ to $C_6$ alkylsulfinyl group" as used herein means a linear or branched alkylsulfinyl group having 1 to 6 carbon atoms or a cyclic alkylsulfinyl group having 3 to 6 carbon atoms. Examples of the $C_1$ to $C_6$ alkylsulfinyl group may include a methylsulfinyl group, an ethylsulfinyl group, a propylsulfinyl group, an isopropylsulfinyl group, a butylsulfinyl group, an isobutylsulfinyl group, a secbutylsulfinyl group, a tert-butylsulfinyl group, a cyclopropylsulfinyl group, a cyclobutylsulfinyl group, a cyclopentylsulfinyl group and the like.

The $C_1$ to $C_6$ alkylsulfonyl group in the terms "$C_1$ to $C_6$ alkylsulfonyl group optionally having substituent(s)" and "$C_1$ to $C_6$ alkylsulfonyl group" as used herein means a linear or branched alkylsulfonyl group having 1 to 6 carbon atoms or a cyclic alkylsulfonyl group having 3 to 6 carbon atoms. Examples of the $C_1$ to $C_6$ alkylsulfonyl group may include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a cyclopropylsulfonyl group, a cyclobutylsulfonyl group, a cyclopentylsulfonyl group and the like.

The heterocycle in the term "heterocycle optionally having substituent(s)" as used herein means a 5- to 7-membered heterocycle containing 1 to 4 atoms selected from sulfur, oxygen, and nitrogen atoms. Examples of the heterocycle may include: aromatic heterocycles such as a furan ring, a thiophene ring, a pyrrole ring, an azepine ring, a pyrazole ring, an imidazole ring, an oxazole ring, an isoxazole ring, a thiazol ring, an isothiazol ring, a 1,2,3-oxadiazole ring, a triazole ring, a tetrazole ring, a thiadiazole ring, a pyran ring, a pyridine ring, a pyridazine ring, a pyrimidine ring, and a pyrazine ring; unsaturated heterocycles such as a pyrroline ring, an imidazoline ring, a pyrazoline ring, a dihydropyran ring, a dihydrothiopyran ring, and a dihydropyridine; and saturated heterocycles such as a morpholine ring, a thiomorpholine ring, a pyrrolidine ring, an imidazolidine ring, a pyrazolidine ring, a piperidine ring, a piperazine ring, a tetrahydrofuran ring and the like.

The above "heterocycle" may be condensed with another cyclic group. Examples of the heterocycle condensed with another cyclic group may include an isobenzofuran ring, a benzoxazole ring, a benzisoxazole ring, a benzothiazole ring, a benzisothiazole ring, a benzofuran ring, a xanthene ring, a phenoxathiin ring, an indolizine ring, an isoindolizine ring, an indole ring, an indazole ring, a purine ring, a quinolizine ring, an isoquinoline ring, a quinoline ring, a phthalazine ring, a naphthyridine ring, a quinoxaline ring, a quinazoline ring, a carbazole ring, a carboline ring, an acridine ring and the like.

The heterocyclyl group in the term "heterocyclyl group optionally having substituent(s)" as used herein means a 5- to 7-membered heterocyclyl group containing 1 to 4 atoms selected from sulfur, oxygen, and nitrogen atoms. Examples of the heterocyclyl group may include: aromatic heterocyclyl groups such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyridyl group, a pyridazinyl group, a pyrimidinyl group, and a pyrazinyl group; unsaturated heterocyclyl groups such as a pyrrolinyl group, an imidazolinyl group, a pyrazolinyl group, a dihydropyranyl group, a dihydrothiopyranyl group, and a dihydropyridyl group; and saturated heterocyclyl groups such as a morpholinyl group, a thiomorpholinyl group, a pyrrolidinyl group, an imidazolidinyl group, an imidazolinyl group, a pyrazolidinyl group, a pyrazolinyl group, a piperidinyl group, a piperazinyl group, a tetrahydrofuranyl group and the like.

The above "heterocyclyl group" may be condensed with another cyclic group. Examples of the heterocyclyl group condensed with another cyclic group may include an isobenzofuranyl group, a benzoxazolyl group, a benzisoxazolyl group, a benzothiazolyl group, a benzisothiazolyl group, a chromenyl group, a chromanonyl group, a xanthenyl group, a phenoxathiinyl group, an indolizinyl group, an isoindolizinyl group, an indolyl group, an indazolyl group, a purinyl group, a quinolizinyl group, an isoquinolyl group, a quinolyl group, a phthalazinyl group, a naphthyridinyl group, a quinoxalinyl group, a quinazolinyl group, a carbazolyl group, a carbolinyl group, an acridinyl group, an isoindolinyl group and the like.

The term "3- to 10-membered heterocycloalkyl group" as used herein means a monocyclic, bicyclic, or tricyclic non-aromatic heterocycloalkyl group which is a 3- to 10-membered heterocycloalkyl group containing at least one nitrogen atom, oxygen atom, or sulfur atom. Examples of the 3- to 10-membered heterocycloalkyl group may include an azetidinyl group, a pyrrolidinyl group, a piperidyl group, a piperazinyl group, a morpholinyl group and the like.

The $C_3$ to $C_6$ cycloalkyl group in the terms "$C_3$ to $C_6$ cycloalkyl group optionally having substituent(s)" and "$C_3$ to $C_6$ cycloalkyl group" as used herein means a monocyclic saturated alicyclic hydrocarbon group having 3 to 6 carbon atoms. Examples of the $C_3$ to $C_6$ cycloalkyl group may include a cyclopropyl group, a cyclobutyl group, a cyclopentyl group, a cyclohexyl group and the like.

The $C_2$ to $C_6$ alkenyl group in the terms "$C_2$ to $C_6$ alkenyl group optionally having substituent(s)" and "$C_2$ to $C_6$ alkenyl group" as used herein means a linear or branched unsaturated hydrocarbon group having 2 to 6 carbon atoms and having at least one double bond. Examples of the $C_2$ to $C_6$ alkenyl group may include a vinyl group, a 2-propenyl group, a 1-propenyl group, a 3-propenyl group, a 1-buten-1-yl group, a 1-buten-2-yl group, a 1-buten-3-yl group, a 1-buten-4-yl group, a 2-buten-1-yl group, a 2-buten-2-yl group, a 1-penten-1-yl group, a 1-penten-2-yl group, a 1-penten-3-yl group, a 2-penten-1-yl group, a 2-penten-2-yl group, a 2-penten-3-yl group, a 1-hexen-1-yl group, a 1-hexen-2-yl group, a 1-hexen-3-yl group, a 2-methyl-1-propen-1-yl group and the like.

The "$C_2$ to $C_6$ alkynyl group" in the term "$C_2$ to $C_6$ alkynyl group optionally having substituent(s)" as used herein means a linear or branched unsaturated hydrocarbon group having 2 to 6 carbon atoms and having at least one triple bond. Examples of the $C_2$ to $C_6$ alkynyl group may include an ethynyl group, a 1-propynyl group, a 2-propynyl group, a 1-butynyl group, a 2-butynyl group, a 3-butynyl group, a 3-methyl-1-propynyl group, a 1-ethynyl-2-propynyl group, a 2-methyl-3-propynyl group, a 1-pentynyl group, a 1-hexynyl group, a 1,3-hexanediynyl group, a 1,5-hexanediynyl group and the like.

The $C_1$ to $C_6$ alkoxycarbonyl group in the terms "$C_1$ to $C_6$ alkoxycarbonyl group optionally having substituent(s)" and "$C_1$ to $C_6$ alkoxycarbonyl group" as used herein means a linear or branched alkoxycarbonyl group having 1 to 6 carbon atoms. Examples of the $C_1$ to $C_6$ alkoxycarbonyl group may include a methoxycarbonyl group, an ethoxycarbonyl group, a propoxycarbonyl group, an isopropoxycarbonyl group, an isobutoxycarbonyl group, a butoxycarbonyl group, a sec-butoxycarbonyl group, a tert-butoxycarbonyl group, a pentyloxycarbonyl group, a hexyloxycarbonyl group and the like. Preferred examples thereof may include a methoxycarbonyl group and a tert-butoxycarbonyl group.

The halo-$C_1$ to $C_6$ alkoxy group in the terms "halo-$C_1$ to $C_6$ alkoxy group optionally having substituent(s)" and "halo-$C_1$ to $C_6$ alkoxy group" as used herein means a $C_1$ to $C_6$ alkoxy group substituted with 1 to 5 halogen atoms of the same kind or different kinds. Examples of the halo-$C_1$ to $C_6$ alkoxy group may include a fluoromethoxy group, a difluoromethoxy group, a trifluoromethoxy group, a 2-fluoroethoxy group, a 2-chloroethoxy group, a 2,2-difluoroethoxy group, a 1,1-difluoroethoxy group, a 1,2-difluoroethoxy group, a 2,2,2-trifluoroethoxy group, a 1,1,2,2,2-pentafluoroethoxy group, a 2,2,2-trichloroethoxy group, a 3-fluoropropoxy group, a 2-fluoropropoxy group, a 1-fluoropropoxy group, a 3,3-difluoropropoxy group, a 2,2-difluoropropoxy group, a 1,1-difluoropropoxy group, a 4-fluorobutoxy group, a 5-fluoropentoxy group, a 6-fluorohexyloxy group and the like.

The term "$C_2$ to $C_6$ alkylene group" as used herein means a divalent linear or branched saturated hydrocarbon chain having 2 to 6 carbon atoms. Examples of the $C_2$ to $C_6$ alkylene group may include —(CH$_2$)$_2$—, —(CH$_2$)$_3$—, —CH(CH$_3$)CH$_2$—, —CH$_2$CH(CH$_3$)—, —(CH$_2$)$_4$—, —CH(CH$_3$)—(CH$_2$)$_2$—, —(CH$_2$)$_2$—CH(CH$_3$)—, —CH(CH$_2$CH$_3$)—CH$_2$—, —C(CH$_3$)$_2$CH$_2$—, —CH$_2$—C(CH$_3$)$_2$—, —CH(CH$_3$)—CH(CH$_3$)—, —(CH$_2$)$_5$—, —CH(CH$_3$)—(CH$_2$)$_3$—, —C(CH$_3$)$_2$CH$_2$CH$_2$—, —(CH$_2$)$_6$—, —C(CH$_3$)$_2$—(CH$_2$)$_3$— and the like. Preferred examples thereof may include —(CH$_2$)$_2$— and —(CH$_2$)$_3$—.

The term "aryloxy group" as used herein means an aromatic hydrocarbon alkoxy group having 6 to 14 carbon atoms. Examples of the aryloxy group may include a phenyloxy group, an indenyloxy group, a naphthyloxy group, a phenanthrenyloxy group, an anthracenyloxy group and the like.

The term "$C_1$ to $C_6$ alkylamino group" as used herein means an amino group in which one or two hydrogen atoms in the amino group are substituted with linear or branched alkyl groups having 1 to 6 carbon atoms. Examples of the $C_1$ to $C_6$ alkylamino group may include a methylamino group, an ethylamino group, a propylamino group, an isopropylamino group, a butylamino group, an isobutylamino group, a sec-butylamino group, a tert-butylamino group, a pentylamino group, an isopentylamino group, a neopentylamino group, a 1-methylbutylamino group, a 2-methylbutylamino group, a 1,2-dimethylpropylamino group, a hexylamino group, an isohexylamino group, a dimethylamino group, a diethylamino group, an N-ethyl-N-methylamino group, an N-ethyl-N-propylamino group and the like.

The term "$C_1$ to $C_6$ acylamino group" as used herein means an amino group substituted with $C_1$ to $C_6$ acyl. Examples of the $C_1$ to $C_6$ acylamino group may include a formylamino group, an acetylamino group, a propanoylamino group, a butanoylamino group, a pentanoylamino group, a hexanoylamino group and the like.

The term "$C_1$ to $C_3$ alkyl group" as used herein means a linear or branched alkyl group having 1 to 3 carbon atoms. Examples of the $C_1$ to $C_3$ alkyl group may include a methyl group, an ethyl group, a propyl group, and an isopropyl group.

The term "$C_1$ to $C_3$ alkoxy group" as used herein means a linear or branched alkoxy group having 1 to 3 carbon atoms. Examples of the $C_1$ to $C_3$ alkoxy group may include a methoxy group, an ethoxy group, a propoxy group, and an isopropoxy group.

Examples of an "aromatic hydrocarbon cyclic group" as used herein may include a phenyl group, an indenyl group, a 1-naphthyl group, a 2-naphthyl group, an azulenyl group, a heptalenyl group, a biphenyl group, an indacenyl group, an acenaphthyl group, a fluorenyl group, a phenalenyl group, a phenanthrenyl group, an anthracenyl group, a benzocyclooctenyl group and the like.

The term "aromatic heterocyclyl group" as used herein means an aromatic cyclic structure containing a nitrogen atom, an oxygen atom, or a sulfur atom. Examples of the aromatic heterocyclyl group may include a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyridyl group, a pyridazinyl group, a pyrimidinyl group, a pyrazinyl group and the like. The above "heterocyclyl group" may be condensed with another cyclic group. Examples of such a heterocyclyl group may include an isobenzofuranyl group, a benzoxazolyl group, a benzisoxazolyl group, a benzothiazolyl group, a benzisothiazolyl group, a chromenyl group, a chromanonyl group, a xanthenyl group, a phenoxathiinyl group, an indolizinyl group, an isoindolizinyl group, an indolyl group, an indazolyl group, a purinyl group, a quinolizinyl group, an isoquinolyl group, a quinolyl group, a phthalazinyl group, a naphthyridinyl group, a quinoxalinyl group, a quinazolinyl group, a carbazolyl group, a carbolinyl group, an acridinyl group, an isoindolinyl group and the like.

No particular limitation is imposed on the groups acceptable as the "substituent(s)" in the "phenyl group optionally having substituent(s)," the "monocyclic aromatic heterocyclyl group optionally having substituent(s)" "bicyclic aromatic heterocyclyl group having 9 or 10 atoms and optionally having substituent(s)", "heterocycle optionally having substituent(s)" and the "heterocyclyl group optionally having substituent(s)," so long as the substituent(s) are generally known substituent(s). Examples of these substituent(s) may include halogen atoms, an amino group, a hydroxy group, a cyano group, a nitro group, a carboxy group, $C_1$ to $C_6$ alkoxycarbonyl groups, a formyl group, $C_1$ to $C_6$ acyl groups, $C_1$ to $C_6$ alkyl groups, $C_1$ to $C_6$ alkylamino groups, $C_1$ to $C_6$ alkoxy groups, $C_1$ to $C_6$ alkylsulfanyl groups, $C_3$ to $C_6$ cycloalkyl groups, 3- to 10-membered heterocycloalkyl groups, aromatic hydrocarbon cyclic groups optionally having a halogen atom, aromatic heterocyclyl groups, $C_1$ to $C_6$ acylamino groups, $C_3$ to $C_6$ cycloalkylcarbonylamino groups, 3- to 10-membered heterocycloalkylcarbonylamino groups, aromatic hydrocarbon cyclic carbonylamino groups, aromatic heterocyclyl carbonylamino groups and the like.

No particular limitation is imposed on the groups acceptable as the "substituent(s)" in the "$C_1$ to $C_6$ alkoxy group optionally having substituent(s)," the "$C_1$ to $C_6$ alkyl group optionally having substituent(s)," the "$C_1$ to $C_6$ acyl group optionally having substituent(s)," the "$C_1$ to $C_6$ alkylsulfanyl group optionally having substituent(s)," the "$C_1$ to $C_6$ alkylsulfinyl group optionally having substituent(s)," the "$C_1$ to $C_6$ alkylsulfonyl group optionally having substituent(s)," the "$C_3$ to $C_6$ cycloalkyl group optionally having substituent(s)," the "$C_2$ to $C_6$ alkenyl group optionally having substituent (s)," and the "$C_1$ to $C_6$ alkoxycarbonyl group optionally having substituent(s)" so long as the substituent(s) are generally known substituent(s). Examples of these substituent(s) may include halogen atoms, an amino group, a hydroxy group, a cyano group, a nitro group, a carboxy group, $C_1$ to $C_6$ alkoxycarbonyl groups, a formyl group, $C_1$ to $C_6$ acyl groups, $C_1$ to $C_6$ alkyl groups, $C_1$ to $C_6$ alkylamino groups, $C_1$ to $C_6$ alkoxy groups, $C_1$ to $C_6$ alkylsulfanyl groups, $C_3$ to $C_6$ cycloalkyl groups, 3- to 10-membered heterocycloalkyl groups, aromatic hydrocarbon cyclic groups optionally having a halogen atom, aromatic heterocyclyl groups, $C_1$ to $C_6$ alkylcarbonylamino groups, $C_3$ to $C_6$ cycloalkylcarbonylamino groups, 3- to 10-membered heterocycloalkylcarbonylamino groups, aromatic hydrocarbon cyclic carbonylamino groups, aromatic heterocyclic carbonylamino groups and the like.

Hereinafter, the present embodiment will be described in more detail.

In the following, descriptions of the definitions of functional groups included in general formulas may be omitted, and the definitions already described may be quoted instead. The definitions quoted refer to definitions in the description of the following embodiment.

As for the definitions of functional groups included in the general formulas, the definition of a symbol is common to general formulas containing this symbol, unless otherwise mentioned.

The present embodiment relates to a urea compound represented by the following general formula (I) or a pharmacologically acceptable salt thereof.

A compound represented by the general formula (I) or a pharmacologically acceptable salt thereof:

[Chem.10]

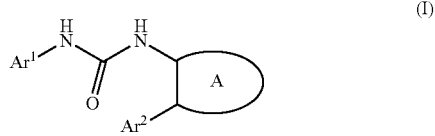

wherein, in the formula (I), $Ar^1$ is a phenyl group optionally having substituent(S), a monocyclic aromatic heterocyclyl group optionally having substituent(S), or a bicyclic aromatic heterocyclyl group having 9 or 10 atoms and optionally having substituent(s);

$Ar^2$ is a phenyl group optionally having substituent(S) (provided that when A is A1, the phenyl group whose substituent(s) is only halogen atom(s) is excluded), a monocyclic aromatic heterocyclyl group optionally having substituent(S), or a bicyclic aromatic heterocyclyl group having 9 or 10 atoms and optionally having substituent(s);

A is a group selected from the group consisting of the following A1), A2), A3), A4), and A5):

[Chem.11]

A1)

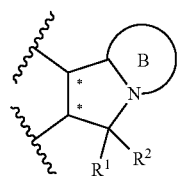

A2)

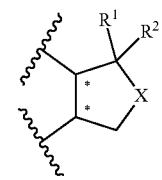

A3)

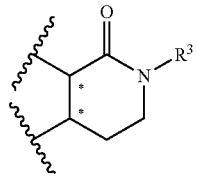

A4)

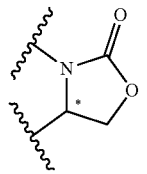

A5)

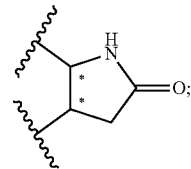

wherein $R^1$ and $R^2$ are independently a hydrogen atom or a $C_1$ to $C_6$ alkyl group optionally having substituent(S), or $R^1$ and $R^2$ together form a $C_2$ to $C_6$ alkylene group;

$R^3$ is a hydrogen atom or a $C_1$ to $C_6$ alkyl group optionally having substituent(S);

X is an oxygen atom, a sulfur atom, or $SO_2$;

B is a heterocyclyl group optionally having substituent (S); and each carbon atom marked with an asterisk is an asymmetric carbon atom.

The term "independently" means that at least two substituents present may be the same or different.

In the compound (I) of the present embodiment or a pharmacologically acceptable salt thereof, preferred substituents are as follows.

A is a group selected from the group consisting of the following A1), A2), A3), A4), and A5).

[Chem.12]

A1)

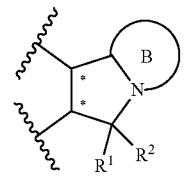

A2)

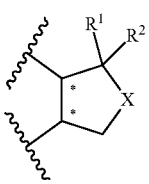

A3)

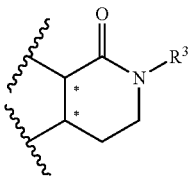

A4)

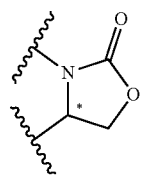

A5)

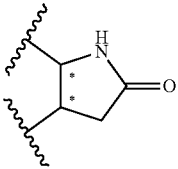

Preferably, A is a group selected from the group consisting of the following A1ba), A1bb), A1bc), A1ca), A1cb), A1cc), A1cd), A2), A3), A4), and A5).

[Chem.13]

A1ba)

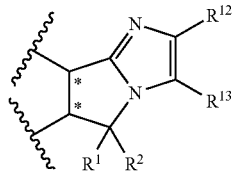

A1bb) 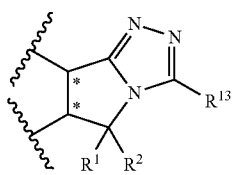

A1bc) 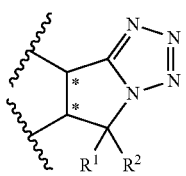

A1ca) 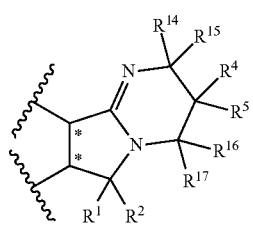

A1cb) 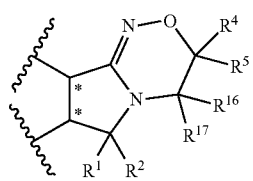

A1cc) 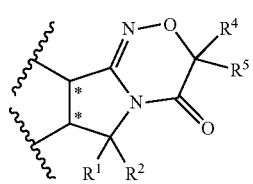

A1cd) 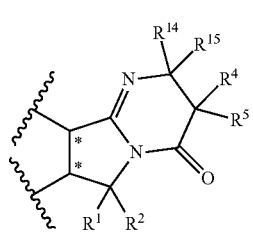

A2) 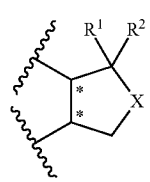

A3) 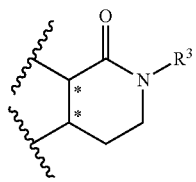

A4) 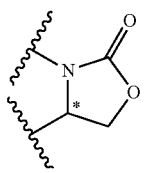

A5) 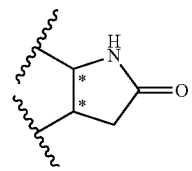

$R^1$ and $R^2$ are independently a hydrogen atom or a $C_1$ to $C_6$ alkyl group optionally having substituent(S), or $R^1$ and $R^2$ together form a $C_2$ to $C_6$ alkylene group.

$R^3$ is a hydrogen atom or a $C_1$ to $C_6$ alkyl group optionally having substituent(S).

$R^4$, $R^5$, $R^{14}$, $R^{15}$, $R^{16}$, and $R^{17}$ are independently a hydrogen atom or a $C_1$ to $C_6$ alkyl group optionally having substituent(S), or $R^4$ and $R^5$, $R^{14}$ and $R^{15}$, or $R^{16}$ and $R^{17}$ may together form a $C_3$ to $C_6$ cycloalkyl group or a 3- to 10-membered heterocycloalkyl group.

$R^{12}$ and $R^{13}$ are independently a hydrogen atom, a halogen atom, a cyano group, a hydroxy group, a $C_1$ to $C_6$ alkyl group optionally having substituent(S), a $C_1$ to $C_6$ alkoxy group optionally having substituent(S), a $C_1$ to $C_6$ alkoxycarbonyl group optionally having substituent(S), a $C_1$ to $C_6$ acyl group optionally having substituent(S), a $C_1$ to $C_6$ alkylsulfanyl group optionally having substituent(S), a $C_1$ to $C_6$ alkylsulfinyl group optionally having substituent(S), a $C_1$ to $C_6$ alkylsulfonyl group optionally having substituent(S), a heterocyclyl group optionally having substituent(S), —CONR$^{18}$R$^{19}$, or —NR$^{18}$R$^{19}$, wherein when $R^{12}$ and/or $R^{13}$ are —CONR$^{18}$R$^{19}$ or —NR$^{18}$R$^{19}$, $R^{18}$ is a hydrogen atom, a $C_1$ to $C_6$ alkyl group optionally having substituent (S), a $C_1$ to $C_6$ acyl group optionally having substituent(S), or a $C_1$ to $C_6$ alkylsulfonyl group optionally having substituent(S), and $R^{19}$ is a hydrogen atom or a $C_1$ to $C_6$ alkyl group optionally having substituent(S), or $R^{18}$ and $R^{19}$ together form 3- to 10-membered heterocycloalkyl group.

X is an oxygen atom, a sulfur atom, or $SO_2$.

Preferably, $R^1$ is a hydrogen atom or a $C_1$ to $C_3$ alkyl group.

Preferably, $R^2$ is a hydrogen atom or a $C_1$ to $C_3$ alkyl group.

Preferably, $R^3$ is a hydrogen atom or a $C_1$ to $C_3$ alkyl group.

Preferably, $R^4$ is a hydrogen atom or a $C_1$ to $C_3$ alkyl group.

Preferably, $R^5$ is a hydrogen atom or a $C_1$ to $C_3$ alkyl group.

Preferably, $R^{14}$ is a hydrogen atom or a $C_1$ to $C_3$ alkyl group.

Preferably, $R^{15}$ is a hydrogen atom or a $C_1$ to $C_3$ alkyl group.

Preferably, $R^{16}$ is a hydrogen atom or a $C_1$ to $C_3$ alkyl group.

Preferably, $R^{17}$ is a hydrogen atom or a $C_1$ to $C_3$ alkyl group.

Preferably, $R^{12}$ is a hydrogen atom, a halogen atom, a cyano group, a $C_1$ to $C_6$ alkyl group optionally having substituent(S), a $C_1$ to $C_6$ alkoxy group optionally having substituent(S), a halo-$C_1$ to $C_6$ alkoxy group, a $C_1$ to $C_6$ acyl group optionally having substituent(S), a $C_1$ to $C_6$ alkylsulfanyl group optionally having substituent(S), a $C_1$ to $C_6$ alkylsulfinyl group optionally having substituent(S), —$CONR^{18}R^{19}$ or —$NR^{18}R^{19}$.

When $R^{12}$ is —$CONR^{18}R^{19}$ or —$NR^{18}R^{19}$, preferably $R^{18}$ is a hydrogen atom, a $C_1$ to $C_6$ alkyl group, or a $C_1$ to $C_6$ acyl group, and $R^{19}$ is a hydrogen atom or a $C_1$ to $C_6$ alkyl group, or $R^{18}$ and $R^{19}$ together form a pyrrolidinyl group, a piperidinyl group, a piperazinyl group, or a morpholinyl group.

More preferably, $R^{12}$ is a hydrogen atom, a fluorine atom, a chlorine atom, a cyano group, a $C_1$ to $C_6$ alkoxy group, a halo-$C_1$ to $C_6$ alkoxy group, a $C_1$ to $C_6$ alkyl group, a $C_1$ to $C_6$ alkylsulfanyl group, or a $C_1$ to $C_6$ alkylsulfinyl group.

Preferably, $R^{13}$ is a hydrogen atom, a halogen atom, a cyano group, a $C_1$ to $C_6$ alkyl group optionally having substituent(S), a $C_1$ to $C_6$ alkoxy group optionally having substituent(S), a halo-$C_1$ to $C_6$ alkoxy group, a $C_1$ to $C_6$ acyl group optionally having substituent(S), a $C_1$ to $C_6$ alkylsulfanyl group optionally having substituent(S), a $C_1$ to $C_6$ alkylsulfinyl group optionally having substituent(S), —$CONR^{18}R^{19}$, or —$NR^{18}R^{19}$.

When $R^{13}$ is —$CONR^{18}R^{19}$ or —$NR^{18}R^{19}$, preferably $R^{18}$ is a hydrogen atom, a $C_1$ to $C_6$ alkyl group, or a $C_1$ to $C_6$ acyl group, and $R^{19}$ is a hydrogen atom or a $C_1$ to $C_6$ alkyl group, or $R^{18}$ and $R^{19}$ together form a pyrrolidinyl group, a piperidinyl group, a piperazinyl group, or a morpholinyl group.

More preferably, $R^{13}$ is a hydrogen atom, a fluorine atom, a chlorine atom, a cyano group, a $C_1$ to $C_6$ alkoxy group, a halo-$C_1$ to $C_6$ alkoxy group, a $C_1$ to $C_6$ alkyl group, a $C_1$ to $C_6$ alkylsulfanyl group, or a $C_1$ to $C_6$ alkylsulfinyl group.

More preferably, $Ar^1$ is the following C1).

[Chem.14]

C1)

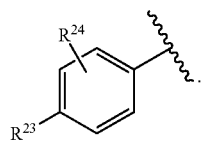

Preferably, $R^{23}$ is a hydrogen atom, a halogen atom, a cyano group, a trifluoromethyl group, or a $C_1$ to $C_3$ alkyl group.

Preferably, $R^{24}$ is a hydrogen atom, a halogen atom, or a hydroxy group.

More preferably, $Ar^2$ is the following B1a), B3a), or B4a).

[Chem. 15]

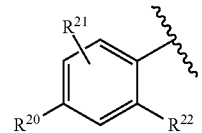

B1a)

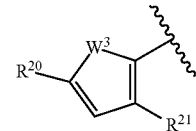

B3a)

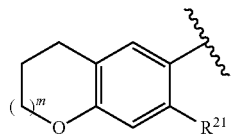

B4a)

Preferably, $R^{20}$ is a fluorine atom, a chlorine atom, a cyano group, a $C_1$ to $C_6$ alkyl group, a $C_1$ to $C_6$ alkoxy group, a halo-$C_1$ to $C_6$ alkoxy group, a $C_1$ to $C_6$ alkylsulfanyl group, a $C_1$ to $C_6$ alkylsulfinyl group, —$CONR^{18}R^{19}$, or —$NR^{18}R^{19}$, wherein when $R^{20}$ is —$CONR^{18}R^{19}$ or —$NR^{18}R^{19}$, $R^{18}$ is a hydrogen atom, a $C_1$ to $C_6$ alkyl group, a $C_1$ to $C_6$ acyl group, or a $C_1$ to $C_6$ alkylsulfonyl group, and $R^{19}$ is a hydrogen atom or a $C_1$ to $C_6$ alkyl group, or $R^{18}$ and $R^{19}$ together form 3- to 10-membered heterocycloalkyl group, and particularly preferably $R^{20}$ is a cyano group, an ethyl group, or a $C_1$ to $C_3$ alkoxy group.

Preferably, $R^{21}$ is a hydrogen atom or a halogen atom, and particularly preferably $R^{21}$ is a hydrogen atom, a fluorine atom, or a chlorine atom.

Preferably, $R^{22}$ is a hydrogen atom or a halogen atom, and particularly preferably $R^{22}$ is a hydrogen atom, a fluorine atom, or a chlorine atom.

Preferably, m is 0.

Provided that when $Ar^2$ is B1a), $R^{20}$, $R^{21}$, and $R^{22}$ are not a combination of a hydrogen atom and a halogen atom.

Preferred examples of the compound of the present embodiment may include the following compounds:

(±)-cis-1-(4-chlorophenyl)-3-[4-(4-methoxyphenyl)tetrahydrofuran-3-yl]urea, (±)-cis-1-(3-fluorophenyl)-3-[4-(4-methoxyphenyl)tetrahydrofuran-3-yl]urea, (±)-cis-1-(2-fluorophenyl)-3-[4-(4-methoxyphenyl)tetrahydrofuran-3-yl]urea, (±)-cis-1-(2,4-difluorophenyl)-3-[4-(4-methoxyphenyl)tetrahydrofuran-3-yl]urea, (±)-cis-1-(3,4-difluorophenyl)-3-[4-(4-methoxyphenyl)tetrahydrofuran-3-yl]urea, (±)-cis-1-(4-cyanophenyl)-3-[4-(4-methoxyphenyl)tetrahydrofuran-3-yl]urea, (±)-cis-1-(5-chlorothiophen-2-yl)-3-[4-(4-methoxyphenyl)tetrahydrofuran-3-yl]urea, (±)-cis-1-[4-(2,6-difluoro-4-methoxyphenyl)tetrahydrofuran-3-yl]-3-(4-fluorophenyl)urea, (±)-trans-1-(4-chlorophenyl)-3-[4-(4-methoxyphenyl)tetrahydrofuran-3-yl]urea, (±)-1-(4-chlorophenyl)-3-[4-(4-methoxyphenyl)-1,1-dioxidotetrahydrothiophen-3-yl]urea,
(±)-trans-1-(4-chlorophenyl)-3-[4-(4-methoxyphenyl)-2-oxopiperidin-3-yl]urea,
(+)-cis-1-(4-chlorophenyl)-3-[4-(4-methoxyphenyl)tetrahydrofuran-3-yl]urea,
(+)-cis-1-(4-fluorophenyl)-3-[4-(4-methoxyphenyl)tetrahydrofuran-3-yl]urea,
(+)-cis-1-(4-fluorophenyl)-3-[4-(4-methoxyphenyl)-2,2-dimethyltetrahydrofuran-3-yl] urea,
(±)-cis-1-[4-(4-chlorophenyl)tetrahydrofuran-3-yl]-3-(4-fluorophenyl)urea,
(±)-cis-1-[4-(4-fluorophenyl)tetrahydrofuran-3-yl]-3-(4-fluorophenyl)urea,
(±)-cis-1-[4-(4-cyanophenyl)tetrahydrofuran-3-yl]-3-(4-fluorophenyl)urea,
(±)-1-(4-chlorophenyl)-3-[4-(4-methoxyphenyl)-2-oxooxazolidin-3-yl]urea,
(±)-trans-1-(4-fluorophenyl)-3-[3-(4-methoxyphenyl)-5-oxopyrrolidin-2-yl]urea,
(−)-1-[(6R*,7S*)-6-(2,6-difluoro-4-methoxyphenyl)-3-methyl-6,7-dihydro-5H-pyrrolo[2,1-c][1,2,4]triazol-7-yl]-3-(4-fluorophenyl)urea,
(−)-1-[(6R*,7S*)-6-(2,6-difluoro-4-methoxyphenyl)-6,7-dihydro-5H-pyrrolo[1,2-a]imidazol-7-yl]-3-(4-fluorophenyl)urea,
(−)-1-(4-fluorophenyl)-3-[(6R*,7S*)-6-(4-methoxyphenyl)-6,7-dihydro-5H-pyrrolo[1,2-d]tetrazol-7-yl]urea,
(−)-1-[(6R*,7S*)-6-(2,6-difluoro-4-methoxyphenyl)-6,7-dihydro-5H-pyrrolo[1,2-d]tetrazol-7-yl]-3-(4-fluorophenyl)urea,
(−)-1-[(6R*,7S*)-6-(6-fluoro-2,3-dihydrobenzofuran-5-yl)-6,7-dihydro-5H-pyrrolo[1,2-d]tetrazol-7-yl]-3-(4-fluorophenyl)urea,
(−)-1-[(7R*,8S*)-7-(2,6-difluoro-4-methoxyphenyl)-2,3,4,6,7,8-hexahydropyrrolo[1,2-a]pyrimidin-8-yl]-3-(4-fluorophenyl)urea,
1-[(7R*,8S*)-7-(2,6-difluoro-4-methoxyphenyl)-4,6,7,8-tetrahydro-3H-pyrrolo[2,1-c][1,2,4]oxadiazin-8-yl]-3-(4-fluorophenyl)urea,
(−)-1-[(7R*,8S*)-7-(2,6-difluoro-4-methoxyphenyl)-4-oxo-4,6,7,8-tetrahydro-3H-pyrrolo[2,1-c][1,2,4]oxadiazin-8-yl]-3-(4-fluorophenyl)urea,
(−)-1-[(7R*,8S*)-7-(2,6-difluoro-4-methoxyphenyl)-4-oxo-2,3,4,6,7,8-hexahydropyrrolo[1,2-a]pyrimidin-8-yl]-3-(4-fluorophenyl)urea, or
1-(4-fluorophenyl)-3-[(7R*,8S*)-7-(4-methoxyphenyl)-4-oxo-4,6,7,8-tetrahydro-3H-pyrrolo[2,1-c][1,2,4]oxadiazin-8-yl]urea.

If necessary, the compound (I) of the present embodiment can be converted to a pharmacologically acceptable salt according to a usual method. The pharmacologically acceptable salt means a salt with a pharmacologically acceptable nontoxic base or acid (for example, an inorganic or organic base or an inorganic or organic acid).

Examples of the salt derived from a pharmacologically acceptable nontoxic base may include: salts with inorganic bases such as sodium salts, potassium salts, calcium salts, magnesium salts and the like; and salts with organic bases such as piperidine, morpholine, pyrrolidine, arginine, lysine and the like.

Examples of the salt derived from a pharmacologically acceptable nontoxic acid may include: acid addition salts with mineral acids such as hydrochloric acid, hydrobromic acid, sulfuric acid, nitric acid and the like; and acid addition salts with organic acids such as formic acid, acetic acid, maleic acid, fumaric acid, succinic acid, lactic acid, malic acid, tartaric acid, citric acid, methanesulfonic acid, p-toluenesulfonic acid, salicylic acid, stearic acid, palmitic acid and the like.

The compound (I) of the present embodiment or a pharmacologically acceptable salt thereof may be present as a hydrate or a solvate. Any hydrate and solvate formed from the urea derivative represented by the general formula (I) above, including any of the preferred compounds specifically described above, or a salt thereof are included in the scope of the present invention. Examples of the solvent that can form the solvate may include methanol, ethanol, 2-propanol, acetone, ethyl acetate, dichloromethane, di-isopropyl ether and the like.

The compound (I) of the present embodiment or a pharmacologically acceptable salt thereof may be a racemate and also includes their optically active substances, stereoisomers, and rotational isomers.

When the compound (I) of the present embodiment is one of its optical isomers having one or more asymmetric carbon atom, the configuration of each asymmetric carbon atom in the compound (I) of the present embodiment may be any one of the R configuration and the S configuration. Any one of the optical isomers is included in the present invention, and a mixture of these optical isomers is also included in the present invention. A mixture of optically active substances may be a racemate formed of equal amounts of the optical isomers, and this racemate is also included in the scope of the present invention. When the compound (I) of the present embodiment is a solid or crystalline racemate, the racemate, racemic mixture, and racemic solid solution are included in the scope of the present invention.

When the compound (I) of the present embodiment includes geometrical isomers, all the geometrical isomers are included in the present invention.

When the compound (I) of the present embodiment includes tautomers, all the tautomers are included in the present invention.

Pharmacologically acceptable salts of the compound (I) include proton tautomers thereof.

The compound (I) of the present embodiment or a pharmacologically acceptable salt thereof may be a compound labeled with an isotope (for example, $^{3}H$, $^{14}C$, $^{35}S$ and the like). Such a compound is also included in the present invention.

The compound (I) of the present embodiment or a pharmacologically acceptable salt thereof may be a deuterium-substituted compound in which $^{1}H$ is substituted with $^{2}H(D)$. Such a compound is also included in the present invention.

The term "FPRL1 agonist effect" in the present embodiment means agonist activity obtained by the action on formyl peptide receptor like 1 (FPRL1).

The compound (I) of the present embodiment or a pharmacologically acceptable salt thereof exhibits superior agonist activity in, for example, a test of calcium influx into FPRL1-overexpressing cells. Therefore, it can be understood that the compound (I) of the present embodiment or a pharmacologically acceptable salt thereof is useful as a therapeutic or prophylactic agent for inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

Method of Producing the Compound (I) of the Present Embodiment

The compound (I) of the present embodiment or a pharmacologically acceptable salt thereof can be produced, for example, in accordance with processes described in the following schemes 1 to 17, methods similar thereto, methods described in other literatures, and methods similar thereto.

Synthesis of Compound (I)

The compound (I) of the present embodiment can be produced in accordance with methods described in Scheme 1, methods similar thereto, methods described in other literatures, and methods similar thereto.

Scheme 1

[Chem.16]

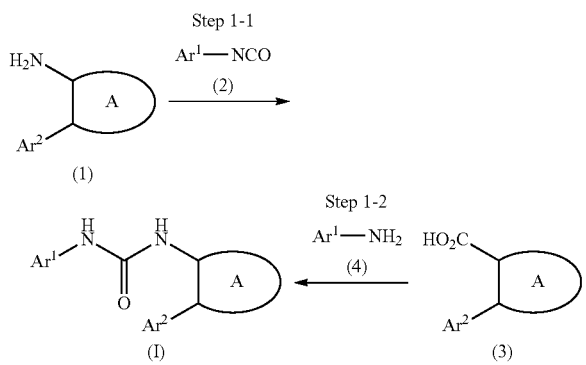

In the above formulas, $Ar^1$, $Ar^2$, and A are as described above.

Step 1-1

This step is a step of reacting Compound (1) with Compound (2) to produce Compound (I). Compound (I) can be produced by, for example, reacting Compound (1) with Compound (2) in a solvent in the presence or absence of a base. The amount of Compound (2) used is about 0.5-10 molar equivalents, preferably about 1-2 molar equivalents, per 1 mole of Compound (1).

The above reaction is generally performed in a solvent that does not adversely affect the reaction, and examples of the solvent used may include dichloromethane, 1,2-dichloroethane, benzene, toluene, tetrahydrofuran, ethyl acetate, methanol, water, mixed solvents thereof and the like. Examples of the base used may include an alkali metal hydride such as lithium hydride, sodium hydride, and potassium hydride; an alkali metal hydroxide such as sodium hydroxide and potassium hydroxide; a hydrogen carbonate such as sodium hydrogen carbonate and potassium hydrogen carbonate; a carbonate such as sodium carbonate and potassium carbonate; an organic acid salt such as sodium acetate; a tertiary amine such as trimethylamine, triethylamine, and N-methylmorpholine; an aromatic amine such as pyridine, picoline, and N,N-dimethylaniline; and the like. The amount of the base used is generally about 1-100 molar equivalents, preferably about 1-5 molar equivalents, per 1 mole of the compound. The reaction temperature can generally be performed at −20° C. to the reflux temperature of the solvent and is performed preferably at about 0° C. to 50° C. The reaction time varies depending on the starting materials used, the solvent used, the reaction temperature, or the like, but is generally about 10 minutes to 48 hours.

Compound (1) used in this step can be produced in accordance with methods described below in detail, methods similar thereto, methods described in other literatures, and methods similar thereto.

Further, Compound (2) used in this step may be a commercially available, or can be produced in accordance with methods described in other literatures, and methods similar thereto.

Step 1-2

This step is a step of reacting Compound (3) with Compound (4) to produce Compound (I). Compound (I) can be produced by, for example, allowing diphenylphosphoryl azide (DPPA) and the like to act on Compound (3) in a solvent in the presence or absence of a base and then reacting Compound (4) with the obtained product.

The above reaction is generally performed in a solvent that does not adversely affect the reaction, and examples of the solvent used may include benzene, toluene, tetrahydrofuran, acetonitrile, dioxane, mixed solvents thereof and the like. Examples of the base used may include trimethylamine, triethylamine, N-methylmorpholine and the like. The amount of the base used is generally about 0.5-100 molar equivalents, preferably about 1-5 molar equivalents per 1 mole of the compound. The reaction temperature can generally be performed at −10° C. to the reflux temperature of the solvent and is performed preferably at 20° C. to 120° C. The reaction time varies depending on the starting materials used, the solvent used, the reaction temperature, or the like, but is generally 10 minutes to 3 days.

Compound (3) used in this step can be produced in accordance with methods described below in detail, methods similar thereto, methods described in other literatures, and methods similar thereto.

Further, Compound (4) used in this step may be a commercially available, or can be produced in accordance with methods described in other literatures, and methods similar thereto.

Synthesis of Compound (1a)

Compound (1) of the present embodiment wherein A is a compound of the following formula (1a) (this compound may hereinafter be referred to as Compound (1a)) can be produced, for example, from Compound (5) in accordance with methods described in Scheme 2, methods similar thereto, methods described in other literatures, and methods similar thereto.

Scheme 2

[Chem.17]

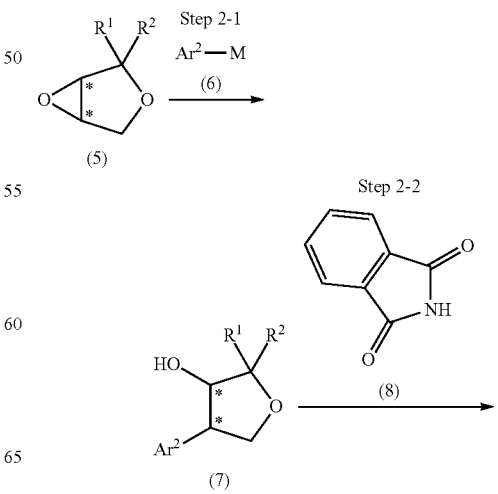

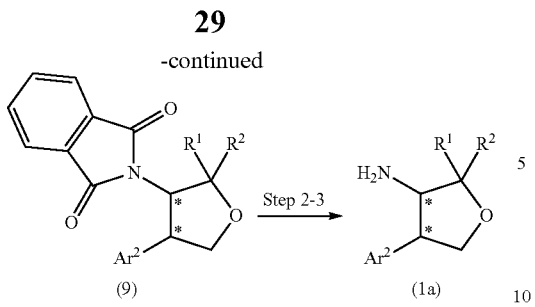

(9) Step 2-3 (1a)

In the above formulas, $Ar^2$, $R^1$, and $R^2$ are as described above, M is Li or MgBr, and each carbon atom marked with an asterisk is an asymmetric carbon atom.

Step 2-1

This step is a step of reacting Compound (5) and Compound (6) to produce Compound (7). Compound (7) can be produced by, for example, allowing Compound (5) to react Compound (6) in a solvent in the presence of a Lewis acid or a metal salt. Examples of the solvent used may include tetrahydrofuran, diethyl ether, mixed solvents thereof and the like. Examples of the Lewis acid used may include borontrifluoride and the like. Examples of the metal salt used may include copper iodide and the like. The reaction temperature can generally be performed at −78° C. to the reflux temperature of the solvent and is performed preferably at −78° C. to 30° C. The reaction time varies depending on the starting materials used, the solvent used, the reaction temperature, or the like, but is generally 30 minutes to 3 days. Further, Compound (5) and Compound (6) used in this step may be a commercially available, or can be produced in accordance with methods described in other literatures, and methods similar thereto.

Step 2-2

This step is a step of reacting Compound (7) with Compound (8) to produce Compound (9). Compound (9) can be produced by, for example, allowing Compound (7) to react Compound (8) in a solvent in the presence of a reagent used in Mitsunobu reaction. Examples of the solvent used may include tetrahydrofuran and the like. Examples of the reagent used in Mitsunobu reaction may include diethyl azodicarboxylate, bis(2-methoxyethyl)azodicarboxylate, triphenylphosphine, tributylphosphine, and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

Step 2-3

This step is a step of deprotecting the phthaloyl group in Compound (9) to produce Compound (1a). Compound (1a) can be produced by, for example, reacting Compound (9) in a solvent with a compound having an amino group, an acid, or a base. Examples of the solvent used may include water, methanol, ethanol, dichloromethane, tetrahydrofuran, acetic acid, and the like. Examples of the compound having an amino group used may include hydrazine, methylamine, and the like. Examples of the acid used may include hydrogen chloride, hydrogen bromide, and the like. Examples of the base used may include sodium hydroxide and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

Synthesis of Compound (1b)

Compound (1) of the present embodiment which is a compound of the following formula (1b) (this compound may hereinafter be referred to as Compound (1b)) can be produced, for example, from Compound (10) in accordance with methods described in Scheme 3, methods similar thereto, methods described in other literatures, and methods similar thereto.

Scheme 3

[Chem. 18]

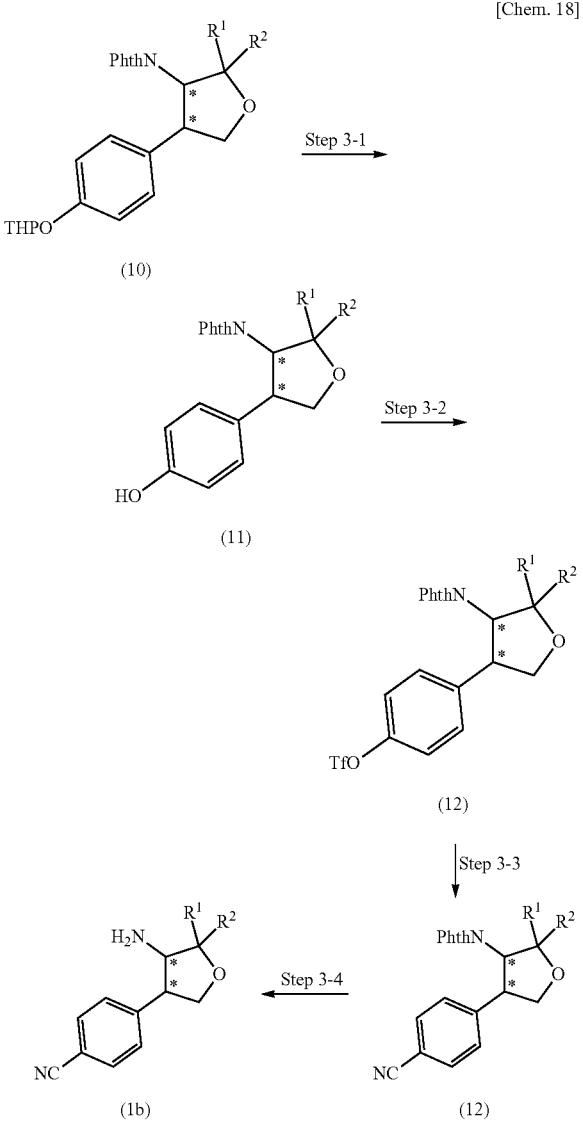

In the above formulas, $R^1$ and $R^2$ are as described above, and each carbon atom marked with an asterisk is an asymmetric carbon atom.

Step 3-1

This step is a step of deprotecting the THP group in Compound (10) to produce Compound (11). Compound (11) can be produced by, for example, reacting Compound (10) in a solvent in the presence of an acid. Examples of the solvent used may include methanol, ethanol, water, tetrahydrofuran, dichloromethane, mixed solvents thereof, and the like. Examples of the acid used may include hydrochloric acid, p-toluenesulfonic acid, acetic acid, trifluoroacetic acid, and the like. The reaction temperature can generally be performed at 0° C. to the reflux temperature of the solvent and is performed preferably at 20° C. to the reflux temperature of the solvent. The reaction time varies depending on the starting materials used, the solvent used, the reaction temperature, or the like, but is generally 30 minutes to 3 days.

Compound (10) used in this step can be produced in accordance with methods described at Step 2-1 and Step 2-2 in Scheme 2, methods similar thereto, methods described in other literatures, and methods similar thereto.

Step 3-2

This step is a step of trifluoromethanesulfonylating the hydroxy group in Compound (11) to produce Compound (12). Compound (12) can be produced by, for example, reacting Compound (11) and a trifluoromethanesulfonating agent in a solvent in the presence of a base. Examples of the solvent used may include dichloromethane, 1,2-dichloroethane, pyridine, tetrahydrofuran, N,N-dimethylformamide, 1,4-dioxane, acetonitrile, diethyl ether, mixed solvents thereof, and the like. Examples of the trifluoromethanesulfonating agent used may include N-phenylbis(trifluoromethanesulfonimide), trifluoromethanesulfonic anhydride, and the like. Examples of the base used may include potassium carbonate, sodium carbonate, sodium hydride, potassium phosphate, N,N-diisopropylethylamine, triethylamine, 2,6-lutidine, and the like. The reaction temperature can generally be performed at −78° C. to the reflux temperature of the solvent and is performed preferably at −20° C. to 30° C. The reaction time varies depending on the starting materials used, the solvent used, the reaction temperature, or the like, but is generally 30 minutes to 3 days.

Step 3-3

This step is a step of producing Compound (13) from Compound (12). Compound (13) can be produced by, for example, reacting Compound (12) and zinc cyanide (Zn(CN)$_2$) in a solvent in the presence of palladium reagent as a catalyst. Examples of the solvent used may include 1,4-dioxane, toluene, N,N-dimethylformamide, mixed solvents thereof, and the like. Examples of the palladium reagent used may include tetrakis(triphenylphosphine)palladium(0) (Pd(PPh$_3$)$_4$) and the like. The reaction temperature can generally be performed at 20° C. to the reflux temperature of the solvent and is performed preferably at 60° C. to 100° C. The reaction time varies depending on the starting materials used, the solvent used, the reaction temperature, or the like, but is generally 30 minutes to 3 days.

Step 3-4

This step is a step of producing Compound (1b) from Compound (13). Compound (1b) can be produced in accordance with methods described at Step 2-3 in Scheme 2, methods similar thereto, methods described in other literatures, and methods similar thereto.

Synthesis of Compound (1c)

Compound (1) of the present embodiment when A is a compound of the following formula (1c) (this compound may hereinafter be referred to as Compound (1c)) can be produced, for example, from Compound (14) in accordance with methods described in Scheme 4, methods similar thereto, methods described in other literatures, and methods similar thereto.

Scheme 4

[Chem.19]

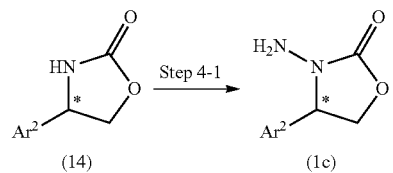

In the above formulas, Ar$^2$ is as described above, and each carbon atom marked with an asterisk is an asymmetric carbon atom.

Step 4-1

This step is a step of producing Compound (1c) from Compound (14). Compound (1c) can be produced by, for example, reacting Compound (14) in a solvent with O-(4-nitrobenzoyl)hydroxylamine in the presence of a base. Examples of the solvent used may include 1,4-dioxane and the like. Examples of the base used may include sodium hydride (NaH) and the like. The reaction temperature can generally be performed at 20° C. to the reflux temperature of the solvent and is performed preferably at 50° C. to 70° C. The reaction time varies depending on the starting materials used, the solvent used, the reaction temperature, or the like, but is generally 30 minutes to 3 days.

Synthesis of Compound (1d)

Compound (1) of the present embodiment when A is a compound of the following formula (1d) (this compound may hereinafter be referred to as Compound (1d)) can be produced, for example, from Compound (15) in accordance with methods described in Scheme 5, methods similar thereto, methods described in other literatures, and methods similar thereto.

Scheme 5

[Chem.20]

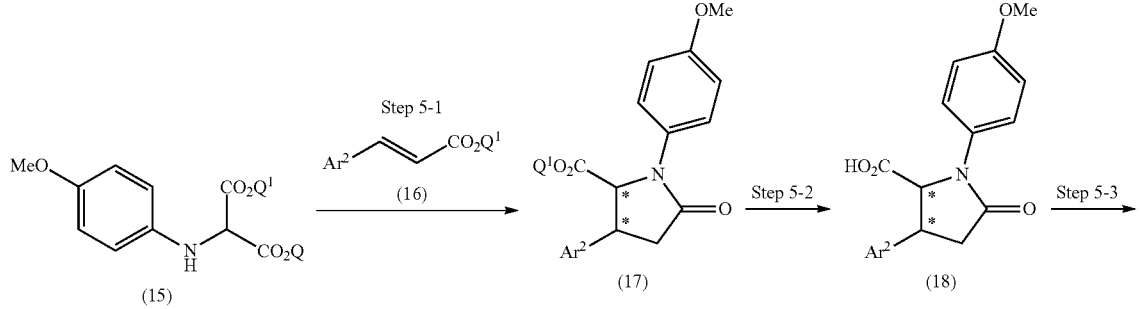

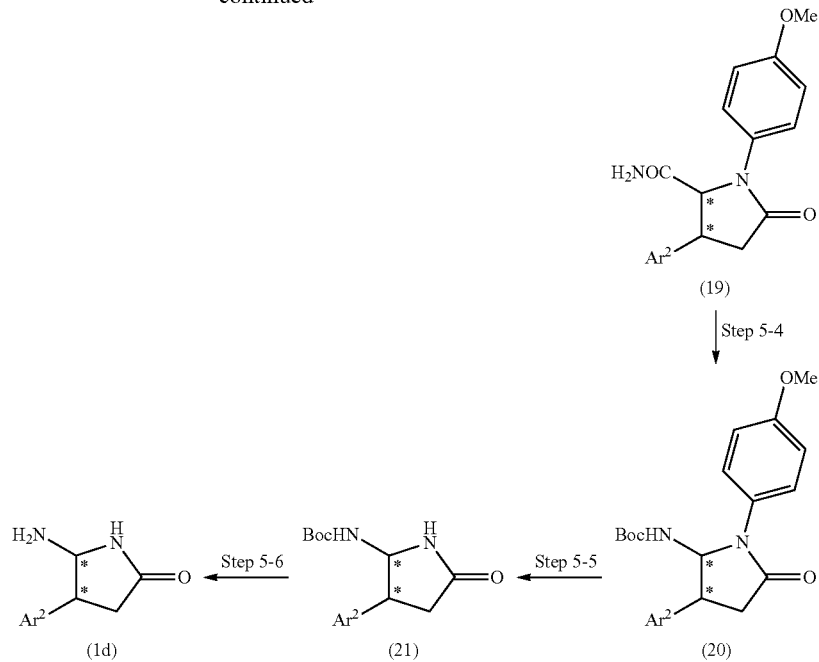

In the above formulas, $Ar^2$ is as described above, $Q^1$ is a $C_1$ to $C_6$ alkyl group, and each carbon atom marked with an asterisk is an asymmetric carbon atom.

Step 5-1

This step is a step of reacting Compound (15) with Compound (16) to produce Compound (17). Compound (17) can be produced by, for example, reacting Compound (15) in a solvent with Compound (16) in the presence of a base. Examples of the solvent used may include methanol, ethanol and the like. Examples of the base used may include sodium methoxide, sodium ethoxide, and the like. The reaction temperature can generally be performed at 0° C. to the reflux temperature of the solvent and is performed preferably at 70° C. to 90° C. The reaction time varies depending on the starting materials used, the solvent used, the reaction temperature, or the like, but is generally 30 minutes to 3 days.

Further, Compound (15) and Compound (16) used in this step may be a commercially available, or can be produced in accordance with methods described in other literatures, and methods similar thereto.

Step 5-2

This step is a step of hydrolyzing the ester part in Compound (17) to produce Compound (18). Compound (18) can be produced by, for example, reacting Compound (17) in a solvent in the presence of a base. Examples of the solvent used may include water, methanol, ethanol, propanol, 2-propanol, butanol, tetrahydrofuran, mixed solvents thereof, and the like. Examples of the base used may include lithium hydroxide, sodium hydroxide, potassium hydroxide, and the like. The reaction temperature can generally be performed at 0° C. to the reflux temperature of the solvent and is performed preferably at 10° C. to 70° C. The reaction time varies depending on the starting materials used, the solvent used, the reaction temperature, or the like, but is generally 30 minutes to 3 days.

Step 5-3

This step is a step of reacting Compound (18) with aqueous ammonia to produce Compound (19). Compound (19) can be produced by, for example, reacting Compound (18) with aqueous ammonia in the presence of a condensing agent. Examples of the solvent used may include N,N-dimethylformamide, dichloromethane, 1,4-dioxane, tetrahydrofuran, mixed solvents thereof, and the like. Examples of the condensing agent used may include 1-ethyl-3-(3-dimethylaminopropyl)carbodiimide (EDCI), dicyclohexylcarbodiimide (DCC), 2-(1H-7-azabenzotriazol-1-yl)-1,1,3,3-tetramethyluronium hexafluorophosphate methanaminium (HATU), and the like. Further, as necessary, N,N-dimethylaminopyridine, pyridine, 1-hydroxybenzotriazole (HOBT) and the like can be used as a reaction accelerator. The reaction temperature can generally be performed at 0° C. to the reflux temperature of the solvent and is performed preferably at 0° C. to 30° C.

Step 5-4

This step is a step of producing Compound (20) from Compound (19). Compound (20) can be produced by, for example, reacting Compound (19) in t-butanol with pyridine and (bis(trifluoroacetoxy)iodo)benzene. The reaction temperature can generally be performed at 0° C. to 100° C. and is performed preferably at 70° C. to 90° C. The reaction time is generally 30 minutes to 3 days.

Step 5-5

This step is a step of cleaving the methoxyphenyl group in Compound (20) to produce Compound (21). Compound (21) can be produced by, for example, reacting Compound (20) in a solvent with ammonium cerium(IV) nitrate. Examples of the solvent used may include acetonitrile and the like. The reaction temperature can generally be performed at −78° C. to the reflux temperature of the solvent and is performed preferably at −10° C. to 10° C. The reaction time varies depending on the starting materials used, the solvent used, the reaction temperature, or the like, but is generally 30 minutes to 3 days.

Step 5-6

This step is a step of deprotecting the tert-butoxycarbonyl (Boc) group in Compound (21) to produce Compound (1d).

Compound (1d) can be produced by, for example, reacting Compound (21) in a solvent with an acid such as trifluoroacetic acid (TFA), hydrogen chloride or the like. Examples of the solvent used may include dichloromethane, dioxane, ethyl acetate, methanol, water, mixed solvents thereof, and the like. The reaction temperature can generally be performed at 0° C. to the reflux temperature of the solvent and is performed preferably at 0° C. to 60° C. The reaction time varies depending on the starting materials used, the solvent used, the reaction temperature, or the like, but is generally 30 minutes to 3 days.

Synthesis of Compounds (3a, 3b)

Compound (3) of the present embodiment when A is compounds of the following formulae (3a, 3b) (this compound may hereinafter be referred to as Compounds (3a, 3b)) can be produced, for example, from Compound (22) in accordance with methods described in Scheme 6, methods similar thereto, methods described in other literatures, and methods similar thereto.

used may include N-phenylbis(trifluoromethanesulfonimide), trifluoromethanesulfonic anhydride, and the like. Examples of the base used may include potassium carbonate, sodium carbonate, sodium hydride, potassium phosphate, N,N-diisopropylethylamine, triethylamine, 2,6-lutidine, and the like. The reaction temperature can generally be performed at −78° C. to the reflux temperature of the solvent and is performed preferably at −20° C. to 30° C. The reaction time varies depending on the starting materials used, the solvent used, the reaction temperature, or the like, but is generally 30 minutes to 3 days. Further, Compound (22) used in this step may be a commercially available, or can be produced in accordance with methods described in other literatures, and methods similar thereto.

Step 6-2

This step is a step of reacting Compound (23) and Compound (24) to produce Compound (25). Compound (25) can be produced by, for example, reacting Compound (23) and Compound (24) in a solvent in the presence of a

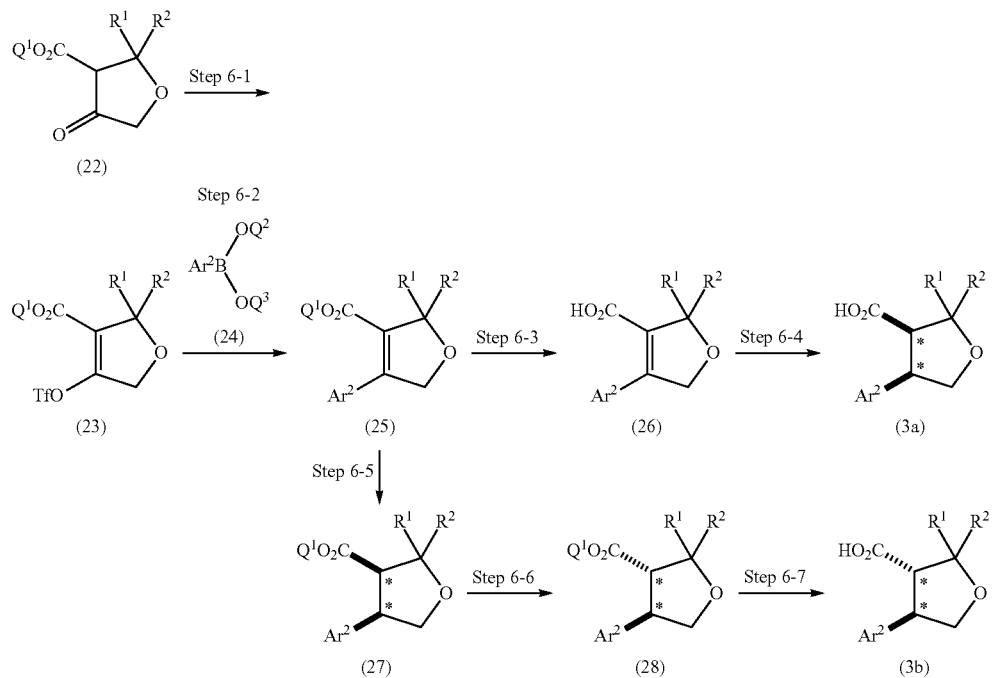

Scheme 6

In the above formulas, $Ar^2$, $R^1$, $R^2$, and $Q^1$ are as described above; $Q^2$ and $Q^3$ are a hydrogen atom or a $C_1$ to $C_6$ alkyl group optionally having substituent(s) (which may together form a ring); and each carbon atom marked with an asterisk is an asymmetric carbon atom.

Step 6-1

This step is a step of trifluoromethanesulfonylating Compound (22) to produce Compound (23). Compound (23) can be produced by, for example, reacting Compound (22) and a trifluoromethanesulfonating agent in a solvent in the presence of a base. Examples of the solvent used may include dichloromethane, 1,2-dichloroethane, pyridine, tetrahydrofuran, N,N-dimethylformamide, 1,4-dioxane, acetonitrile, diethyl ether, mixed solvents thereof, and the like. Examples of the trifluoromethanesulfonating agent catalytic palladium reagent and a base. Examples of the solvent used may include tetrahydrofuran, 1,4-dioxane, 1,2-dichloroethane, benzene, toluene, ethanol, propanol, N,N-dimethylformamide, dimethylsulfoxide, water, mixed solvents thereof, and the like. Examples of the palladium catalyst used may include tetrakis(triphenylphosphine)palladium and the like. Examples of the base used may include sodium carbonate, potassium carbonate, sodium hydrogen carbonate, potassium hydrogen carbonate, cesium carbonate, triethylamine, diisopropylethylamine, pyridine, 2,6-dimethylpyridine, 2,4,6-trimethylpyridine, and the like. The reaction temperature can generally be performed at 0° C. to the reflux temperature of the solvent and is performed preferably at 50° C. to the reflux temperature of the solvent. The reaction time varies depending on the starting materials used, the solvent used, the reaction temperature, or the like, but is generally 30 minutes to 3 days. Further, Compound (24) used in this step may be a commercially available, or can be produced in accordance with methods described in other literatures, and methods similar thereto.

Step 6-3

This step is a step of producing Compound (26) from Compound (25). Compound (26) can be produced in accordance with methods described at Step 5-2 in Scheme 5, methods similar thereto, methods described in other literatures, and methods similar thereto.

Step 6-4

This step is a step of producing Compound (3a) from Compound (26). Compound (3a) can be produced by, for example, hydrogenating Compound (26) in a solvent in the presence of a catalyst such as 10% palladium carbon (10% Pd—C). Examples of the solvent used may include methanol, ethanol, dichloromethane, tetrahydrofuran, ethyl acetate, mixed solvents thereof, and the like. The reaction temperature can generally be performed at 0° C. to the reflux temperature of the solvent and is performed preferably at 10° C. to 40° C. The reaction time varies depending on the starting materials used, the solvent used, the reaction temperature, or the like, but is generally 30 minutes to 3 days.

Step 6-5

This step is a step of producing Compound (27) from Compound (25). Compound (27) can be produced in accordance with methods described at Step 6-4 in Scheme 6, methods similar thereto, methods described in other literatures, and methods similar thereto.

Step 6-6

This step is a step of isomerizing Compound (27) to produce Compound (28). Compound (28) can be produced by, for example, reacting Compound (27) in a solvent in the presence of a base. Examples of the solvent used may include methanol and the like. Examples of the base used may include sodium methoxide and the like. The reaction temperature can generally be performed at 0° C. to the reflux temperature of the solvent and is performed preferably at 0° C. to 40° C. The reaction time varies depending on the starting materials used, the solvent used, the reaction temperature, or the like, but is generally 30 minutes to 3 days.

Step 6-7

This step is a step of producing Compound (3b) from Compound (28). Compound (3b) can be produced in accordance with methods described at Step 5-2 in Scheme 5, methods similar thereto, methods described in other literatures, and methods similar thereto.

Synthesis of Compound (3c)

Compound (3) of the present embodiment when A is a compound of the following formula (3c) (this compound may hereinafter be referred to as Compound (3c)) can be produced, for example, from Compound (29) in accordance with methods described in Scheme 7, methods similar thereto, methods described in other literatures, and methods similar thereto.

Scheme 7

[Chem.22]

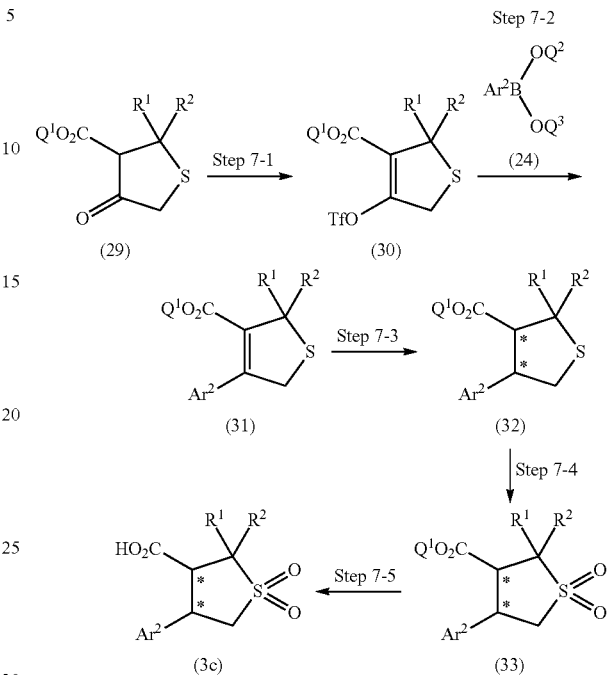

In the above formulas, $Ar^2$, $R^1$, $R^2$, $Q^1$, $Q^2$, and $Q^3$ are as described above, and each carbon atom marked with an asterisk is an asymmetric carbon atom.

Step 7-1

This step is a step of producing Compound (30) from Compound (29). Compound (30) can be produced in accordance with methods described at Step 6-1 in Scheme 6, methods similar thereto, methods described in other literatures, and methods similar thereto.

Step 7-2

This step is a step of reacting Compound (30) and Compound (24) to produce Compound (31). Compound (31) can be produced in accordance with methods described at Step 6-2 in Scheme 6, methods similar thereto, methods described in other literatures, and methods similar thereto.

Step 7-3

This step is a step of producing Compound (32) from Compound (31). Compound (32) can be produced in accordance with methods described at Step 6-5 in Scheme 6, methods similar thereto, methods described in other literatures, and methods similar thereto.

Step 7-4

This step is a step of oxidizing Compound (32) to produce Compound (33). Compound (33) can be produced by, for example, reacting Compound (32) in a solvent with an oxidizer. Examples of the solvent used may include dichloromethane, acetonitrile, water, mixed solvents thereof, and the like. Examples of the oxidizer used may include meta-chloroperbenzoic acid, hydrogen peroxide, and the like. The reaction temperature can generally be performed at −78° C. to the reflux temperature of the solvent and is performed preferably at −78° C. to 30° C. The reaction time varies depending on the starting materials used, the solvent used, the reaction temperature, or the like, but is generally 30 minutes to 3 days.

Step 7-5

This step is a step of hydrolyzing the ester moiety of Compound (33) to produce Compound (3c). Compound (3c) can be produced in accordance with methods described at Step 5-2 in Scheme 5, methods similar thereto, methods described in other literatures, and methods similar thereto.

Synthesis of Compound (3d)

Compound (3) of the present embodiment when A is a compound of the following formula (3d) (this compound may hereinafter be referred to as Compound (3d)) can be produced, for example, from Compound (34) in accordance with methods described in Scheme 8, methods similar thereto, methods described in other literatures, and methods similar thereto.

Scheme 8

[Chem.23]

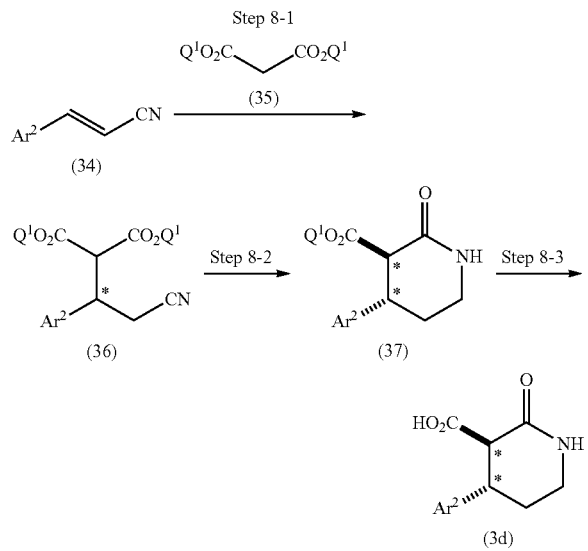

In the above formulas, $A^2$ and $Q^1$ are as described above, and each carbon atom marked with an asterisk is an asymmetric carbon atom.

Step 8-1

This step is a step of reacting Compound (34) and Compound (35) to produce Compound (36). Compound (36) can be produced by, for example, reacting Compound (34) with Compound (35) in a solvent in the presence of a base. Examples of the solvent used may include methanol, benzene, toluene, dimethylsulfoxide, N,N-dimethylformamide, mixed solvents thereof, and the like. Examples of the base used may include sodium methoxide and the like. The reaction temperature can generally be performed at 0° C. to the reflux temperature of the solvent and is performed preferably at 70° C. to 90° C. The reaction time varies depending on the starting materials used, the solvent used, the reaction temperature, or the like, but is generally 30 minutes to 3 days.

Further, Compound (34) and Compound (35) used in this step may be a commercially available, or can be produced in accordance with methods described in other literatures, and methods similar thereto.

Step 8-2

This step is a step of producing Compound (37) from Compound (36). Compound (37) can be produced by, for example, reacting Compound (36) in a solvent with sodium borohydride ($NaBH_4$) in the presence of nickel(II) chloride hexahydrate ($NiCl_2.6H_2O$). Examples of the solvent used may include methanol, ethanol, tetrahydrofuran, methyl tert-butyl ether, and the like. The reaction temperature can generally be performed at −30° C. to the reflux temperature of the solvent and is performed preferably at 0° C. to 80° C. The reaction time varies depending on the starting materials used, the solvent used, the reaction temperature, or the like, but is generally 30 minutes to 3 days.

Step 8-3

This step is a step of hydrolyzing the ester moiety of Compound (37) to produce Compound (3d). Compound (3d) can be produced in accordance with methods described at Step 5-2 in Scheme 5, methods similar thereto, methods described in other literatures, and methods similar thereto.

Synthesis of Compound (1)

Compound (1) can be produced, for example, from Compound (38) in accordance with methods described in Scheme 9, methods similar thereto, methods described in other literatures, and methods similar thereto.

Scheme 9

[Chem.24]

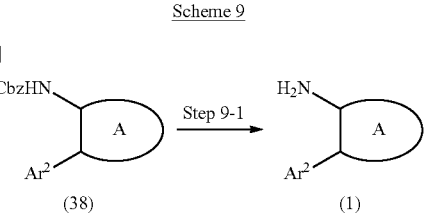

In the above formulas, $A^2$ and A are as described above, and each carbon atom marked with an asterisk is an asymmetric carbon atom.

Step 9-1

This step is a step of deprotecting the benzyloxycarbonyl (Cbz) group in Compound (38) to produce Compound (1). Compound (1) can be produced by, for example, hydrogenating Compound (38) in a solvent in the presence of a catalyst such as 10% palladium carbon (10% Pd—C). Examples of the solvent used may include methanol, ethanol, dichloromethane, tetrahydrofuran, ethyl acetate, acetic acid, mixed solvents thereof, and the like. The reaction temperature can generally be performed at −78° C. to the reflux temperature of the solvent and is performed preferably at 20° C. to 40° C. The reaction time varies depending on the starting materials used, the solvent used, the reaction temperature, or the like, but is generally 30 minutes to 3 days.

Synthesis of Compounds (38a, 38b, 38c)

Compound (38) of the present embodiment when A is a compound of the following formulae (38a, 38b, 38c) (this compound may hereinafter be referred to as Compounds (38a, 38b, 38c)) can be produced, for example, from Compound (39) in accordance with methods described in Scheme 10, methods similar thereto, methods described in other literatures, and methods similar thereto.

Scheme 10

[Chem.25]

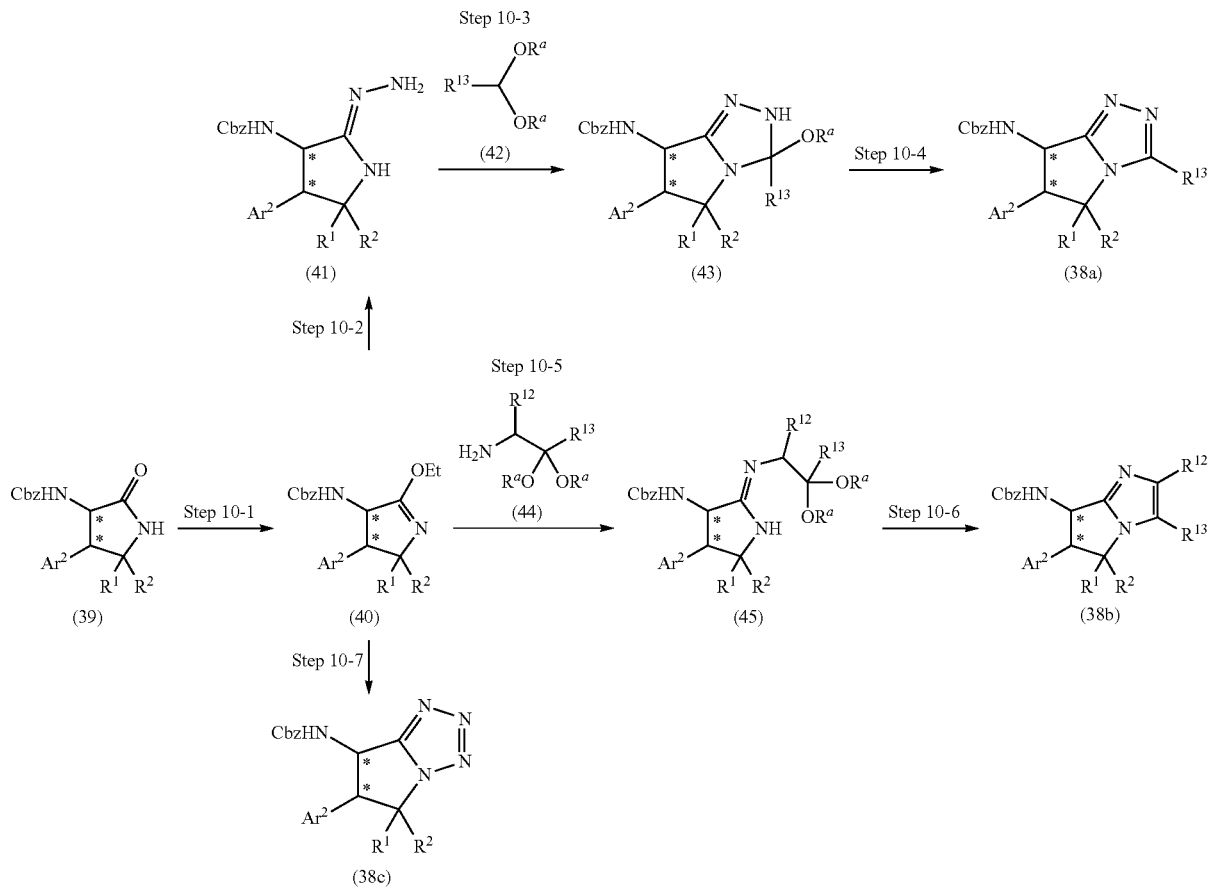

In the above formulas, Ar², R¹, R², R¹², and R¹³ are as described above; $R^a$ is a $C_1$ to $C_6$ alkyl group, and each carbon atom marked with an asterisk is an asymmetric carbon atom.

Step 10-1

This step is a step of producing Compound (40) from Compound (39). Compound (40) can be produced by, for example, reacting Compound (39) in a solvent with triethyloxonium hexafluorophosphate ($Et_3OPF_6$). Examples of the solvent used may include dichloromethane and the like. The reaction temperature can generally be performed at −78° C. to the reflux temperature of the solvent and is performed preferably at 20° C. to 40° C. The reaction time is generally 30 minutes to 3 days.

Step 10-2

This step is a step of producing Compound (41) from Compound (40). Compound (41) can be produced by, for example, reacting Compound (40) in a solvent with hydrazine monohydrate in the presence or absence of ammonium chloride. Examples of the solvent used may include ethanol and the like. The reaction temperature can generally be performed at 0° C. to the reflux temperature of the solvent and is performed preferably at 20° C. to 40° C. The reaction time is generally 30 minutes to 3 days.

Step 10-3

This step is a step of reacting Compound (41) and Compound (42) to produce Compound (43). Compound (43) can be produced by, for example, reacting Compound (41) in a solvent with Compound (42). Further, Compound (42) used in this step may be a commercially available, or can be produced in accordance with methods described in other literatures, and methods similar thereto. Examples of the solvent used may include ethanol and the like. The reaction temperature can generally be performed at 20° C. to the reflux temperature of the solvent and is performed preferably at 60° C. to 90° C. The reaction time is generally 30 minutes to 3 days.

Step 10-4

This step is a step of producing Compound (38a) from Compound (43). Compound (38a) can be produced by, for example, reacting Compound (43) in a solvent with an acid. Examples of the solvent used may include toluene and the like. Examples of the acid used may include hydrogen chloride, p-toluenesulfonic acid, and the like. The reaction temperature can generally be performed at 0° C. to the reflux temperature of the solvent and is performed preferably at 80° C. to 110° C. The reaction time is generally 30 minutes to 3 days.

Step 10-5

This step is a step of reacting Compound (40) and Compound (44) to produce Compound (45). Compound (45) can be produced by, for example, reacting Compound (40) in a solvent with Compound (44) in the presence or absence of an acid or a base. Further, Compound (44) may be a commercially available, or can be produced in accordance with methods described in other literatures, and methods similar thereto. Examples of the solvent used may include methanol, ethanol, toluene, tetrahydrofuran, acetonitrile, dioxane, mixed solvents thereof, and the like. Examples of the acid used may include hydrogen chloride, ammonium chloride, and the like. Examples of the base used may include trimethylamine, triethylamine, N-methylmorpholine, and the like. The reaction temperature can generally be performed at 0° C. to the reflux temperature of the solvent and is performed preferably at 20° C. to 40° C. The reaction time varies depending on the starting materials used, the solvent used, the reaction temperature, or the like, but is generally 10 minutes to 3 days.

Step 10-6

This step is a step of producing Compound (38b) from Compound (45). Compound (38b) can be produced by, for example, reacting Compound (45) in a solvent with an acid. Examples of the solvent used may include water and the like. Examples of the acid used may include hydrogen chloride and the like. The reaction temperature can generally be performed at 0° C. to the reflux temperature of the solvent and is performed preferably at 70° C. to 90° C. The reaction time is generally 30 minutes to 3 days.

Step 10-7

This step is a step of producing Compound (38c) from Compound (40). Compound (38c) can be produced by, for example, reacting Compound (40) in a solvent with sodium azide in the presence of acetic acid. Examples of the solvent used may include acetic acid and the like. The reaction temperature can generally be performed at 0° C. to the reflux temperature of the solvent and is performed preferably at 50° C. to 70° C. The reaction time is generally 30 minutes to 3 days.

Synthesis of Compounds (38d, 38e)

Compound (38) of the present embodiment when A is compounds of the following formulae (38d, 38e) (these compounds may hereinafter be referred to as Compounds (38d, 38e) can be produced, for example, from Compound (40) in accordance with methods described in Scheme 11, methods similar thereto, methods described in other literatures, and methods similar thereto.

Scheme 11

[Chem.26]

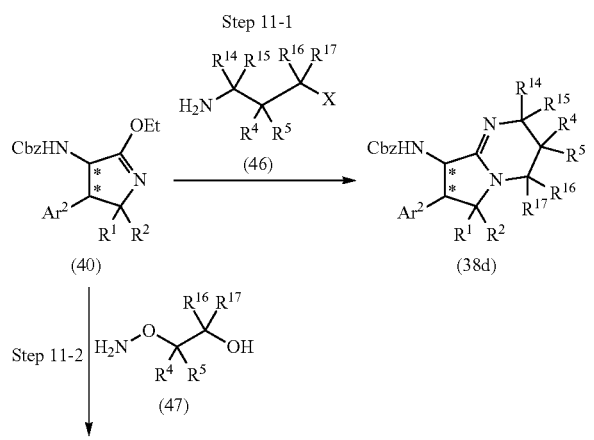

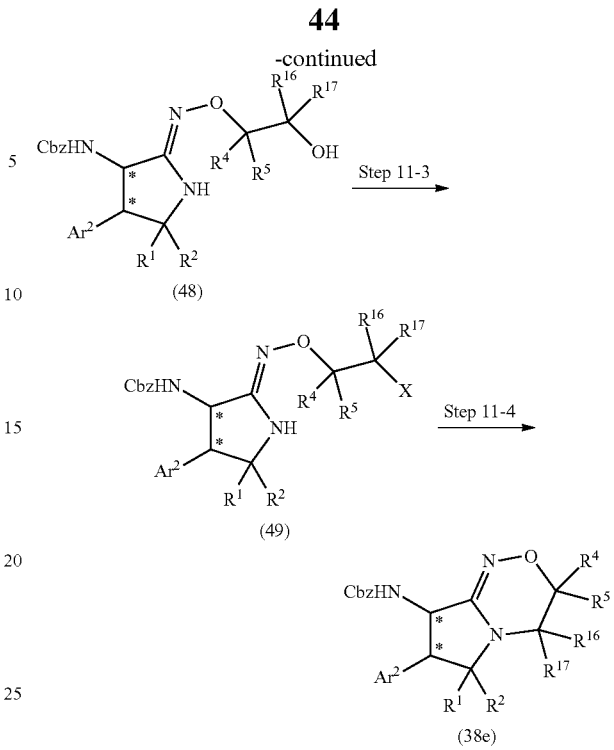

In the above formulas, $Ar^2$, $R^1$, $R^2$, $R^3$, $R^4$, $R^5$, $R^{14}$, $R^{15}$, $R^{16}$, and $R^{17}$ are as described above; X is a leaving group such as chlorine atom, bromine atom, iodine atom, methanesulfonyloxy group, trifluoromethanesulfonyloxy, and the like, and each carbon atom marked with an asterisk is an asymmetric carbon atom.

Step 11-1

This step is a step of reacting Compound (40) and Compound (46) to produce Compound (38d). Compound (38d) can be produced by, for example, reacting Compound (40) in a solvent with Compound (46) in the presence or absence of ammonium chloride, and then reacting the obtained product in the presence of potassium carbonate. Compound (46) may be a commercially available, or can be produced in accordance with methods described in other literatures, and methods similar thereto. Examples of the solvent used may include ethanol and the like. The reaction temperature can generally be performed at 20° C. to the reflux temperature of the solvent and is performed preferably at 10° C. to 40° C. The reaction time is generally 30 minutes to 3 days.

Step 11-2

This step is a step of reacting Compound (40) and Compound (47) to produce Compound (48). Compound (47) may be a commercially available, or can be produced in accordance with methods described in other literatures, and methods similar thereto. Compound (48) can be produced in accordance with methods described at Step 10-5 in Scheme 10, methods similar thereto, methods described in other literatures, and methods similar thereto.

Step 11-3

This step is a step of producing Compound (49) from Compound (48). Compound (49) wherein X is iodine atom can be produced by, for example, reacting Compound (48) in a solvent with iodine in the presence of imidazole, triphenylphosphine. Examples of the solvent used may include tetrahydrofuran and the like. The reaction temperature can generally be performed at 0° C. to the reflux temperature of the solvent and is performed preferably at 10° C. to 40° C. The reaction time is generally 30 minutes to 3 days.

Step 11-4

This step is a step of producing Compound (38e) from Compound (49). Compound (38e) can be produced by, for example, reacting Compound (49) in a solvent with a base. Examples of the solvent used may include N,N-dimethylformamide and the like. Examples of the base used may include potassium tert-butoxide and the like. The reaction temperature can generally be performed at 0° C. to the reflux temperature of the solvent and is performed preferably at 20° C. to 40° C. The reaction time is generally 30 minutes to 3 days.

Synthesis of Compound (Ia)

Compound (I) of the present embodiment when A is a compound of the following formula (Ia) (this compound may hereinafter be referred to as Compound (Ia)) can be produced, for example, from Compound (40) in accordance with methods described in Scheme 12, methods similar thereto, methods described in other literatures, and methods similar thereto.

10, methods similar thereto, methods described in other literatures, and methods similar thereto.

Step 12-2

This step is a step of deprotecting the Cbz group in Compound (51) to produce Compound (52). Compound (52) can be produced in accordance with methods described at Scheme 9, methods similar thereto, methods described in other literatures, and methods similar thereto.

Step 12-3

This step is a step of reacting Compound (52) and Compound (2) to produce Compound (53). Compound (53) can be produced in accordance with methods described at Step 1-1 in Scheme 1, methods similar thereto, methods described in other literatures, and methods similar thereto.

Step 12-4

This step is a step of producing Compound (Ia) from Compound (53). Compound (Ia) can be produced by, for example, reacting Compound (53) in a solvent with a base. Examples of the solvent used may include N,N-dimethylformamide and the like. Examples of the base used may include potassium carbonate, cesium carbonate, and the like. The reaction temperature can generally be performed at 0°

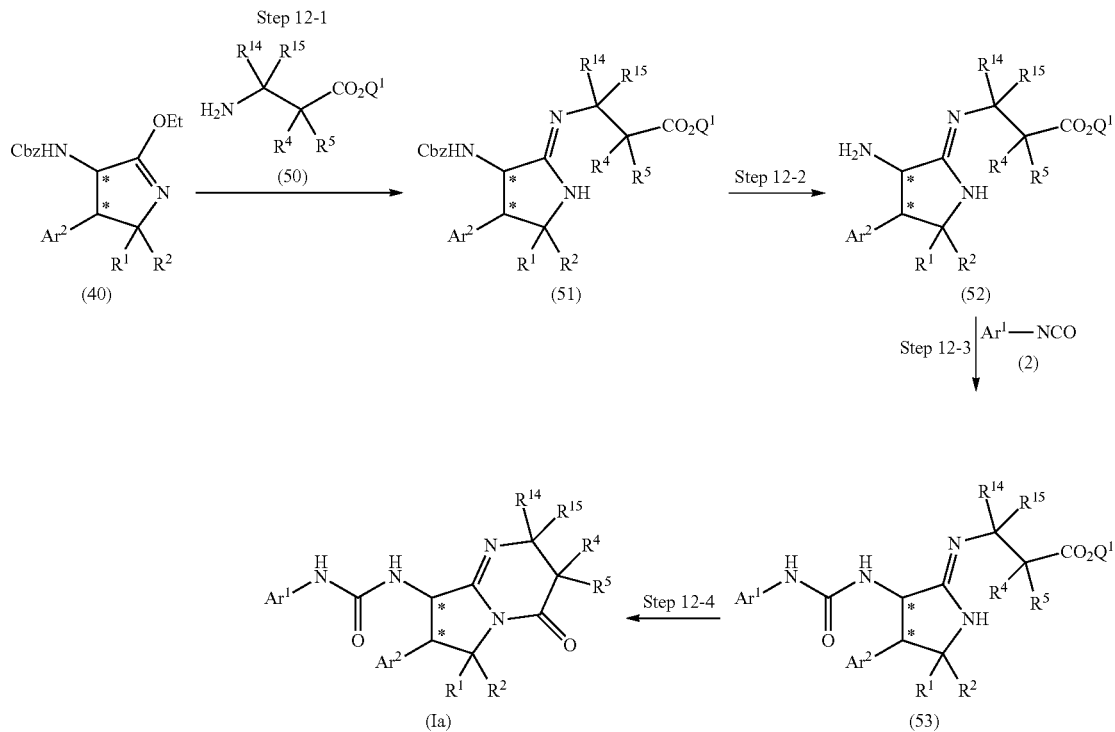

Scheme 12

[Chem.27]

In the above formulas, $Ar^1$, $Ar^2$, $R^1$, $R^2$, $R^4$, $R^5$, $R^{14}$, $R^{15}$, and $Q^1$ are as described above, and each carbon atom marked with an asterisk is an asymmetric carbon atom.

Step 12-1

This step is a step of reacting Compound (40) and Compound (50) to produce Compound (51). Compound (50) may be a commercially available, or can be produced in accordance with methods described in other literatures, and methods similar thereto. Compound (51) can be produced in accordance with methods described at Step 10-5 in Scheme C. to the reflux temperature of the solvent and is performed preferably at 20° C. to 40° C. The reaction time is generally 30 minutes to 3 days.

Synthesis of Compound (Ib)

Compound (I) of the present embodiment when A is a compound of the following formula (1b) (this compound may hereinafter be referred to as Compound (1b)) can be produced, for example, from Compound (40) in accordance with methods described in Scheme 13, methods similar thereto, methods described in other literatures, and methods similar thereto.

Scheme 13

[Chem.28]

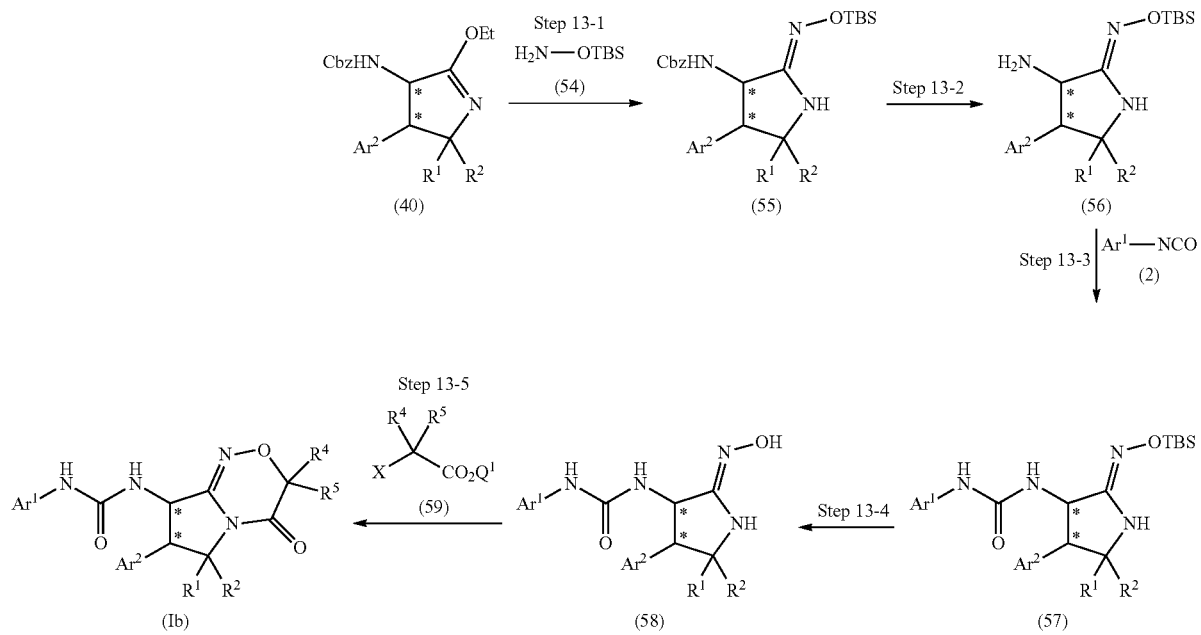

In the above formulas, $Ar^1$, $Ar^2$, $R^1$, $R^2$, $R^4$, $R^5$, $Q^1$, and X are as described above, and each carbon atom marked with an asterisk is an asymmetric carbon atom.

Step 13-1

This step is a step of reacting Compound (40) and Compound (54) to produce Compound (55). Compound (54) may be a commercially available, or can be produced in accordance with methods described in other literatures, and methods similar thereto. Compound (55) can be produced in accordance with methods described at Step 10-5 in Scheme 10, methods similar thereto, methods described in other literatures, and methods similar thereto.

Step 13-2

This step is a step of deprotecting the Cbz group in Compound (55) to produce Compound (56). Compound (56) can be produced in accordance with methods described at Scheme 9, methods similar thereto, methods described in other literatures, and methods similar thereto.

Step 13-3

This step is a step of reacting Compound (56) and Compound (2) to produce Compound (57). Compound (57) can be produced in accordance with methods described at Step 1-1 in Scheme 1, methods similar thereto, methods described in other literatures, and methods similar thereto.

Step 13-4

This step is a step of deprotecting the tert-butyldimethylsilyl (TBS) group in Compound (57) to produce Compound (58). Compound (58) can be produced by, for example, reacting Compound (57) in a mixed solvent of water-dioxane with an acid such as trifluoroacetic acid (TFA) and hydrogen chloride. The reaction temperature can generally be performed at −20° C. to the reflux temperature of the solvent and is performed preferably at 0° C. to 30° C. The reaction time varies depending on the starting materials used, the solvent used, the reaction temperature, or the like, but is generally 30 minutes to 3 days.

Step 13-5

This step is a step of reacting Compound (58) and Compound (59) to produce Compound (1b). Compound (1b) can be produced by, for example, reacting Compound (58) in a solvent with Compound (59) in the presence of a base. Compound (59) may be a commercially available, or can be produced in accordance with methods described in other literatures, and methods similar thereto. Examples of the solvent used may include N,N-dimethylformamide and the like. Examples of the base used may include potassium carbonate, cesium carbonate, and the like. The reaction temperature can generally be performed at 0° C. to the reflux temperature of the solvent and is performed preferably at 20° C. to 40° C. The reaction time is generally 30 minutes to 3 days.

Synthesis of Compound (Ib)

Compound (Ib) can be produced, for example, from Compound (40) in accordance with methods described in Scheme 14, methods similar thereto, methods described in other literatures, and methods similar thereto.

Scheme 14

[Chem. 29]

Step 14-1

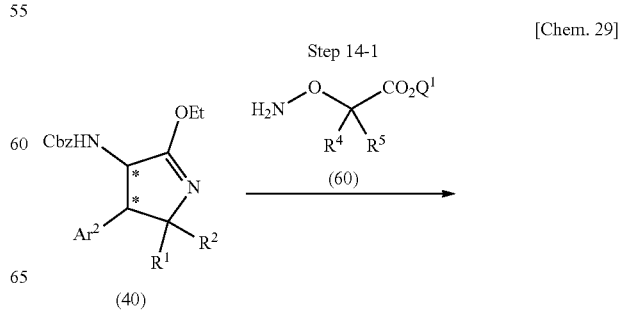

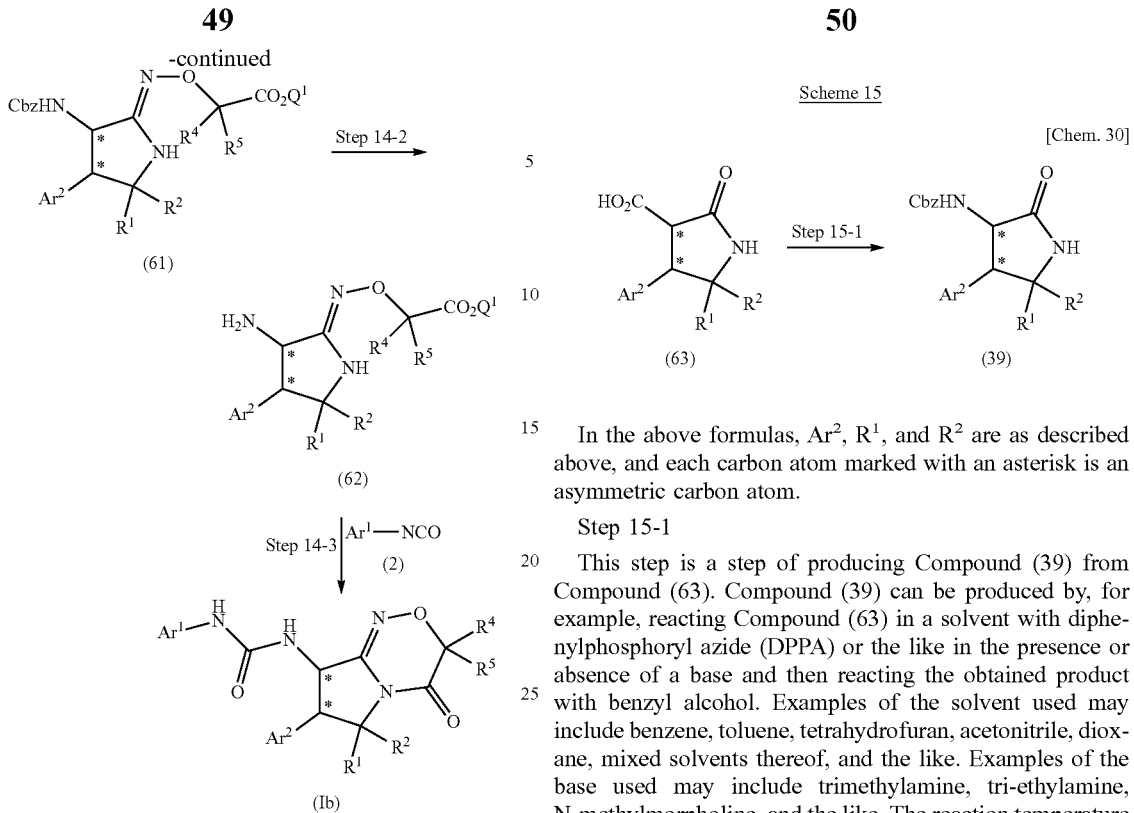

In the above formulas, $Ar^1$, $Ar^2$, $R^1$, $R^2$, $R^4$, $R^5$, and $Q^1$ are as described above, and each carbon atom marked with an asterisk is an asymmetric carbon atom.

Step 14-1

This step is a step of reacting Compound (40) and Compound (60) to produce Compound (61). Compound (60) may be a commercially available, or can be produced in accordance with methods described in other literatures, and methods similar thereto. Compound (61) can be produced in accordance with methods described at Step 10-5 in Scheme 10, methods similar thereto, methods described in other literatures, and methods similar thereto.

Step 14-2

This step is a step of deprotecting the Cbz group in Compound (61) to produce Compound (62). Compound (62) can be produced in accordance with methods described in Scheme 9, methods similar thereto, methods described in other literatures, and methods similar thereto.

Step 14-3

This step is a step of reacting Compound (62) and Compound (2) and simultaneously cyclizing them intramolecularly to produce Compound (Ib). Compound (Ib) can be produced in accordance with methods described at Step 1-1 in Scheme 1, methods similar thereto, methods described in other literatures, and methods similar thereto.

Synthesis of Compound (39)

Compound (39) can be produced, for example, from Compound (63) in accordance with methods described in Scheme 15, methods similar thereto, methods described in other literatures, and methods similar thereto.

Scheme 15

[Chem. 30]

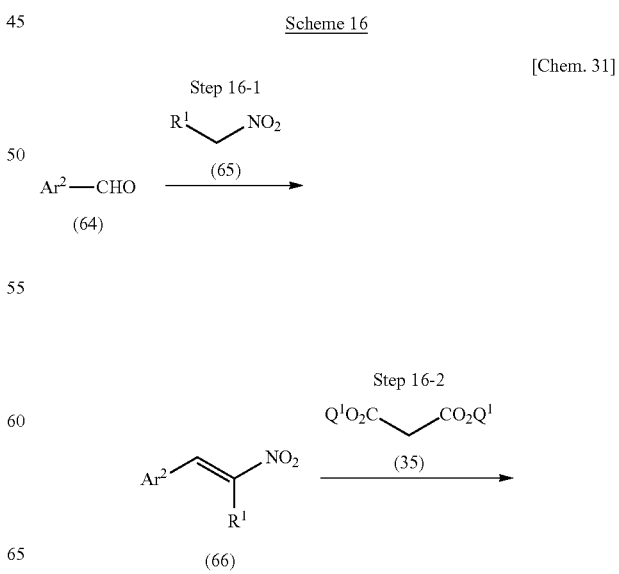

In the above formulas, $Ar^2$, $R^1$, and $R^2$ are as described above, and each carbon atom marked with an asterisk is an asymmetric carbon atom.

Step 15-1

This step is a step of producing Compound (39) from Compound (63). Compound (39) can be produced by, for example, reacting Compound (63) in a solvent with diphenylphosphoryl azide (DPPA) or the like in the presence or absence of a base and then reacting the obtained product with benzyl alcohol. Examples of the solvent used may include benzene, toluene, tetrahydrofuran, acetonitrile, dioxane, mixed solvents thereof, and the like. Examples of the base used may include trimethylamine, tri-ethylamine, N-methylmorpholine, and the like. The reaction temperature can generally be performed at 10° C. to the reflux temperature of the solvent and is performed preferably at 20° C. to 120° C. The reaction time varies depending on the starting materials used, the solvent used, the reaction temperature, or the like, but is generally 30 minutes to 3 days.

Synthesis of Compound (63a)

Among Compound (63) of the present embodiment, Compound (63a) wherein $R^2$ is H can be produced, for example, from Compound (64) in accordance with methods described in Scheme 16, methods similar thereto, methods described in other literatures, and methods similar thereto.

Scheme 16

[Chem. 31]

Step 16-1

$Ar^2$—CHO (64)

$R^1$\\/NO$_2$ (65)

Step 16-2

$Ar^2$\\=\\/NO$_2$ $R^1$ (66)

$Q^1O_2C$\\/\\CO$_2Q^1$ (35)

-continued

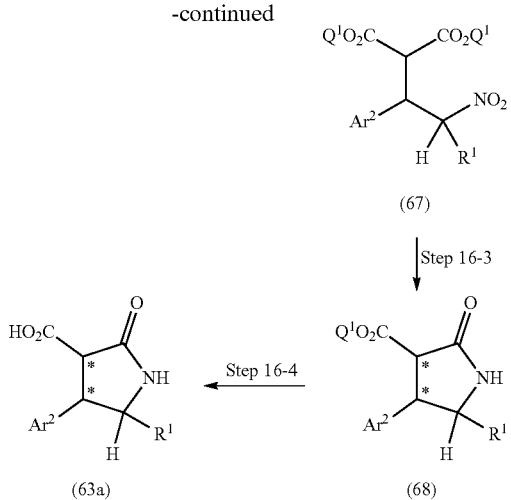

(67)

↓ Step 16-3

(63a) ← Step 16-4 ← (68)

In the above formulas, $Ar^2$, $R^1$, and $Q^1$ are as described above, and each carbon atom marked with an asterisk is an asymmetric carbon atom.

Step 16-1

This step is a step of reacting Compound (64) and Compound (65) to produce Compound (66). Compound (64) and Compound (65) may be a commercially available, or can be produced in accordance with methods described in other literatures, and methods similar thereto. Compound (66) can be produced by, for example, reacting Compound (64) in 2-hydroxyethyl ammonium formate (2-HEAF) with Compound (65). The reaction temperature can generally be performed at −78° C. to the reflux temperature of the solvent and is performed preferably at 20° C. to 40° C. The reaction time varies depending on the starting materials used, the solvent used, the reaction temperature, or the like, but is generally 30 minutes to 3 days.

Step 16-2

This step is a step of reacting Compound (66) and malonate (35) to produce Compound (67). Compound (67) can be produced by, for example, reacting Compound (66) in a solvent with Compound (35) in the presence of a catalyst. Examples of the solvent used may include benzene, toluene, tetrahydrofuran, methyl t-butyl ether, acetonitrile, methanol, ethanol, ethyl acetate, and the like. Examples of the catalyst may include nickel(II) bis[(S,S)—N,N'-dibenzylcyclohexane-1,2-diamine]bromide, nickel(II) bis[(R,R)—N,N-dibenzylcyclohexane-1,2-diamine]bromide, (±)-nickel(II) bis[N,N'-dibenzylcyclohexane-1,2-diamine]bromide, 1-(3,5-bis(trifluoromethyl)phenyl)-3-((1S,2S)-2-(dimethylamino)cyclohexyl)thiourea, 1-(3,5-bis(trifluoromethyl)phenyl)-3-((1R,2R)-2-(dimethylamino)cyclohexyl)thiourea, and the like, which can be prepared according to a method described in the Non-Patent Literatures. The amount of the catalyst is generally 0.001-0.2 molar equivalents per 1 mole of Compound (66). The reaction temperature can generally be performed at −78° C. to the reflux temperature of the solvent and is performed preferably at 20° C. to 40° C. The reaction time varies depending on the starting materials used, the solvent used, the reaction temperature, or the like, but is generally 30 minutes to 7 days.

Step 16-3

This step is a step of producing Compound (68) from Compound (67). Compound (68) can be produced by, for example, reacting Compound (67) in a solvent with sodium borohydride (NaBH$_4$) in the presence of nickel(II) chloride hexahydrate (NiCl$_2$.6H$_2$O). Examples of the solvent used may include methanol, ethanol, tetrahydrofuran, methyl t-butyl ether, and the like. The reaction temperature can generally be performed at −78° C. to the reflux temperature of the solvent and is performed preferably at 0° C. to 80° C. The reaction time varies depending on the starting materials used, the solvent used, the reaction temperature, or the like, but is generally 30 minutes to 3 days.

Step 16-4

This step is a step of hydrolyzing the ester moiety of Compound (68) to produce Compound (63a). Compound (63a) can be produced in accordance with methods described at Step 5-2 in Scheme 5, methods similar thereto, methods described in other literatures, and methods similar thereto.

Synthesis of Compound (63b)

Compound (63) wherein $R^1$ and $R^2$ are not H (this compound may hereinafter be referred to as Compound (63b)) can be produced, for example, from Compound (64) in accordance with methods described in Scheme 17, methods similar thereto, methods described in other literatures, and methods similar thereto.

Scheme 17

[Chem. 32]

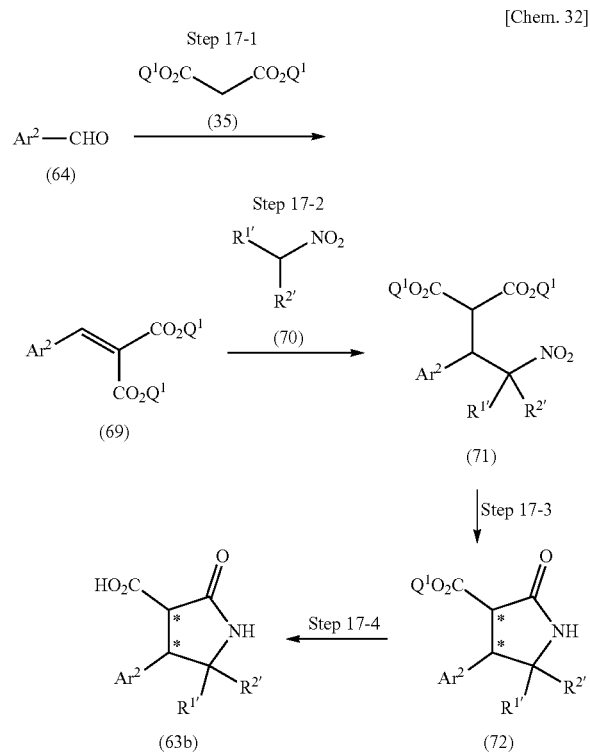

In the above formulas, $A^2$ and $Q^1$ are as described above, $R^{1'}$ and $R^{2'}$ are independently a $C_1$ to $C_6$ alkyl group optionally having substituent(S), or $R^{1'}$ and $R^{2'}$ together form a $C_2$ to $C_6$ alkylene group, and each carbon atom marked with an asterisk is an asymmetric carbon atom.

Step 17-1

This step is a step of reacting Compound (64) and Compound (35) to produce Compound (69). Compound (69) can be produced by, for example, reacting Compound (64) in a solvent with Compound (35) in the presence of a base.

Examples of the solvent used may include benzene, toluene, dimethylsulfoxide, N,N-dimethylformamide, mixed solvents thereof, and the like. Examples of the base used may include triethylamine, N-methylmorpholine, piperidine, pyridine, acetate thereof, and the like. The reaction temperature can generally be performed at −78° C. to the reflux temperature of the solvent and is performed preferably at 70° C. to 110° C. The reaction time varies depending on the starting materials used, the solvent used, the reaction temperature, or the like, but is generally 30 minutes to 3 days.

Step 17-2

This step is a step of reacting Compound (69) and Compound (70) to produce Compound (71). Compound (71) can be produced by, for example, reacting Compound (69) in a solvent with Compound (70) in the presence of a base. Examples of the solvent used may include toluene, benzene, tetrahydrofuran, acetonitrile, dimethylsulfoxide, N,N-dimethylformamide, mixed solvents thereof, and the like. Examples of the base used may include alumina-treated potassium fluoride (KF-Al$_2$O$_3$) and the like. The reaction temperature can generally be performed at −78° C. to the reflux temperature of the solvent and is performed preferably at 20° C. to 40° C. The reaction time varies depending on the starting materials used, the solvent used, the reaction temperature, or the like, but is generally 30 minutes to 3 days.

Step 17-3

This step is a step of producing Compound (72) from Compound (71). This step can be done according to the above Step 16-3.

Step 17-4

This step is a step of hydrolyzing the ester moiety of Compound (72) to produce Compound (63b). Compound (63b) can be produced in accordance with methods described at Step 5-2 in Scheme 5, methods similar thereto, methods described in other literatures, and methods similar thereto.

A pharmacologically acceptable salt of Compound (I) of the present embodiment can be produced using the compound (I) of the present embodiment according to a conventional method.

The schemes described above are examples of the method of producing Compound (I) of the present embodiment or a production intermediate thereof. These schemes can be modified to various schemes that can be readily understood by a person skilled in the art.

Also, in the case that there is a need of a protective group according to the kind of the functional group, an appropriate combination of introduction and removal procedures may be performed according to a conventional method. For the types of protective groups and introduction and removal of the protective groups, see, for example, methods described in "Greene's Protective Groups in Organic Synthesis," Theodra W. Green & Peter G. M. Wuts, ed., fourth edition, Wiley-Interscience, 2006.

The intermediates used for preparation of Compound (I) of the present embodiment or a pharmacologically acceptable salt thereof can be isolated/purified, as necessary, by solvent extraction, crystallization, recrystallization, chromatography, or preparative high-performance liquid chromatography or the like, that is an isolation/purification means well-known to a skilled person in the art.

The term "FPRL1 agonist effect" used in the present embodiment means that agonist activity exhibits through the action on formyl peptide receptor like 1 (FPRL1). As described above, it is known that LXA4 and peptides reported as endogenous agonists of FPRL1 contribute to resolution of inflammation.

Compound (I) of the present embodiment or a pharmacologically acceptable salt thereof exhibits superior agonist activity in, for example, a test of calcium influx into FPRL1-overexpressing cells. Therefore, Compound (I) of the present embodiment or a pharmacologically acceptable salt thereof is useful as a therapeutic or prophylactic agent for inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

Compound (I) of the present embodiment or a pharmacologically acceptable salt thereof can also be used to produce pharmaceuticals for treatment or prevention of inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

In addition, pharmaceuticals containing, as an active ingredient, Compound (I) of the present embodiment or a pharmacologically acceptable salt thereof can be used as, for example, prophylactic or therapeutic agents for various disease states associated with the FPRL1 receptor (such as Behcet's disease, Sweet disease, systemic lupus erythematosus (SLE), Wegener's granulomatosis, virus infection, diabetes, amputations, cancers, bacterial infection, physical external injuries, physical disorders including exposure to radiation, vasoconstriction, anaphylactic reactions, allergic reactions, rhinitis, shocks (endotoxic, hemorrhagic, traumatic, splanchnic ischemia, and circulatory shocks), rheumatoid arthritis, gout, psoriasis, benign prostatic hyperplasia, myocardial ischemia, myocardial infarction, brain injuries, pulmonary diseases, COPD, COAD, COLD, acute lung injury, acute respiratory distress syndrome, chronic bronchitis, pulmonary emphysema, asthma (allergic asthma and non-allergic asthma), cystic pulmonary fibrosis, nephropathy, renal glomerular diseases, ulcerative colitis, IBD, Crohn's disease, periodontitis, pains, Alzheimer's disease, AIDS, uveitic glaucoma, conjunctivitis, Sjoegren's syndrome, rhinitis and the like).

Pharmaceutical Containing Compound (I) of the Present Embodiment or Pharmacologically Acceptable Salt Thereof A pharmaceutical containing, as an active ingredient, Compound (I) of the present embodiment or a pharmacologically acceptable salt thereof can have various forms according to the usages. Examples of the forms may include powders, granules, fine granules, dry syrups, tablets, capsules, injections, liquids, ointments, suppositories, patches, sublingual tablets and the like, which are administered orally or parenterally.

Such a pharmaceutical can be formed as a pharmaceutical composition containing, as an active ingredient, Compound (I) of the present embodiment or a pharmacologically acceptable salt thereof and a pharmacologically acceptable additive using a well-known method according to the form of the pharmaceutical. Examples of the additive contained in the pharmaceutical composition may include an excipient, a disintegrant, a binder, a lubricant, a diluent, a buffering agent, an isotonizing agent, an antiseptic, a humectant, an emulsifier, a dispersant, a stabilizer, a solubilizing agent and the like. The pharmaceutical composition can be prepared by appropriately mixing Compound (I) of the present embodiment or a pharmacologically acceptable salt thereof with an additive or by diluting Compound (I) or a pharmacologically acceptable salt thereof with an additive and dissolving it in the additive. When Compound (I) of the present embodiment or a pharmacologically acceptable salt thereof is used in combination with agents other than the FPRL1 receptor agonist, a pharmaceutical composition can be produced by forming active ingredients of these components into a formulation simultaneously or separately in the manner described above.

The pharmaceutical according to the present embodiment can be systemically or locally administered orally or parenterally (transnasally, pulmonarily, intravenously, intrarectally, hypodermically, intramuscularly, percutaneously and the like).

When a pharmaceutical composition containing, as an active ingredient, Compound (I) of the present embodiment or a pharmacologically acceptable salt thereof is used for practical treatment, the dose of Compound (I) of the present embodiment or the pharmacologically acceptable salt thereof used as the active ingredient is appropriately determined according to the age, sex, and body weight of the patient, the disease of the patient, the degree of the treatment and the like. For example, in the case of oral administration, it may be appropriately administered to an adult (the body weight is assumed to be 60 kg) at a daily dose within the range of about 0.03 to about 1,000 mg/body in one portion or several divided portions. The dose per day as an oral administration is preferably 0.06 to 540 mg/body and more preferably 0.18 to 180 mg/body. In the case of parenteral administration, it may be appropriately administered to an adult at a daily dose within the range of about 0.01 to about 300 mg/body in one portion or several divided portions. The dose per day as a parenteral administration is preferably 0.01 to 100 mg/body and more preferably 0.06 to 60 mg/body. The dose of Compound (I) of the present embodiment or a pharmacologically acceptable salt thereof may be reduced according to the dose of agents other than the FPRL1 receptor agonist.

EXAMPLES

Hereinafter, the present invention will be described in more detail on the basis of Test Examples, Examples, and Reference Examples. Starting materials used in production of Compound (I) include a novel compound, and therefore Production examples for the starting materials will be also described as Reference Examples. The present invention is not limited to compounds described in the following Examples, and may be modified without departing from the scope of the present invention.

Among symbols used in each Reference Example, each Example, and each Table; Ref. No. represents Reference Example Number, Ex. No. represents Example Number, P.D. represents physical chemical data, Str. represents a structural formula, and $^1$H-NMR represents a proton nuclear magnetic resonance spectrum. CDCl$_3$ represents chloroform-d, and DMSO-d$_6$ represents dimethyl sulfoxide-d$_6$. MS(ESI$^+$) represents mass spectral data measured by electron-spray ionization. An optical rotation represents a specific optical rotation, which measured in described solvent at described concentration and temperature using sodium D-line as light source.

Wedge-shaped solid line and dashed line in a structural formula represent relative configuration in an optically active substance, but do not represent absolute configuration. Thick solid line and dashed line represent relative configuration in a racemate and an optically active substance obtained by resolution of a racemate. A carbon atom marked with "*" represents an asymmetric carbon. A wavy line bond of carbon atom marked with "*" represents the presence of a racemate.

Both R* and S* in the name of a compound represent relative steric configuration about an asymmetric carbon atom.

When both a substituent and a hydrogen atom are bonded to each of two positions of a pyrrolidine ring in a structural formula, the relative configuration of the substituents is expressed as cis or trans, and cis or trans is sometimes followed by a hyphen and the name of a compound.

When the pyrrolidine ring is considered as a face, cis means that the two adjacent substituents are on the same side, and trans means that the two adjacent substituents are on the respective opposite sides.

In order to represent isomers about a double bond and a double bond of imine in the name of a compound, a cis-isomer is expressed as "Z," and a trans-isomer is expressed as "E."

Reference Example 1-1

[Chem. 33]

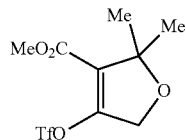

Methyl 2,2-dimethyl-4-{[(trifluoromethyl)sulfonyl]oxy}-2,5-dihydrofuran-3-carboxylate Under an argon atmosphere, to ice-cooled diethyl ether (43 mL) were added sodium hydride (746 mg) and then methyl 2,2-dimethyl-4-oxotetrahydrofuran-3-carboxylate (2.36 g), and the mixture was stirred for 30 minutes. Then, trifluoromethanesulfonic anhydride (2.83 mL) was added to the mixture to produce a reaction solution. The reaction solution was stirred under ice-cooling for 4 hours. To water was added the reaction solution, the mixture was extracted with dichloromethane, and the extract was dried over anhydrous sodium sulfate. The solvent was removed under reduced pressure, and the residue was then purified by silica gel column chromatography (hexane:ethyl acetate=20:1-1:1) to obtain the title compound as a colorless oil (3.43 g).

$^1$H NMR (400 MHz, CDCl$_3$) δ: 1.52 (6H, s), 3.84 (3H, s), 4.69 (2H, s).

Reference Example 1-2

[Chem. 34]

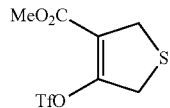

Methyl 4-{[(trifluoromethyl)sulfonyl]oxy}-2,5-dihydrothiophene-3-carboxylate

Using methyl 4-oxotetrahydrothiophene-3-carboxylate instead of methyl 2,2-dimethyl-4-oxotetrahydrofuran-3-carboxylate, the same method as in Reference Example 1-1 was performed to obtain the title compound.

$^1$H NMR (400 MHz, CDCl$_3$) δ: 3.83 (3H, s), 3.94-3.99 (4H, m).

Reference Example 2-1

[Chem. 35]

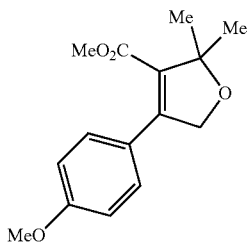

Methyl 4-(4-methoxyphenyl)-2,2-dimethyl-2,5-dihydrofuran-3-carboxylate

Under an argon atmosphere, to a solution of methyl 2,2-dimethyl-4-{[(trifluoromethyl)sulfonyl]oxy}-2,5-dihydrofuran-3-carboxylate (3.41 g) in N,N-dimethylformamide (62 mL) were added (4-methoxyphenyl)boronic acid (1.70 g), triethylamine (4.68 mL), and tetrakis(triphenylphosphine)palladium (386 mg) to produce a reaction solution. The reaction solution was stirred at 100° C. for 3 hours. 1 mol/L Hydrochloric acid was added to the reaction solution to make the reaction solution acidic (pH: 1), and the mixture was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=20:1-1:2) to obtain the title compound as a colorless oil (2.55 g).

$^1$H NMR (400 MHz, CDCl$_3$) δ: 1.53 (6H, s), 3.69 (3H, s), 3.83 (3H, s), 4.91 (2H, s), 6.89 (2H, d, J=9.1 Hz), 7.28 (2H, d, J=9.1 Hz).

The following Reference Examples 2-2 to 2-4 were obtained using each corresponding triflate and boronic acid in the same method as in Reference Example 2-1.

The structures and spectral data thereof are shown in Table 1.

TABLE 1

| Ref. No | Str. | Chemical name | P.D. |
|---|---|---|---|
| 2-2 | MeO$_2$C, phenyl-furan with MeO-C$_6$H$_4$ | methyl 4-(4-methoxyphenyl)-2,5-dihydrofuran-3-carboxylate | $^1$H-NMR (400 MHz, CDCl$_3$) δ: 3.72 (3H, s), 3.83 (3H, s), 4.99-5.09 (4H, m), 6.91 (2H, d, J = 9.1 Hz), 7.51 (2H, c, J = 9.1 Hz) |

TABLE 1-continued

| Ref. No | Str. | Chemical name | P.D. |
|---|---|---|---|
| 2-3 | MeO$_2$C, furan with 2,6-difluoro-4-methoxyphenyl | methyl 4-(2,6-difluoro-4-methoxyphenyl)-2,5-dihydrofuran-3-carboxylate | $^1$H-NMR (400 MHz, CDCl$_3$) δ: 3.69 (3H, s), 3.81 (3H, s), 4.94-4.98 (2H, m), 4.99-5.02 (2H, m), 6.49 (2H, d, J = 9.8 Hz) |
| 2-4 | MeO$_2$C, thiophene with 4-methoxyphenyl | methyl 4-(4-methoxyphenyl)-2,5-dihydrothiophene-3-carboxylate | $^1$H-NMR (400 MHz, CDCl$_3$) δ 3.62 (3H, s), 3.82 (3H, s), 4.11-4.18 (4H, m), 6.88 (2H, d, J = 9.1 Hz), 7.20 (2H, d, J = 9.1 Hz) |

Reference Example 3-1

[Chem. 36]

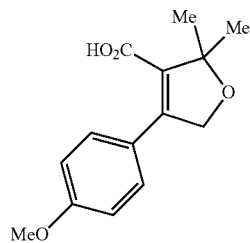

4-(4-Methoxyphenyl)-2,2-dimethyl-2,5-dihydrofuran-3-carboxylic acid

To a solution of methyl 4-(4-methoxyphenyl)-2,2-dimethyl-2,5-dihydrofuran-3-carboxylate (1.00 g) in methanol (7.6 mL) was added 2 mol/L aqueous potassium hydroxide (3.81 mL) to produce a reaction solution. The reaction solution was stirred at 50° C. for 4 hours. 1 mol/L hydrochloric acid was added to the reaction solution to make the reaction solution acidic (pH: 1), and the precipitated solid was collected by filtration and washed with water. The resulting solid was dried to obtain the title compound as a white solid (762 mg).

$^1$H NMR (400 MHz, DMSO-d$_6$) δ: 1.40 (6H, s), 3.76 (3H, s), 4.83 (2H, s), 6.92 (2H, d, J=9.1 Hz), 7.34 (2H, d, J=9.1 Hz), 12.64 (1H, s).

The following Reference Examples 3-2 to 3-3 were obtained using each corresponding ester in the same method as in Reference Example 3-1.

The structures and spectral data thereof are shown in Table 2.

TABLE 2

| Ref. No | Str. | Chemical name | P.D. |
|---|---|---|---|
| 3-2 | HO₂C, 4-methoxyphenyl structure with dihydrofuran | 4-(4-methoxyphenyl)-2,5-dihydrofuran-3-carboxylic acid | ¹H-NMR (400 MHz, DMSO-d₆) δ: 3.77 (3H, s), 4.85 (2H, t, J = 4.5 Hz), 5.00 (2H, t, J = 4.5 Hz), 6.93 (2H, dt, J = 8.5, 3.0 Hz), 7.54 (2H, dt, J = 8.5, 3.0 Hz), 12.65 (1H, s) |
| 3-3 | HO₂C, 2,6-difluoro-4-methoxyphenyl structure with dihydrofuran | 4-(2,6-difluoro-4-methoxyphenyl)-2,5-dihydrofuran-3-carboxylic acid | ¹H-NMR (400 MHz, DMSO-d₆) δ: 3.79 (3H, s), 4.84 (4H, s), 6.80 (2H, d, J = 9.8 Hz), 12.79 (1H, br s) |

Reference Example 4-1

[Chem. 37]

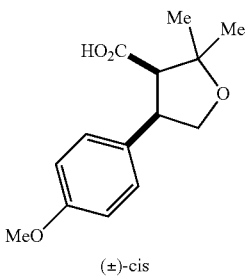

(±)-cis (±)-cis-4-(4-Methoxyphenyl)-2,2-dimethyltetrahydrofuran-3-carboxylic acid To a solution of 4-(4-methoxyphenyl)-2,2-dimethyl-2,5-dihydrofuran-3-carboxylic acid (750 mg) in ethanol (10 mL) was added 10% palladium carbon (75 mg), and the mixture was stirred under a hydrogen atmosphere for 3 hours. The reaction solution was filtered over Celite, and the solvent was removed. The resulting crude product was washed with diisopropyl ether to obtain the title compound as a white solid (618 mg).

¹H NMR (400 MHz, DMSO-d₆) δ: 1.26 (3H, s), 1.31 (3H, s), 3.06 (1H, d, J=7.3 Hz), 3.70 (3H, s), 3.87-3.96 (1H, m), 4.11 (1H, t, J=7.3 Hz), 4.28 (1H, dd, J=10.9, 7.3 Hz), 6.83 (2H, d, J=8.5 Hz), 7.11 (2H, d, J=8.5 Hz), 12.01 (1H, s).

The following Reference Examples 4-2 and 4-3 were obtained using each corresponding olefin in the same method as in Reference Example 4-1.

The structures and spectral data thereof are shown in Table 3.

TABLE 3

| Ref. No | Str. | Chemical name | P.D. |
|---|---|---|---|
| 4-2 | HO₂C, 4-methoxyphenyl tetrahydrofuran structure (±)-cis | (±)-cis-4-(4-methoxyphenyl)-tetrahydrofuran-3-carboxylic acid | ¹H-NMR (400 MHz, DMSO-d₆) δ: 3.37-3.44 (1H, m), 3.56-3.63 (1H m), 3.70 (3H, s), 3.87 (1H, dd, J = 3.5, 5.4 Hz), 3.95 (1H, t, J = 8.5 Hz), 3.99-4.05 (2H, m), 6.82 (2H, d, J = 8.5 Hz), 7.14 (2H, d, J = 8.5 Hz), 12.10 (1H, s) |
| 4-3 | HO₂C, 2,6-difluoro-4-methoxyphenyl tetrahydrofuran structure (±)-cis | (±)-cis-4-(2,6-difluoro-4-methoxyphenyl)-tetrahydrofuran-3-carboxylic acid | ¹H-NMR (400 MHz, DMSO-d₆) δ: 3.30-3.47 (1H, m), 3.74 (3H, s), 3.77-4.08 (4H, m), 4.11 (1H, t, J = 7.6 Hz), 6.67 (2H, d, J = 11.0 Hz), 12.14 (1H, br s) |

Reference Example 5-1

[Chem. 38]

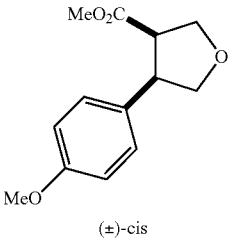

(±)-cis

Methyl (±)-cis-4-(4-methoxyphenyl)tetrahydrofuran-3-carboxylate

Using methyl 4-(4-methoxyphenyl)-2,5-dihydrofuran-3-carboxylate instead of 4-(4-methoxyphenyl)-2,2-dimethyl-2,5-dihydrofuran-3-carboxylic acid, the same method as in Reference Example 4-1 was performed to obtain the title compound.

¹H NMR (400 MHz, CDCl₃) δ: 3.34 (3H, s), 3.44-3.50 (1H, m), 3.66-3.71 (1H, m), 3.78 (3H, s), 4.07-4.17 (3H, m), 4.29 (1H, dd, J=9.1, 7.3 Hz), 6.82 (2H, dt, J=8.5, 1.8 Hz), 7.15 (2H, dt, J=8.5, 1.8 Hz).

Reference Example 6-1

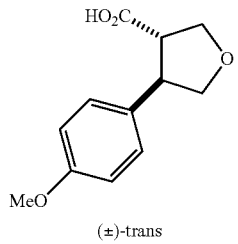

(±)-trans (±)-trans-4-(4-Methoxyphenyl)tetrahydrofuran-3-carboxylic acid

Under an argon atmosphere, to a solution of methyl (±)-cis-4-(4-methoxyphenyl)tetrahydrofuran-3-carboxylate (200 mg) in methanol (4.2 mL) was added sodium methoxide (20.0 mg) to produce a reaction solution. The reaction solution was stirred at room temperature for 18.5 hours. To the reaction solution was added 2 mol/L aqueous sodium hydroxide (0.847 mL), and the mixture was stirred at room temperature for 5 hours. 1 mol/L Hydrochloric acid was added to the reaction solution to make the reaction solution acidic (pH: 1), and the mixture was extracted with ethyl acetate. The organic layer was washed with water and then a brine, and dried over anhydrous sodium sulfate. The solvent was removed under reduced pressure to obtain the title compound as a colorless oil (182 mg).

$^1$H NMR (400 MHz, DMSO-$d_6$) δ: 3.04-3.13 (1H, m), 3.45-3.58 (2H, m), 3.71 (3H, s), 3.89 (1H, dd, J=8.2, 7.0 Hz), 4.06-4.14 (2H, m), 6.87 (2H, d, J=8.5 Hz), 7.21 (2H, d, J=8.5 Hz), 12.47 (1H, s).

Reference Example 7-1

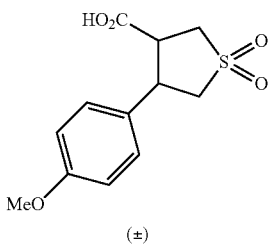

(±)

(±)-4-(4-Methoxyphenyl)tetrahydrothiophene-3-carboxylic acid 1,1-dioxide

Using methyl 4-(4-methoxyphenyl)-2,5-dihydrothiophene-3-carboxylate instead of 4-(4-methoxyphenyl)-2,2-dimethyl-2,5-dihydrofuran-3-carboxylic acid, the same method as in Reference Example 4-1 was performed to obtain a crude mixture of methyl (±)-cis-4-(4-methoxyphenyl)tetrahydrothiophene-3-carboxylate and methyl (±)-trans-4-(4-methoxyphenyl)tetrahydrothiophene-3-carboxylate (23 mg). To the solution of this crude mixture in dichloromethane (0.9 mL) was added metachloroperbenzoic acid (mCPBA) (49.4 mg), and the mixture was stirred at room temperature for 1 hour. To the reaction solution was added an aqueous sodium thiosulfate, and the mixture was extracted with ethyl acetate. The extract was washed with water and then a brine, and dried over anhydrous sodium sulfate. The solvent was removed under reduced pressure, and the residue was then purified by silica gel column chromatography (ethyl acetate:hexane=1:20-1:1) to obtain a mixture of methyl (±)-cis-4-(4-methoxyphenyl)tetrahydrothiophene-3-carboxylate 1,1-dioxide and (±)-trans-4-(4-methoxyphenyl)tetrahydrothiophene-3-carboxylic acid 1,1-dioxide. Using the obtained mixture of methyl (±)-cis-4-(4-methoxyphenyl)tetrahydrothiophene-3-carboxylate 1,1-dioxide and (±)-trans-4-(4-methoxyphenyl)tetrahydrothiophene-3-carboxylic acid 1,1-dioxide instead of methyl 4-(4-methoxyphenyl)-2,2-dimethyl-2,5-dihydrofuran-3-carboxylate, the same method as in Reference Example 3-1 was performed to obtain the title compound as a single racemic form.

$^1$H NMR (400 MHz, DMSO-$d_6$) δ: 3.21-3.29 (2H, m), 3.32-3.40 (1H, m), 3.52-3.70 (3H, m), 3.72 (3H, s), 6.88 (2H, d, J=8.5 Hz), 7.31 (2H, d, J=8.5 Hz), 12.77 (1H, s).

Reference Example 8-1

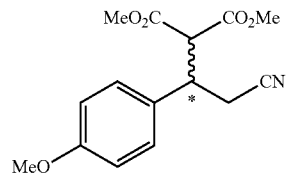

Dimethyl (±)-2-[2-cyano-1-(4-methoxyphenyl)ethyl]malonate

Under an argon atmosphere, to a solution of dimethyl malonate (4.57 mL) in methanol (20 mL) was added sodium methoxide (378 mg), and the mixture was stirred at room temperature for 10 minutes, and then 3-(4-methoxyphenyl)acrylonitrile (2.9 mL) was added to the reaction mixture to produce a reaction solution. The reaction solution was stirred at room temperature for 2 hours, and then heated to reflux for 18 hours. The reaction solution was allowed to cool to room temperature, and then 10% hydrochloric acid was added to the reaction solution. The mixture was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=2:1) to obtain the title compound as a white solid (2.96 g).

$^1$H-NMR (400 MHz, CDCl$_3$) δ: 2.84 (1H, dd, J=16.3, 4.8 Hz), 2.90 (1H, dd, J=16.3, 7.9 Hz), 3.54 (3H, s), 3.62-3.78 (1H, m), 3.80 (3H, s), 3.81 (3H, s), 3.86 (1H, d, J=9.1 Hz), 6.88 (2H, d, J=9.1 Hz), 7.21 (2H, d, J=9.1 Hz).

Reference Example 9-1

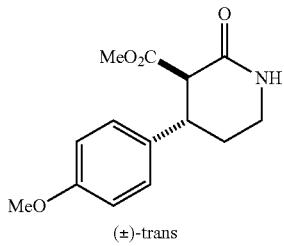

Methyl (±)-trans-4-(4-methoxyphenyl)-2-oxopiperidine-3-carboxylate

Under an argon atmosphere, to a solution of dimethyl (±)-2-[2-cyano-1-(4-methoxyphenyl)ethyl]malonate (291 mg) in methanol (10 mL) was added nickel(II) chloride hexahydrate (238 mg) to produce a reaction solution. To the reaction solution under ice-cooling was added sodium borohydride (227 mg) in several times, then the reaction mixture was warmed to room temperature and stirred for 1 hour. To the reaction solution were added a saturated aqueous ammonium chloride and ethyl acetate, and the mixture was stirred at room temperature for 1 hour. The reaction solution was extracted with ethyl acetate, and the extract was washed with water and then a brine, and then dried over anhydrous sodium sulfate. The solvent was removed under reduced pressure, and the residue was then purified by silica gel column chromatography (hexane:ethyl acetate=1:2) to obtain the title compound as a white solid (191 mg).

$^1$H NMR (400 MHz, DMSO-$d_6$) δ: 1.79 (1H, d, J=13.3 Hz), 1.90-2.02 (1H, m), 3.12-3.23 (2H, m), 3.24-3.30 (1H, m), 3.43 (3H, s), 3.51 (1H, d, J=11.5 Hz), 3.71 (3H, s), 6.84 (2H, d, J=8.5 Hz), 7.16 (2H, d, J=8.6 Hz), 7.87 (1H, d, J=2.4 Hz).

Reference Example 10-1

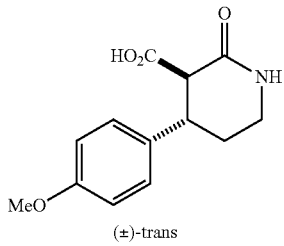

(±)-trans-4-(4-Methoxyphenyl)-2-oxopiperidine-3-carboxylic acid

To a solution of methyl (±)-trans-4-(4-methoxyphenyl)-2-oxopiperidine-3-carboxylate (345 mg) in methanol (2.6 mL) was added 1 mol/L aqueous sodium hydroxide (2.62 mL) to produce a reaction solution. The reaction solution was stirred at 50° C. for 1 hour. 1 mol/L Hydrochloric acid was added to the reaction solution to make the reaction solution acidic (pH: 1), and the mixture was extracted with ethyl acetate. The organic layer was washed with water and then a brine, and dried over anhydrous sodium sulfate. The solvent was removed under reduced pressure to obtain the title compound as a white solid (200 mg).

$^1$H NMR (400 MHz, DMSO-$d_6$) δ: 1.78 (1H, d, J=13.3 Hz), 1.90-2.02 (1H, m), 3.08-3.46 (4H, m), 3.71 (3H, s), 6.85 (2H, d, J=8.5 Hz), 7.18 (2H, d, J=8.6 Hz), 7.78 (1H, s), 12.17 (1H, s).

Reference Example 11-1

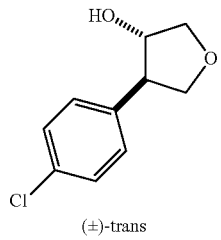

(±)-trans-4-(4-Chlorophenyl)tetrahydrofuran-3-ol

Under an argon atmosphere, to 1 mol/L 4-chlorophenylmagnesium bromide/diethyl ether (50 mL) under ice-cooling was added copper iodide(I) (476 mg) to produce a reaction solution. The reaction solution was stirred for 5 minutes, and a solution of 3,4-epoxytetrahydrofuran (4.30 g) in tetrahydrofuran (50 mL) was added to the reaction solution. The reaction mixture was stirred under ice-cooling for 10 minutes and at room temperature overnight. To the reaction solution was added a saturated aqueous ammonium chloride, and the mixture was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=6:1-ethyl acetate) to obtain the title compound as a colorless oil (4.19 g).

$^1$H NMR (400 MHz, CDCl$_3$) δ: 1.98 (1H, d, J=4.9 Hz), 3.26-3.32 (1H, m), 3.80 (1H, dd, J=9.8, 3.7 Hz), 3.90 (1H, dd, J=9.2, 5.5 Hz), 4.10 (1H, dd, J=9.8, 5.5 Hz), 4.33 (1H, dd, J=9.2, 7.3 Hz), 4.35-4.40 (1H, m), 7.20 (2H, d, J=8.6 Hz), 7.30 (2H, d, J=8.6 Hz).

The following Reference Examples 11-2 and 11-3 were obtained using each corresponding Grignard reagent and epoxy compound in the same method as in Reference Example 11-1.

The structures and spectral data thereof are shown in Table 4.

TABLE 4

| Ref No | Str. | Chemical name | P.D. |
|---|---|---|---|
| 11-2 | (structure: HO, 4-fluorophenyl-tetrahydrofuran-3-ol, (±)-trans) | (±)-trans-4-(4-fluorophenyl)-tetrahydrofuran-3-ol | $^1$H-NMR (400 MHz, CDCl$_3$) δ: 1.98 (1H, d, J = 4.2 Hz), 3.25-3.33 (1H, m), 3.80 (1H, dd, J = 9.7, 3.6 Hz), 3.90 (1H, dd, J = 9.1, 5.4 Hz), 4.08-4.13 (1H, m), 4.33 (1H, dd, J = 9.1, 7.3 Hz), 4.37 (1H, s), 7.02 (2H, t, J = 9.1 Hz), 7.22-7.24 (2H, m) |
| 11-3 | (structure: HO, THPO-phenyl-tetrahydrofuran-3-ol, (±)-trans) | (±)-trans-4-{4-[(tetrahydro-2H-pyran-2-yl)oxy]phenyl}tetrahydrofuran-3-ol | $^1$H-NMR (400 MHz, CDCl$_3$) δ: 1.61-1.76 (3H, m), 1.84-1.95 (3H, m), 1.98-2.08 (1H, m), 3.29 (1H, td, J = 6.7, 3.7 Hz), 3.59-3.67 (1H, m), 3.82 (1H, dd, J = 9.8, 3.1 Hz), 3.89-3.97 (2H, m), 4.12 (1H, ddd, J = 9.8, 4.9, 1.8 Hz), 4.34 (1H, dd, J = 8.6, 7.3 Hz), 4.37-4.42 (1H, m), 5.42 (1H, J = 3.4 Hz), 7.04 (2H, d, J = 8.6 Hz), 7.20 (2H, d, J = 8.6 Hz) |

Reference Example 12-1

[Chem. 45]

(±)-cis-2-[4-(4-Chlorophenyl)tetrahydrofuran-3-yl]isoindoline-1,3-dione

Under an argon atmosphere, to a solution of (±)-trans-4-(4-chlorophenyl)tetrahydrofuran-3-ol (4.00 g) in tetrahydrofuran (66 mL) under ice-cooling were added phthalimide (3.56 g) and triphenylphosphine (6.34 g) to produce a reaction solution. The reaction solution was stirred for 5 minutes, and then diisopropyl azodicarboxylate (4.67 mL) was added thereto. The reaction mixture was stirred under ice-cooling for 10 minutes, and then at room temperature overnight. Water was added to the reaction solution, and the mixture was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=4:1) to obtain the title compound as a white solid (4.33 g).

$^1$H NMR (400 MHz, CDCl$_3$) δ: 3.76 (1H, td, J=9.8, 7.3 Hz), 4.29-4.37 (2H, m), 4.51-4.61 (2H, m), 5.22 (1H, td, J=8.6, 5.5 Hz), 7.05-7.12 (4H, m), 7.63-7.67 (2H, m), 7.67-7.70 (2H, m).

The following Reference Examples 12-2 and 12-3 were obtained using each corresponding hydroxy compound in the same method as in Reference Example 12-1.

The structures and spectral data thereof are shown in Table 5.

TABLE 5

| Ref. No | Str. | Chemical name | P.D. |
|---|---|---|---|
| 12-2 | (structure: PhthN, 4-fluorophenyl-tetrahydrofuran, (±)-cis) | (±)-cis-2-[4-(4-fluorophenyl)tetrahydrofuran-3-yl]isoindoline-1,3-dione | $^1$H-NMR (400 MHz, DMSO-d$_6$) δ: 3.70-3.80 (1H, m), 4.26-4.35 (2H, m), 4.50-4.60 (2H, m), 5.18 (1H, td, J = 8.6, 5.5 Hz), 6.78 (2H, t, J = 7.9 Hz), 7.08-7.11 (2H, m), 7.58-7.68 (4H, m) |

TABLE 5-continued

| Ref. No | Str. | Chemical name | P.D. |
|---|---|---|---|
| 12-3 | PhthN, THPO, (±)-cis | (±)-cis-2-(4-{4-[(tetrahydro-2H-pyran-2-yl)oxy]-phenyl}tetra-hydrofuran-3-yl)isoindoline-1,3-dione | ¹H-NMR (400 MHz, CDCl₃) δ: 1.46-1.81 (5H, m), 1.84-1.96 (1H, m), 3.41-3.48 (1H, m), 3.67-3.79 (2H, m), 4.27-4.37 (2H, m), 4.52-4.60 (2H, m), 5.14-5.22 (2H, m), 6.79 (2H, d, J = 9.2 Hz), 7.04 (2H, d, J = 9.2 Hz), 7.59-7.64 (2H, m), 7.65-7.70 (2H, m) |

Reference Example 13-1

[Chem. 46]

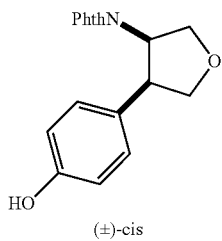

(±)-cis-2-[4-(4-Hydroxyphenyl)tetrahydrofuran-3-yl]isoindoline-1,3-dione

Under an argon atmosphere, to a solution of (±)-cis-2-(4-{4-[(tetrahydro-2H-pyran-2-yl)oxy] phenyl}tetrahydrofuran-3-yl)isoindoline-1,3-dione (3.22 g) in methanol (33 mL) under ice-cooling was added p-toluenesulfonic acid (1.56 g) to produce a reaction solution. The reaction solution was stirred at room temperature for 1 hour. Water was added to the reaction solution, and the mixture was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=1:1) to obtain the title compound as a white solid (2.38 g).

¹H NMR (400 MHz, CDCl₃) δ: 3.60-3.70 (1H, m), 4.13 (1H, t, J=7.6 Hz), 4.20 (1H, dd, J=9.5, 8.3 Hz), 4.28-4.36 (2H, m), 5.05 (1H, td, J=8.7, 4.7 Hz), 6.46 (2H, d, J=8.6 Hz), 6.84 (2H, d, J=8.6 Hz), 7.68-7.76 (4H, m), 9.10 (1H, s).

Reference Example 14-1

[Chem. 47]

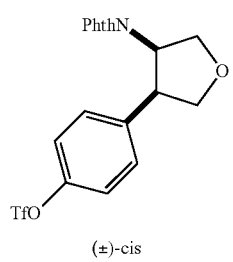

(±)-cis-2-{[4-(4-Trifluoromethanesulfonyloxy)phenyl]tetrahydrofuran-3-yl}isoindoline-1,3-dione Under an argon atmosphere, to a solution of (±)-cis-2-[4-(4-hydroxyphenyl)tetrahydrofuran-3-yl]isoindoline-1,3-dione (1.58 g) in dichloromethane (7.7 mL) under ice-cooling was added pyridine (4.12 mL) and a solution of trifluoromethanesulfonic anhydride (1.29 mL) in dichloromethane (2.6 mL) to produce a reaction solution. The reaction solution was stirred under ice-cooling for 2 hours. Water was added to the reaction solution, and the mixture was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=1:1) to obtain the title compound as a white solid (2.2 g).

¹H NMR (400 MHz, CDCl₃) δ: 3.76-3.87 (1H, m), 4.28-4.36 (2H, m), 4.56-4.63 (2H, m), 5.25 (1H, td, J=9.2, 5.5 Hz), 7.01 (2H, d, J=8.6 Hz), 7.23 (2H, d, J=8.6 Hz), 7.60-7.68 (4H, m).

Reference Example 15-1

[Chem. 48]

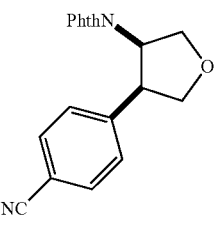

(±)-cis-4-[4-(1,3-Dioxoisoindolin-2-yl)tetrahydrofuran-3-yl]benzonitrile

Under an argon atmosphere, to a solution of (±)-cis-2-{[4-(4-trifluoromethanesulfonyloxy)phenyl]tetrahydrofuran-3-yl}isoindoline-1,3-dione (1.20 g) in N,N-dimethylformamide (10 mL) was added tetrakistriphenylphosphine palladium (316 mg) and zinc cyanide (1.27 g) to produce a reaction solution. The reaction solution was stirred at 100° C. for 3 hours. The reaction solution was filtered over Celite, and the filtrate was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=1:1) to obtain the title compound as a white solid (510 mg).

¹H NMR (400 MHz, CDCl₃) δ: 3.83 (1H, dd, J=16.5, 9.2 Hz), 4.30-4.37 (2H, m), 4.55 (1H, dd, J=9.2, 5.5 Hz), 4.63 (1H, t, J=9.2 Hz), 5.28 (1H, td, J=8.9, 5.7 Hz), 7.26 (2H, d, J=7.9 Hz), 7.42 (2H, d, J=7.9 Hz), 7.64-7.70 (4H, m).

Reference Example 16-1

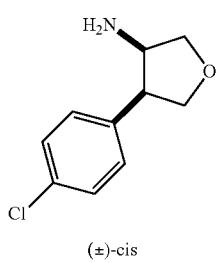

[Chem. 49]

(±)-cis (±)-cis-4-(4-Chlorophenyl)tetrahydrofuran-3-amine

Under an argon atmosphere, to a solution of (±)-cis-2-[4-(4-chlorophenyl)tetrahydrofuran-3-yl]isoindoline-1,3-dione (1.00 g) in ethanol (15 mL) was added hydrazine monohydrate (1.48 mL) to produce a reaction solution. The reaction solution was heated to reflux for 3 hours. Water was added to the reaction solution under ice-cooling, and the mixture was extracted with ethyl acetate. The organic layer was washed with water and then a brine, and dried over anhydrous sodium sulfate. The solvent was removed under reduced pressure to obtain the title compound as a colorless oil (608 mg).

¹H NMR (400 MHz, CDCl₃) δ: 3.42 (1H, q, J=6.7 Hz), 3.62 (1H, dd, J=9.1, 4.2 Hz), 3.78 (1H, td, J=6.1, 4.8 Hz), 4.08-4.22 (3H, m), 7.20 (2H, d, J=8.5 Hz), 7.33 (2H, d, J=8.5 Hz).

The following Reference Examples 16-2 and 16-3 were obtained using each corresponding phthaloyl compound in the same method as in Reference Example 16-1.

The structures and spectral data thereof are shown in Table 6.

TABLE 6

| Ref. No | Str. | Chemical name | P.D. |
|---|---|---|---|
| 16-2 | H₂N, tetrahydrofuran with 4-fluorophenyl, (±)-cis | (±)-cis-4-(4-fluorophenyl)-tetrahydrofuran-3-amine | ¹H-NMR (400 MHz, CDCl₃) δ: 3.43 (1H, q, J = 6.7 Hz), 3.60-3.66 (1H, m), 3.77 (1H, q, J = 5.5 Hz), 4.08-4.22 (3H, m), 7.03-7.08 (2H, m), 7.20-7.25 (2H, m) |
| 16-3 | H₂N, tetrahydrofuran with 4-cyanophenyl, (±)-cis | (±)-cis-4-(4-aminotetrahydrofuran-3-yl)benzonitrile | ¹H-NMR (400 MHz, CDCl₃) δ: 3.48 (1H, q, J = 6.7 Hz), 3.62 (1H, dd, J = 8.6, 4.3 Hz), 3.86 (1H, dd, J = 10.4, 5.5 Hz), 4.11-4.24 (3H, m), 7.40 (2H, d, J = 8.6 Hz), 7.66 (2H, d, J = 8.6 Hz) |

Reference Example 17-1

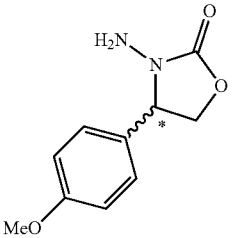

[Chem. 50]

(±)-3-Amino-4-(4-methoxyphenyl)oxazolidin-2-one

Under an argon atmosphere, to a solution of 4-(4-methoxyphenyl)oxazolidin-2-one (300 mg) in dioxane (8 mL) was added sodium hydride (65 mg) to produce a reaction solution. The reaction solution was stirred at 60° C. for 1 hour. O-(4-Nitrobenzoyl)hydroxylamine (311 mg) was added to the reaction solution, and the reaction mixture was stirred at room temperature for 2 hours. A saturated aqueous ammonium chloride was added to the reaction solution, and the mixture was extracted with ethyl acetate. The organic layer was washed with a brine, and dried over anhydrous sodium sulfate. The solvent was removed under reduced pressure, and the residue was then purified by silica gel column chromatography (hexane:ethyl acetate=1:4) to obtain the title compound as a white solid (194 mg).

¹H NMR (400 MHz, DMSO-d₆) δ: 3.74 (3H, s), 3.95 (1H, dd, J=8.5, 6.7 Hz), 4.61 (1H, t, J=8.5 Hz), 4.86 (1H, dd, 8.5, 6.7 Hz), 6.94 (2H, d, J=9.1), 7.25 (2H, d, J=9.2), 8.09 (2H, s).

Reference Example 18-1

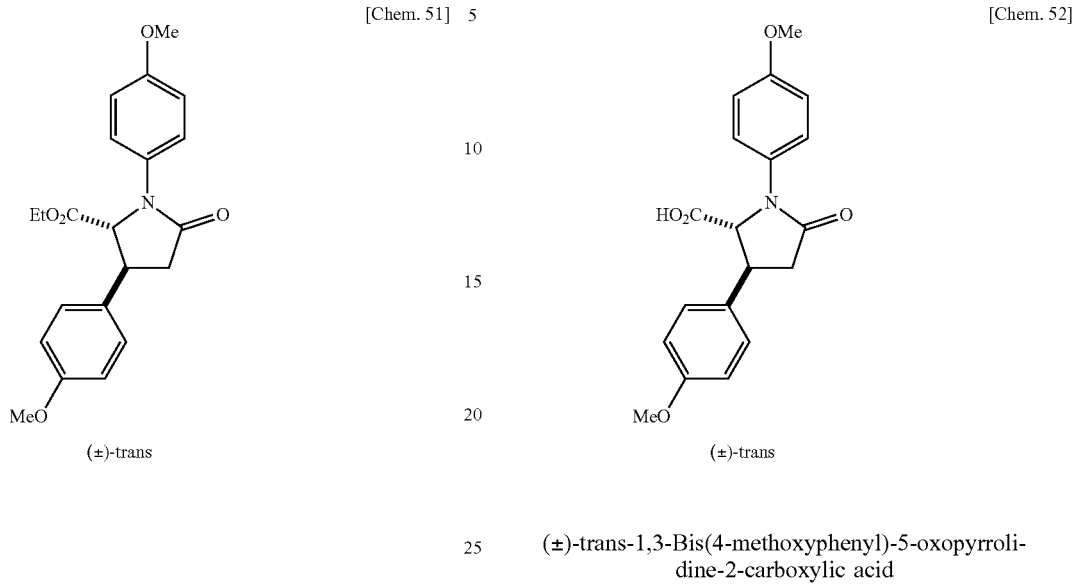

Ethyl (±)-trans-1,3-bis(4-methoxyphenyl)-5-oxopyrrolidine-2-carboxylate

To ethanol (7 mL) was added sodium (172 mg), and the mixture was stirred for 15 minutes. Then, a solution of dimethyl 2-[(4-methoxyphenyl)amino]malonate (2.0 g) in ethanol (35 mL) was added to the mixture at room temperature to produce a reaction solution. The reaction solution was stirred for 15 minutes. To the reaction solution was added ethyl 4-methoxycinnamate (2.20 g), and the reaction mixture was refluxed for 16 hours. To the reaction solution under ice-cooling was added acetic acid (1.0 mL), and the mixture was concentrated under reduced pressure. Water was added to the obtained residue, and the mixture was extracted with ethyl acetate. The organic layer was washed with a brine, and dried over anhydrous sodium sulfate. The solvent was removed under reduced pressure. To the obtained residue were added dimethyl-sulfoxide (7.0 mL), water (0.26 mL), and then sodium chloride (420 mg), and the mixture was refluxed for 2 hours. The reaction solution was allowed to cool to room temperature, iced water was added thereto, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=2:1) to obtain the title compound as a white solid (633 mg).

$^1$H-NMR (400 MHz, CDCl$_3$) δ: 1.20 (3H, t, J=7.0 Hz), 2.69 (1H, dd, J=17.0, 4.2 Hz), 3.15 (1H, dd, J=17.0, 9.1 Hz), 3.54-3.60 (1H, m), 3.79 (3H, s), 3.81 (3H, s), 4.14-4.24 (2H, m), 4.54 (1H, d, J=3.6 Hz), 6.86-6.92 (4H, m), 7.22 (2H, d, J=11.5 Hz), 7.32 (2H, d, J=9.1 Hz).

Reference Example 19-1

(±)-trans-1,3-Bis(4-methoxyphenyl)-5-oxopyrrolidine-2-carboxylic acid

To a solution of ethyl (±)-trans-1,3-bis(4-methoxyphenyl)-5-oxopyrrolidine-2-carboxylate (570 mg) in methanol (7.7 mL) at room temperature was added 2 mol/L aqueous sodium hydroxide (1.5 mL) to produce a reaction solution. The reaction solution was stirred at room temperature for 4 days. The reaction solution was concentrated under reduced pressure, and then water and 2 mol/L hydrochloric acid were added to the residue to make the solution acidic (pH: 1). The precipitated solid was collected by filtration, washed with water, and dried to obtain the title compound as a white solid (516 mg).

$^1$H NMR (400 MHz, DMSO-d$_6$) δ:2.53 (1H, dd, J=17.0, 6.7 Hz), 2.95 (1H, dd, J=17.0, 9.1 Hz), 3.54-3.62 (1H, m), 3.73 (3H, s), 3.73 (3H, s), 4.64 (1H, d, J=4.8 Hz), 6.88-6.94 (4H, m), 7.28 (2H, d, J=9.1 Hz), 7.36 (2H, d, J=9.1 Hz), 13.11 (1H, br s).

Reference Example 20-1

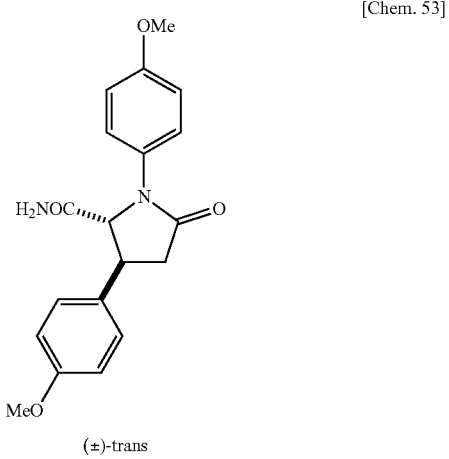 [SMILES: COc1ccc([C@@H]2CC(=O)N(c3ccc(OC)cc3)[C@H]2C(N)=O)cc1]

(±)-trans-1,3-Bis(4-methoxyphenyl)-5-oxopyrrolidine-2-carboxamide

To a solution of (±)-trans-1,3-bis(4-methoxyphenyl)-5-oxopyrrolidine-2-carboxylic acid (155 mg) in anhydrous N,N-dimethylformamide (7.4 mL) were added 1-hydroxybenzotriazole (245 mg) and 1-ethyl-3-(3-dimethylaminopropyl)carbodiimide (308 mg) to produce a reaction solution. The reaction solution was stirred at room temperature for 1 hour. Then, aqueous ammonia (1.1 mL) was added to the reaction solution, and the reaction mixture was stirred at room temperature for 2 days. Water was added to the reaction solution, and the mixture was extracted with ethyl acetate. The organic layer was washed with a brine, and dried over anhydrous sodium sulfate. The solvent was removed under reduced pressure, and the obtained residue was then purified by silica gel column chromatography (ethyl acetate:methanol=20:1) to obtain the title compound as a white solid (408 mg).

$^1$H-NMR (400 MHz, CDCl$_3$) δ: 2.71 (1H, dd, J=17.0, 5.5 Hz), 3.15 (1H, dd, J=17.0, 9.1 Hz), 3.60-3.70 (1H, m), 3.79 (3H, s), 3.81 (3H, s), 4.45 (1H, d, J=3.6 Hz), 5.42 (1H, br s), 5.64 (1H, br s), 6.87-6.93 (4H, m), 7.23 (2H, d, J=9.1 Hz), 7.39 (2H, d, J=9.1 Hz).

Reference Example 21-1

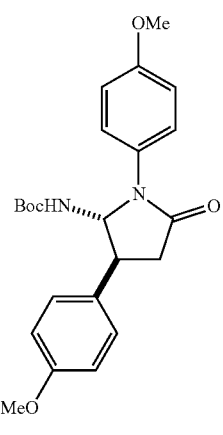

[Chem. 54]

(±)-trans tert-Butyl (±)-trans-(1,3-bis(4-methoxyphenyl)-5-oxopyrrolidine-2-yl)carbamate To a solution of (±)-trans-1,3-bis(4-methoxyphenyl)-5-oxopyrrolidine-2-carboxamide (155 mg) in tert-butanol (1.2 mL) was added pyridine (1.2 mL) at room temperature and then [bis(trifluoroacetoxy)iodo]benzene (293 mg) at room temperature to produce a reaction solution. The reaction solution was stirred at 90° C. for 4 hours. The reaction solution was allowed to cool to room temperature, iced water was added thereto, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=9:1-1:1) to obtain the title compound as a white solid (94 mg).

$^1$H-NMR (400 MHz, CDCl$_3$) δ: 1.30 (9H, s), 2.70 (1H, dd, J=17.1, 7.9 Hz), 3.07 (1H, dd, J=17.1, 8.6 Hz), 3.30-3.39 (1H, m), 3.79 (3H, s), 3.82 (3H, s), 4.80-4.94 (1H, m), 5.60-5.73 (1H, m), 6.90 (4H, d, J=7.9 Hz), 7.22-7.33 (4H, m).

Reference Example 22-1

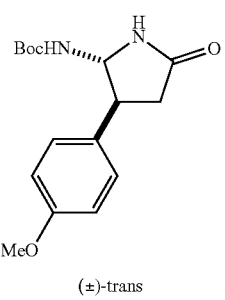

[Chem. 55]

(±)-trans tert-Butyl (±)-trans-[3-(4-methoxyphenyl)-5-oxopyrrolidin-2-yl]carbamate

To a solution of tert-butyl (±)-trans-(1,3-bis(4-methoxyphenyl)-5-oxopyrrolidin-2-yl)carbamate (71.0 mg) in acetonitrile (3.5 mL) under ice-cooling was added a solution of ammonium cerium(IV) nitrate (189 mg) in water (3.5 mL) to produce a reaction solution. The reaction solution was stirred under ice-cooling for 3 hours. Water was added to the reaction solution, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=6:1-3:1) to obtain the title compound as a white solid (29 mg).

$^1$H-NMR (400 MHz, CDCl$_3$) δ: 1.43 (9H, s), 2.49 (1H, dd, J=17.1, 7.9 Hz), 2.84 (1H, dd, J=17.7, 9.2 Hz), 3.20 (1H, td, J=7.9, 6.4 Hz), 3.80 (3H, s), 4.97-5.11 (1H, m), 5.19-5.29 (1H, m), 6.06-6.21 (1H, m), 6.89 (2H, d, J=8.6 Hz), 7.18 (2H, d, J=8.6 Hz).

Reference Example 23-1

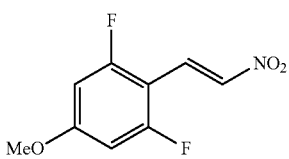

[Chem. 56]

(E)-1,3-Difluoro-5-methoxy-2-(2-nitrovinyl)benzene

Under an argon atmosphere, to a solution of 2,6-difluoro-4-methoxybenzaldehyde (14.7 g) in acetic acid (85 mL) were added ammonium acetate (11.2 g) and nitromethane (22.9 mL) to produce a reaction solution. The reaction solution was stirred at 100° C. for 6 hours. The reaction solution was concentrated under reduced pressure, water was added thereto, and the precipitated solid was collected by filtration and washed with water. The resulting solid was dried to obtain the title compound as a yellow solid (17.5 g).

$^1$H NMR (400 MHz, CDCl$_3$) δ: 3.87 (3H, s), 6.54-6.59 (2H, m), 7.77 (1H, d, J=13.4 Hz), 8.11 (1H, d, J=13.4 Hz).

Reference Example 23-2

[Chem. 57]

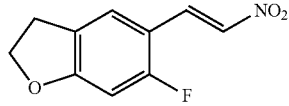

(E)-6-Fluoro-5-(2-nitrovinyl)-2,3-dihydrobenzofuran

Using 6-fluoro-2,3-dihydrobenzofuran-5-carbaldehyde instead of 2,6-difluoro-4-methoxybenzaldehyde, the same method as in Reference Example 23-1 was performed to obtain the title compound.

$^1$H NMR (400 MHz, CDCl$_3$) δ 3.23 (2H, t, J=8.9 Hz), 4.72 (2H, t, J=8.9 Hz), 6.60 (1H, d, J=11.6 Hz) 7.30 (1H, d, J=6.7 Hz), 7.62 (1H, d, J=13.4 Hz), 8.03 (1H, d, J=13.4 Hz).

Reference Example 24-1

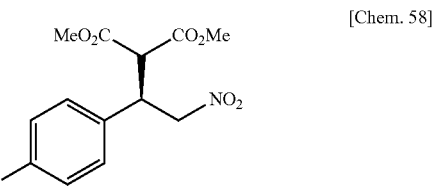

[Chem. 58]

Dimethyl (−)-(R*)-2-[1-(4-methoxyphenyl)-2-nitro-ethyl]malonate

Under an argon atmosphere, to a solution of (E)-1-methoxy-4-(2-nitrovinyl)benzene (500 mg) in toluene (2.8 mL) were added dimethyl malonate (0.36 mL) and nickel(II) bis[(S,S)—N,N'-dibenzylcyclohexane-1,2-diamine]bromide (68 mg) to produce a reaction solution. The reaction solution was stirred at room temperature for 6 hours. The solvent was removed under reduced pressure, and the obtained residue was then purified by silica gel column chromatography (ethyl acetate:hexane=4:1) to obtain the title compound as a colorless liquid (865 mg).

$^1$H-NMR (400 MHz, CDCl$_3$) δ: 3.57 (3H, s), 3.76 (3H, s), 3.78 (3H, s), 3.83 (1H, d, J=9.1 Hz), 4.16-4.22 (1H, m), 4.83 (1H, dd, J=12.7, 9.1 Hz), 4.89 (1H, dd, J=12.7, 5.1 Hz), 6.84 (2H, d, J=9.1 Hz), 7.14 (2H, d, J=9.1 Hz).

$[α]_D^{25}$ −20 (c 0.26, EtOH)

The following Reference Examples 24-2 and 24-3 were obtained using each corresponding nitrostyrene in the same method as in Reference Example 24-1.

The structures and spectral data thereof are shown in Table 7.

TABLE 7

| Ref. No | Str. | Chemical name | P.D. |
|---|---|---|---|
| 24-2 | (structure) | dimethyl (−)-(R*)-2-[1-(2,6-difluoro-4-methoxyphenyl)-2-nitroethyl]-malonate | $^1$H-NMR (400 MHz, CDCl$_3$) δ: 3.57 (3H, s), 3.77 (3H, s), 3.80 (3H, s), 3.93 (1H, d, J = 10.4 Hz), 4.63-4.70 (1H, m), 4.81 (1H, dd, J = 13.1, 10.1 Hz), 4.91 (1H, dd, J = 13.1, 4.7 Hz), 6.41-6.47 (2H, m) $[α]_D^{24}$ −25 (c 0.11, EtOH) |
| 24-3 | (structure) | dimethyl (−)-(R*)-2-[1-(6-fluoro-2,3-dihydro-benzofuran-5-yl)-2-nitroethyl]-malonate | $^1$H-NMR (400 MHz, CDCl$_3$) δ: 3.13 (2H, t, J = 8.9 Hz), 3.58 (3H, s), 3.77 (3H, s), 3.96 (1H, d, J = 9.8 Hz), 4.29-4.35 (1H, m), 4.59 (2H, t, J = 8.9 Hz), 4.87 (2H, d, J = 7.3 Hz), 6.48 (1H, d, J = 11.6 Hz), 6.99 (1H, d, J = 7.3 Hz) $[α]_D^{26}$ −20 (c 0.31, EtOH) |

Reference Example 25-1

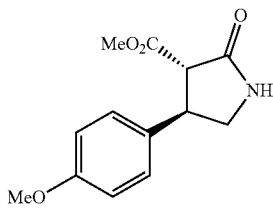

Methyl (−)-(3S*,4R*)-4-(4-methoxyphenyl)-2-oxopyrrolidine-3-carboxylate

Under an argon atmosphere, to a solution of dimethyl (R*)-2-[1-(4-methoxyphenyl)-2-nitroethyl]malonate (1.7 g) in methanol (110 mL) was added nickel(II) chloride hexahydrate (1.3 g) to produce a reaction solution. To the reaction solution under ice-cooling was added sodium borohydride (1.03 g) in several times, and then the reaction mixture was warmed to room temperatureand stirred for 2 hours. To the reaction solution were added a saturated aqueous ammonium chloride and ethyl acetate, and the mixture was stirred at room temperature for 1 hour. The reaction solution was extracted with ethyl acetate, the organic layer was washed with water and then a brine, and dried over anhydrous sodium sulfate. The solvent was removed under reduced pressure, and then the resulting crude product was washed with ethanol-diisopropyl ether to obtain the title compound as a white solid (840 mg).

[Chem. 59]

$^1$H-NMR (400 MHz, CDCl$_3$) δ: 3.40 (1H, t, J=9.1 Hz), 3.53 (1H, d, J=9.7 Hz), 3.76-3.81 (1H, m), 3.78 (3H, s), 3.80 (3H, s), 4.08 (1H, q, J=8.9 Hz), 5.85 (1H, brs), 6.88 (2H, d, J=8.5 Hz), 7.18 (2H, d, J=8.5 Hz).

$[α]_D^{25}$ −96 (c 0.19, EtOH)

The following Reference Examples 25-2 and 25-3 were obtained using each corresponding nitro compound in the same method as in Reference Example 25-1.

The structures and spectral data thereof are shown in Table 8.

TABLE 8

| Ref. No | Str. | Chemical name | P.D. |
|---|---|---|---|
| 25-2 | | methyl (−)-(3S*,4R*)-4-(2,6-difluoro-4-methoxyphenyl)-2-oxopyrrolidine-3-carboxylate | $^1$H-NMR (400 MHz, CDCl$_3$) δ: 3.51 (1H, t, J = 9.2 Hz), 3.64-3.70 (1H, m), 3.78 (6H, s), 3.78-3.81 (1H, m), 4.46 (1H, q, J = 9.4 Hz), 6.24 (1H, brs), 6.43-6.50 (2H, m) $[α]_D^{23}$ −120 (c 0.11, EtOH) |
| 25-3 | | methyl (−)-(3S*,4R*)-4-(6-fluoro-2,3-dihydrobenzofuran-5-yl)-2-oxopyrrolidine-3-carboxylate | $^1$H-NMR (400 MHz, CDCl$_3$) δ: 3.15 (2H, t, J = 8.9 Hz), 3.41 (1H, t, J = 8.6 Hz), 3.66 (1H, d, J = 9.8 Hz), 3.74-3.79 (1H, m), 3.79 (3H, s), 4.19 (1H, q, J = 8.6 Hz), 4.61 (2H, t, J = 8.9 Hz), 5.68 (1H, brs), 6.52 (1H, d, J = 11.6 Hz), 7.03 (1H, d, J = 7.9 Hz) $[α]_D^{26}$ −121 (c 0.20, EtOH) |

Reference Example 26-1

[Chem. 60]

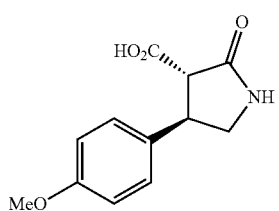

(−)-(3S*,4R*)-4-(4-Methoxyphenyl)-2-oxopyrrolidine-3-carboxylic acid

To a solution of methyl (−)-(3S*,4R*-4-(4-methoxyphenyl)-2-oxopyrrolidine-3-carboxylate (130 mg) in methanol (2.6 mL) was added 2 mol/L aqueous sodium hydroxide (0.52 mL) to produce a reaction solution. The reaction solution was stirred at 60° C. for 1 hour. 1 mol/L Hydrochloric acid was added to the reaction solution to make the reaction solution acidic (pH: 1), and the mixture was extracted with ethyl acetate. The organic layer was washed with water and then a brine, and dried over anhydrous sodium sulfate. The solvent was removed under reduced pressure, and then the resulting crude product was washed with ethyl acetate-diisopropyl ether to obtain the title compound as a white solid (112 mg).

$^1$H-NMR (400 MHz, DMSO-d$_6$) δ: 3.16 (1H, t, J=9.4 Hz), 3.42 (1H, d, J=10.9 Hz), 3.55 (1H, t, J=8.2 Hz), 3.72 (3H, s), 3.79 (1H, q, J=9.5 Hz), 6.88 (2H, d, J=8.5 Hz), 7.24 (2H, d, J=8.5 Hz), 8.03 (1H, s), 12.54 (1H, brs).

[α]$_D^{27}$ −68 (c 0.15, EtOH)

The following Reference Examples 26-2 and 26-3 were obtained using each corresponding ester in the same method as in Reference Example 26-1.

The structures and spectral data thereof are shown in Table 9.

Reference Example 27-1

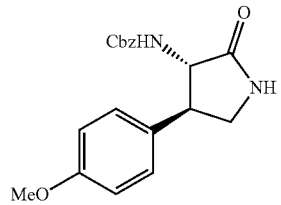

[Chem. 61]

Benzyl (−)-[(3S*,4R*)-4-(4-methoxyphenyl)-2-oxopyrrolidin-3-yl]carbamate

To a solution of (−)-(3S*,4R*)-4-(4-methoxyphenyl)-2-oxopyrrolidine-3-carboxylic acid (6.04 g) in toluene (128 mL) were added triethylamine (3.95 mL) and diphenylphosphoryl azide (6.2 mL) to produce a reaction solution. The reaction solution was stirred at room temperature for 4.5 hours. The reaction solution was heated to 80° C., and stirred for 30 minutes. Then, benzyl alcohol (13.3 mL) was added to the reaction solution, and the reaction mixture was stirred at 120° C. for 5 hours. The reaction solution was concen-

TABLE 9

| Ref. No | Str. | Chemical name | P.D. |
|---|---|---|---|
| 26-2 | ![structure] | (−)-(3S*,4R*)-4-(2,6-difluoro-4-methoxyphenyl)-2-oxopyrrolidine-3-carboxylic acid | $^1$H-NMR (400 MHz, DMSO-d$_6$) δ: 3.25 (1H, t, J = 9.2 Hz), 3.43 (1H, d, J = 10.4 Hz), 3.56 (1H, t, J = 9.2 Hz), 3.76 (3H, s), 4.14 (1H, q, J = 9.4 Hz), 6.73-6.80 (2H, m), 8.20 (1H, s), 12.77 (1H, brs) [α]$_D^{23}$ −121 (c 0.10, EtOH) |
| 26-3 | ![structure] | (−)-(3S*,4R*)-4-(6-fluoro-2,3-dihydrobenzofuran-5-yl)-2-oxopyrrolidine-3-carboxylic acid | $^1$H-NMR (400 MHz, DMSO-d$_6$) δ: 3.09-3.19 (3H, m), 3.46 (1H, d. J = 10.4 Hz), 3.52 (1H, t, J = 8.9 Hz), 3.94-4.03 (1H, m), 4.55 (2H, t, J = 8.6 Hz), 6.65 (1H, d, J = 11.0 Hz), 7.31 (1H, d, J = 7.9 Hz), 8.09 (1H, s), 12.65 (1H, brs) [α]$_D^{27}$ −114 (c 0.30, EtOH) | trated under reduced pressure, and the residue was then purified by silica gel column chromatography (ethyl acetate-ethyl acetate:methanol=10:1) to obtain the title compound as a white solid (6.3 g).

$^1$H-NMR (400 MHz, CDCl$_3$) δ: 3.36 (1H, t, J=9.1 Hz), 3.49-3.70 (2H, m), 3.80 (3H, s), 4.42 (1H, dd, J=11.5, 8.5 Hz), 5.07 (2H, s), 5.16 (1H, brs), 5.98 (1H, brs), 6.89 (2H, d, J=7.9 Hz), 7.22 (2H, d, J=7.9 Hz), 7.20-7.40 (5H, m).

$[α]_D^{27}$ −79 (c 0.17, EtOH)

The following Reference Examples 27-2 and 27-3 were obtained using each corresponding carboxylic acid in the same method as in Reference Example 27-1.

The structures and spectral data thereof are shown in Table 10.

30 minutes. The mixture was extracted with dichloromethane. The organic layer was dried over anhydrous sodium sulfate. The solvent was removed under reduced pressure to obtain benzyl [(3S*,4R*)-5-ethoxy-3-(2,6-difluoro-4-methoxyphenyl)-3,4-dihydro-2H-pyrrol-4-yl]carbamate that is an intermediate as a yellow oil. To a solution of benzyl [(3R*,4S*)-5-ethoxy-3-(2,6-difluoro-4-methoxyphenyl)-3,4-dihydro-2H-pyrrol-4-yl]carbamate (40 mg) in ethanol (0.7 mL) were added ammonium chloride (0.5 mg) and hydrazine monohydrate (23 μL) to produce a reaction solution. The reaction solution was stirred at room temperature for 18 hours. The reaction solution was concentrated under reduced pressure, and the obtained residue was dissolved in ethanol (0.8 mL). To the ethanol solution was added ethyl orthoac-

TABLE 10

| Ref. No | Str. | Chemical name | P.D. |
|---|---|---|---|
| 27-2 | ![structure] | benzyl (−)-[(3S*,4R*)-4-(2,6-difluoro-4-methoxyphenyl)-2-oxopyrrolidine-3-yl]carbamate | $^1$H-NMR (400 MHz, CDCl$_3$) δ: 3.48-3.62 (2H, m), 3.79 (3H, s), 3.80-3.96 (1H, m), 4.67-4.75 (1H, m), 5.05 (2H, s), 5.38 (1H, brd, J = 8.0 Hz), 6.42-6.53 (2H, m), 6.60 (1H, s), 7.26-7.36 (5H, m) $[α]_D^{24}$ −107 (c 0.10, EtOH) |
| 27-3 | ![structure] | benzyl (−)-[(3S*,4R*)-4-(6-fluoro-2,3-dihydrobenzofuran-5-yl)-2-oxopyrrolidine-3-yl]carbamate | $^1$H-NMR (400 MHz, CDCl$_3$) δ: 3.05-3.25 (2H, m), 3.37 (1H, t, J = 9.2 Hz), 3.55-3.80 (2H, m), 4.50-4.65 (3H, m), 5.04-5.14 (3H, m), 5.83 (1H, s), 6.50 (1H, d, J = 10.4 Hz), 7.10-7.22 (1H, m), 7.26-7.40 (5H, m) $[α]_D^{29}$ −185 (c 0.16, EtOH) |

Reference Example 28-1

[Chem. 62]

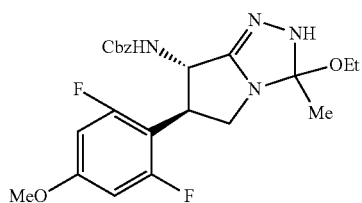

Benzyl [(6R*,7S*)-6-(2,6-difluoro-4-methoxyphenyl)-3-ethoxy-3-methyl-3,5,6,7-tetrahydro-2H-pyrrolo[2,1-c][1,2,4]triazol-7-yl]carbamate To a suspension of benzyl (−)-[(3S*,4R*)-4-(2,6-difluoro-4-methoxyphenyl)-2-oxopyrrolidin-3-yl]carbamate (605 mg) in dichloromethane (8 mL) was added triethyloxonium hexafluorophosphate (595 mg) to produce a reaction solution. The reaction solution was stirred at room temperature for 20 hours. A saturated aqueous sodium hydrogen carbonate solution was added to the reaction solution, and the mixture was stirred at room temperature for etate (28 μL), and the mixture was heated to reflux for 3 hours. The solvent was removed under reduced pressure, and the residue was then purified by silica gel column chromatography (ethyl acetate:hexane=1:1) to obtain the title compound as a colorless oil (27 mg).

$^1$H NMR (400 MHz, CDCl$_3$) δ: 1.30 (3H, t, J=7.3 Hz), 2.06 (3H, s), 3.52-3.72 (3H, m), 3.77 (3H, s), 4.12 (2H, q, J=7.3 Hz), 5.02 (2H, s), 5.09 (1H, dd, J=10.4, 7.3 Hz), 5.24 (1H, s), 5.62 (1H, s), 6.40-6.49 (2H, m), 7.30 (5H, s).

Reference Example 29-1

[Chem. 63]

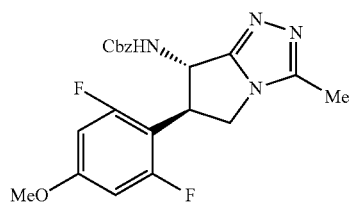

Benzyl [(6R*,7S*)-6-(2,6-difluoro-4-methoxyphenyl)-3-methyl-6,7-dihydro-5H-pyrrolo[2,1-c][1,2,4]triazol-7-yl]carbamate To a solution of benzyl [(6R*,7S*)-6-(2,6-difluoro-4-methoxyphenyl)-3-ethoxy-3-methyl-3,5,6,7-tetrahydro-2H-pyrrolo[2,1-c][1,2,4]triazol-7-yl]carbamate (27 mg) in toluene (1 mL) was added p-toluenesulfonic acid (1 mg) to produce a reaction solution. The reaction solution was heated to reflux for 5 hours. The reaction solution was concentrated under reduced pressure, and the obtained residue was then purified by silica gel column chromatography (ethyl acetate:methanol=4:1) to obtain the title compound as a colorless oil (10 mg).

$^1$H NMR (400 MHz, CDCl$_3$) δ: 2.45 (3H, s), 3.81 (3H, s), 3.98-4.09 (1H, m), 4.17-4.30 (1H, m), 4.40-4.50 (1H, m), 5.00-5.13 (2H, m), 5.39-5.48 (2H, m), 6.52 (2H, d, J=10.4 Hz), 7.29-7.39 (5H, m).

Reference Example 30-1

[Chem. 64]

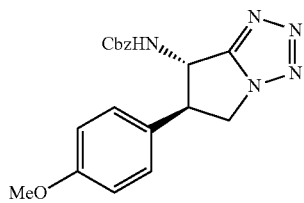 [SMILES: COc1cc(F)c([C@@H]2Cn3nnnc3[C@H]2NC(=O)OCc2ccccc2)c(F)c1]

Benzyl [(6R*,7S*)-6-(4-methoxyphenyl)-6,7-dihydro-5H-pyrrolo[1,2-d]tetrazol-7-yl]carbamate To a suspension of benzyl (−)-[(3S*,4R*)-4-(4-methoxyphenyl)-2-oxopyrrolidin-3-yl]carbamate (500 mg) in dichloromethane (3.7 mL) was added triethyloxonium hexafluorophosphate (446 mg) to produce a reaction solution. The reaction solution was stirred at room temperature for 20 hours. A saturated aqueous sodium hydrogen carbonate solution was added to the reaction solution, and the mixture was stirred at room temperature for 30 minutes. The mixture was extracted with dichloromethane. The organic layer was dried over anhydrous sodium sulfate. The solvent was removed under reduced pressure to obtain benzyl [(3R*,4S*)-5-ethoxy-3-(4-methoxyphenyl)-3,4-dihydro-2H-pyrrol-4-yl]carbamate that is an intermediate as a yellow oil. To a solution of benzyl [(3R*,4S*)-5-ethoxy-3-(4-methoxyphenyl)-3,4-dihydro-2H-pyrrol-4-yl]carbamate (325 mg) in acetic acid (1.2 mL) was added sodium azide (177 mg) to produce a reaction solution. The reaction solution was stirred at 60° C. for 5 hours. To the reaction solution under ice-cooling were added ethyl acetate and aqueous potassium carbonate to make the reaction solution basic (pH: 9), and the mixture was extracted with ethyl acetate. The organic layer was washed with water and a brine and dried over anhydrous sodium sulfate. The solvent was removed under reduced pressure, and the residue was then purified by silica gel column chromatography (hexane:ethyl acetate=1:1) to obtain the title compound as a colorless oil (160 mg).

$^1$H-NMR (400 MHz, DMSO-d$_6$) δ: 3.75 (3H, s), 4.21-4.36 (2H, m), 4.89 (1H, dd, J=9.7, 7.9 Hz), 5.00 (1H, d, J=12.7 Hz), 5.05 (1H, d, J=12.7 Hz), 5.34 (1H, m), 6.94 (2H, d, J=8.5 Hz), 7.25-7.38 (5H, m), 7.42 (2H, d, J=8.5 Hz), 8.14 (1H, d, J=9.1 Hz).

The following Reference Examples 30-2 and 30-3 were obtained using each corresponding Cbz compound in the same method as in Reference Example 30-1.

The structures and spectral data thereof are shown in Table 11.

TABLE 11

| Ref. No | Str. | Chemical name | P.D. |
|---|---|---|---|
| 30-2 | | benzyl [(6R*,7S*)-6-(2,6-difluoro-4-methoxyphenyl)-6,7-dihydro-5H-pyrrolo[1,2-d]tetrazol-7-yl]carbamate | $^1$H-NMR (400 MHz, CDCl$_3$) δ: 3.81 (3H, s), 4.36-4.46 (1H, m), 4.67-4.76 (1H, m), 4.76-4.84 (1H, m), 5.03-5.13 (2H, m), 5.36 (1H, t, J = 7.3 Hz), 5.45 (1H, br s), 6.53 (2H, d, J = 10.4 Hz), 7.27-7.38 (5H, m) |
| 30-3 | | benzyl [(6R*,7S*)-6-(6-fluoro-2,3-dihydrobenzofuran-5-yl)-6,7-dihydro-5H-pyrrolo[1,2-d]tetrazol-7-yl]carbamate | $^1$H-NMR (400 MHz, CDCl$_3$) δ: 3.17 (2H, t, J = 8.9 Hz), 4.28-4.36 (1H, m), 4.40-4.52 (1H, m), 4.64 (2H, t, J = 8.9 Hz), 4.80-4.90 (1H, m), 5.08 (2H, s), 5.30 (1H, t, J = 7.6 Hz), 5.41 (1H, brs), 6.57 (1H, d, J = 10.4 Hz), 7.05 (1H, brs), 7.28-7.38 (5H, m) |

Reference Example 31-1

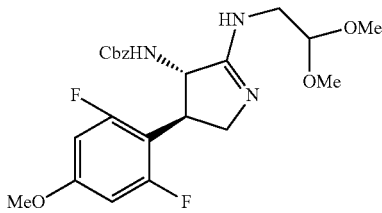

Benzyl {(3R*,4S*)-3-(2,6-difluoro-4-methoxyphenyl)-5-[(2,2-dimethoxyethyl)amino]-3,4-dihydro-2H-pyrrol-4-yl}carbamate To a solution of benzyl [(3R*,4S*)-5-ethoxy-3-(2,6-difluoro-4-methoxyphenyl)-3,4-dihydro-2H-pyrrol-4-yl]carbamate (56 mg) that was obtained in the same method as in Reference Example 28-1 in ethanol (0.7 mL) were added ammonium chloride (0.4 mg) and aminoacetaldehyde dimethyl acetal (18 μL) to produce a reaction solution. The reaction solution was stirred at room temperature for 18 hours. The reaction solution was concentrated under reduced pressure, and the obtained residue was then purified by silica gel column chromatography (hexane:ethyl acetate=1:1) to obtain the title compound as a colorless oil (51 mg).

$^1$H NMR (400 MHz, CDCl$_3$) δ: 3.40-3.62 (9H, m), 3.66-3.76 (1H, m), 3.79 (3H, s), 3.86-3.98 (1H, m), 4.54 (1H, t, J=5.2 Hz), 4.98 (1H, d, J=7.3 Hz), 5.04-5.16 (3H, m), 6.47 (2H, d, J=9.8 Hz), 7.30-7.42 (5H, m).

The following Reference Examples 31-2 to 31-4 were obtained using each corresponding amine in the same method as in Reference Example 31-1.

The structures and spectral data thereof are shown in Table 12.

TABLE 12

| Ref. No | Str. | Chemical name | P.D. |
|---|---|---|---|
| 31-2 | | benzyl {(3S*,4R*,Z)-4-(2,6-difluoro-4-methoxyphenyl)-2-[(2-hydroxyethoxy)imino]pyrrolidin-3-yl}carbamate | $^1$H-NMR (400 MHz, CDCl$_3$) δ: 2.87 (1H, brs), 3.50-3.64 (2H, m), 3.65-3.80 (4H, m), 3.83-3.90 (2H, m), 4.08 (1H, dd, J = 4.3, 4.3 Hz), 4.80-5.15 (3H, m), 5.13 (1H, dd, J = 9.8, 8.0 Hz), 5.25 (1H, s), 6.40-6.50 (2H, m), 7.26-7.32 (5H, m) |
| 31-3 | | ethyl 2-(((Z)-{(3S*,4R*)-3-[(benzyloxycarbonyl)amino]-4-(2,6-difluoro-4-methoxyphenyl)pyrrolidin-2-ylidene}amino)oxy)acetate | 1H-NMR (400 MHz, CDCl$_3$) δ: 1.29 (3H, t, J = 7.3 Hz), 3.56-3.77 (5H, m), 4.22 (2H, q, J = 7.3 Hz), 4.50 (2H, s), 4.93-5.19 (3H, m), 5.43 (1H, s), 5.88 (1H, s), 6.45 (2H, d, J = 10.4 Hz), 7.27-7.36 (5H, m) |
| 31-4 | | ethyl 3-((Z)-{(3S*,4R*)-3-[(benzyloxycarbonyl)amino]-4-(2,6-difluoro-4-methoxyphenyl)pyrrolidin-2-ylidene}amino)propionate | $^1$H-NMR (400 MHz, CDCl$_3$) δ: 1.28 (3H, t, J = 7.3 Hz), 2.64-2.78 (1H, m), 3.50-4.20 (9H, m), 4.02-4.09 (1H, m), 4.65-4.75 (1H, m), 4.95-5.20 (3H, m), 5.75 (1H, brs), 6.42-6.52 (2H, m), 7.27-7.37 (5H, m) |

Reference Example 32-1

[Chem. 66]

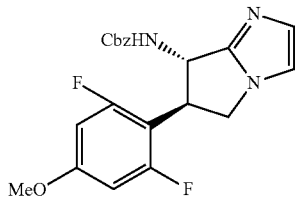

Benzyl [(6R*,7S*)-6-(2,6-difluoro-4-methoxyphenyl)-6,7-dihydro-5H-pyrrolo[1,2-a]imidazol-7-yl]carbamate To benzyl {(3R*,4S*)-3-(2,6-difluoro-4-methoxyphenyl)-5-[(2,2-dimethoxyethyl)amino]-3,4-dihydro-2H-pyrrol-4-yl}carbamate (51 mg) was added 1 mol/L hydrochloric acid (1.1 mL) to produce a reaction solution. The reaction solution was heated to reflux for 6 hours. To the reaction solution was added a saturated aqueous sodium hydrogen carbonate solution to neutralize the solution, and then the mixture was extracted with ethyl acetate. The organic layer was washed with water and then a brine, and dried over anhydrous sodium sulfate. The solvent was removed under reduced pressure, and the obtained residue was then purified by aminopropylated silica gel column chromatography (hexane:ethyl acetate=1:1) to obtain the title compound as a colorless oil (13 mg).

$^1$H NMR (400 MHz, CDCl$_3$) δ: 3.79 (3H, s), 4.17-4.27 (1H, m), 4.27-4.35 (1H, m), 5.00-5.08 (2H, m), 5.30-5.42 (2H, m), 6.49 (2H, d, J=9.8 Hz), 6.93 (1H, s), 7.15 (1H, s), 7.34 (5H, t, J=14.4 Hz).

Reference Example 33-1

[Chem. 67]

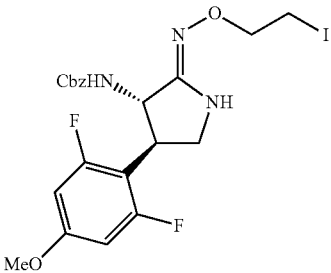

Benzyl {(3S*,4R*,Z)-4-(2,6-difluoro-4-methoxyphenyl)-2-[(2-iodoethoxy)imino]pyrrolidin-3-yl}carbamate Under an argon atmosphere, a solution of benzyl {(3S*,4R*,Z)-4-(2,6-difluoro-4-methoxyphenyl)-2-[(2-hydroxyethoxy)imino]pyrrolidin-3-yl}carbamate (44 mg) in tetrahydrofuran (1.0 mL) under ice-cooling were added imidazole (14 mg), triphenylphosphine (53 mg) and iodine (51 mg) to produce a reaction solution. The reaction solution was stirred at room temperature for 2 hours. An aqueous saturated sodium thiosulfate was added to the reaction solution, and the mixture was extracted with ethyl acetate. The organic layer was washed with a brine, and dried over anhydrous sodium sulfate. The solvent was removed under reduced pressure, and the residue was then purified by silica gel column chromatography (hexane:ethyl acetate=2:1) to obtain the title compound as a colorless oil (40 mg).

$^1$H NMR (400 MHz, DMSO-d$_6$) δ: 3.32-3.50 (2H, m), 3.58-3.71 (1H, m), 3.77 (3H, s), 3.97-4.05 (2H, m), 4.83-4.99 (3H, m), 6.67-6.86 (3H, m), 7.21-7.36 (5H, m), 7.70 (1H, d, J=9.2 Hz).

Reference Example 34-1

[Chem. 68]

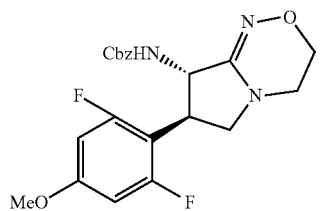

Benzyl [(7R*,8S*)-7-(2,6-difluoro-4-methoxyphenyl)-4,6,7,8-tetrahydro-3H-pyrrolo[2,1-c][1,2,4]oxadiazin-8-yl]carbamate Under an argon atmosphere, to a solution of benzyl {(3S*,4R*,Z)-4-(2,6-difluoro-4-methoxyphenyl)-2-[(2-iodoethoxy)imino]pyrrolidin-3-yl}carbamate (40 mg) in N,N-dimethylformamide (1.5 mL) under ice-cooling was added potassium tert-butoxide (16.5 mg) to produce a reaction solution. The reaction solution was stirred at room temperature for 2 hours. Water was added to the reaction solution, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=1:1) to obtain the title compound as a colorless oil (23 mg).

$^1$H NMR (400 MHz, DMSO-d$_6$) δ: 3.27-3.40 (4H, m), 3.49-3.72 (2H, m), 3.77 (3H, s), 3.82-3.90 (1H, m), 4.89-4.99 (3H, m), 6.76 (2H, d, J=11.0 Hz), 7.22-7.35 (5H, m), 7.76 (1H, d, J=9.2 Hz).

Reference Example 35-1

[Chem. 69]

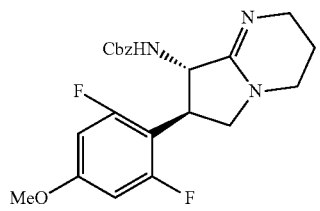

Benzyl [(7R*,8S*)-7-(2,6-difluoro-4-methoxyphenyl)-2,3,4,6,7,8-hexahydropyrrolo[1,2-a]pyrimidin-8-yl]carbamate To a solution of benzyl [(3R*,4S*)-5-ethoxy-3-(2,6-difluoro-4-methoxyphenyl)-3,4-dihydro-2H-pyrrol-4-yl]carbamate (59 mg) that was obtained in the same method as in Reference Example 28-1 in ethanol (0.3 mL) were added ammonium chloride (1 mg) and 3-bromopropylamine hydrobromide (35 mg) to produce a reaction solution. The reaction solution was stirred at room temperature for 2 hours. Then, potassium carbonate (61 mg) was added to the reaction solution, and the reaction mixture was stirred for 18 hours. Water was added to the reaction solution, and the mixture was extracted with ethyl acetate. The organic layer was washed with water and then a brine, and dried over anhydrous sodium sulfate. The solvent was removed under reduced pressure, and the obtained residue was then purified by aminopropylated silica gel column chromatography (ethyl acetate:methanol=4:1) to obtain the title compound as a colorless oil (27 mg).

$^1$H NMR (400 MHz, DMSO-$d_6$) δ: 1.60-1.73 (2H, m), 3.09-3.24 (4H, m), 3.32-3.44 (2H, m), 3.47-3.61 (1H, m), 3.76 (3H, s), 4.66 (1H, t, J=9.8 Hz), 4.92 (2H, s), 6.74 (2H, d, J=11.0 Hz), 7.22-7.35 (5H, m), 7.49 (1H, d, J=9.2 Hz).

Reference Example 36-1

[Chem. 70]

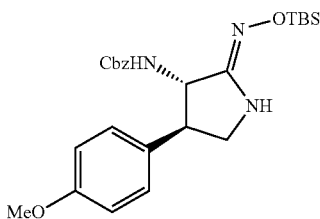

Benzyl ((3S*,4R*,Z)-2-{[(tert-butyldimethylsilyl)oxy]imino}-4-(4-methoxyphenyl)pyrrolidin-3-yl)carbamate Benzyl [(3R*,4S*)-5-ethoxy-3-(4-methoxyphenyl)-3,4-dihydro-2H-pyrrol-4-yl]carbamate that was obtained in the same method as in Reference Example 30-1 was subjected to react with O-(tert-butyldimethylsilyl)hydroxylamine as a reacting reagent instead of aminoacetaldehyde dimethyl acetal according to the same method as in Reference Example 31-1 to obtain the title compound.

$^1$H-NMR (400 MHz, DMSO-$d_6$) δ: 0.05 (6H, s), 0.90 (9H, s), 3.18 (1H, t, J=9.1 Hz), 3.22-3.40 (1H, m), 3.49 (1H, t, J=8.2 Hz), 3.72 (3H, s), 4.55 (1H, t, J=9.7 Hz), 4.91 (1H, d, J=13.3 Hz), 5.03 (1H, d, J=13.3 Hz), 6.49 (1H, s), 6.86 (2H, d, J=8.5 Hz), 7.20-7.33 (7H, m), 7.58 (1H, d, J=9.1 Hz).

Reference Example 37-1

[Chem. 71]

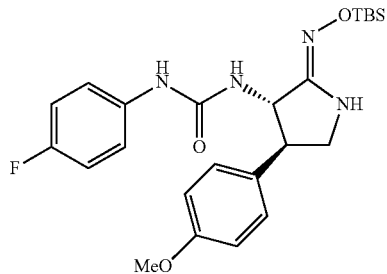

1-((3S*,4R*,Z)-2-{[(tert-Butyldimethylsilyl)oxy]imino}-4-(4-methoxyphenyl)pyrrolidin-3-yl)-3-(4-fluorophenyl)urea Using benzyl ((3S*,4R*,Z)-2-{[(tert-butyldimethylsilyl)oxy]imino}-4-(4-methoxyphenyl)pyrrolidin-3-yl)carbamate instead of benzyl [(6R*,7S*)-6-(2,6-difluoro-4-methoxyphenyl)-3-methyl-6,7-dihydro-5H-pyrrolo[2,1-c][1,2,4]triazol-7-yl]carbamate, the same method as in Example 7-1 was performed to obtain the title compound.

$^1$H-NMR (400 MHz, DMSO-$d_6$) δ: 0.04 (3H, s), 0.05 (3H, s), 0.89 (9H, s), 3.17 (1H, t, J=8.8 Hz), 3.28-3.37 (1H, m), 3.53 (1H, t, J=8.5 Hz), 3.71 (3H, s), 4.74 (1H, t, J=9.1 Hz), 6.34 (1H, d, J=9.1 Hz), 6.56 (1H, s), 6.86 (2H, d, J=8.5 Hz), 7.00-7.04 (2H, m), 7.27 (2H, d, J=8.5 Hz), 7.30-7.34 (2H, m), 8.45 (1H, s).

Reference Example 38-1

[Chem. 72]

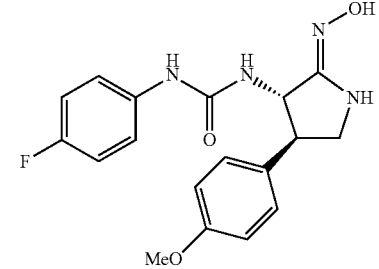

(−)-1-(4-Fluorophenyl)-3-[(3S*,4R*,Z)-2-(2-hydroxyimino)-4-(4-methoxyphenyl)pyrrolidin-3-yl]urea To a solution of 1-((3S*,4R*,Z)-2-{[(tert-butyldimethylsilyl)oxy]imino}-4-(4-methoxyphenyl)pyrrolidin-3-yl)-3-(4-fluorophenyl)urea (290 mg) in 1,4-dioxane (1.5 mL) were added water (1.35 mL) and trifluoroacetic acid (135 μL) to produce a reaction solution. The reaction solution was stirred at room temperature for 30 minutes. To the reaction solution under ice-cooling was added a saturated aqueous sodium hydrogen carbonate solution, and the mixture was extracted with ethyl acetate. The organic layer was washed with a brine, and dried over anhydrous sodium sulfate. The solvent was removed under reduced pressure, and the obtained residue was washed with diisopropyl ether to obtain the title compound as a white solid (212 mg).

¹H-NMR (400 MHz, DMSO-d₆) δ: 3.19 (1H, t, J=9.1 Hz), 3.30 (1H, q, J=8.7 Hz), 3.55 (1H, t, J=8.2 Hz), 3.76 (3H, s), 4.80 (1H, t, J=9.4 Hz), 6.37 (1H, d, J=9.1 Hz), 6.43 (1H, s), 6.92 (2H, d, J=8.5 Hz), 7.04-7.10 (2H, m), 7.32 (2H, d, J=8.5 Hz), 7.36-7.40 (2H, m), 8.49 (1H, s), 8.89 (1H, s).

MS (ESI+) m/z: 359 (MH⁺).

Reference Example 39-1

[Chem. 73]

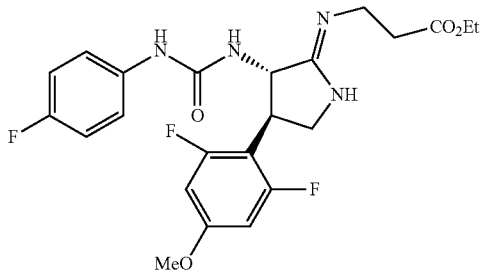

Ethyl 3-((Z)-{(3S*,4R*)-4-(2,6-difluoro-4-methoxyphenyl)-3-[3-(4-fluorophenyl)ureido]pyrrolidin-2-ylidene}amino)propionate Using ethyl 3-((Z)-{(3S*,4R*)-3-[(benzyloxycarbonyl)amino]-4-(2,6-difluoro-4-methoxyphenyl)pyrrolidin-2-ylidene}amino)propionate instead of benzyl [(6R*,7S*)-6-(2,6-difluoro-4-methoxyphenyl)-3-methyl-6,7-dihydro-5H-pyrrolo[2,1-c][1,2,4]triazol-7-yl]carbamate, the same method as in Example 7-1 was performed to obtain the title compound.

¹H NMR (400 MHz, DMSO-d₆) δ: 1.17 (3H, t, J=7.3 Hz), 2.65 (2H, t, J=7.3 Hz), 3.42-3.53 (2H, m), 3.57-3.66 (1H, m), 3.75 (3H, s), 3.86-3.93 (1H, m), 3.97-4.10 (3H, m), 5.18 (1H, t, J=8.6 Hz), 6.70 (1H, d, J=8.6 Hz), 6.77 (2H, d, J=11.0 Hz), 7.04 (2H, t, J=8.6 Hz), 7.33-7.37 (2H, m), 8.99 (1H, s).

Example 1-1

[Chem. 74]

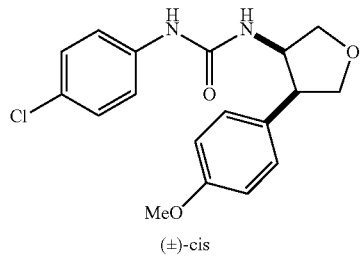

(±)-cis-1-(4-Chlorophenyl)-3-[4-(4-methoxyphenyl)tetrahydrofuran-3-yl]urea

Under an argon atmosphere, to a solution of (±)-cis-4-(4-methoxyphenyl)tetrahydrofuran-3-carboxylic acid (447 mg) in toluene (6.7 mL) were added triethylamine (336 μL) and diphenylphosphoryl azide (476 μL) to produce a reaction solution. The reaction solution was stirred at room temperature for 2 hours and then at 100° C. for 30 minutes. The reaction solution was allowed to cool to room temperature, then 4-chloroaniline (256 mg) was added thereto, and the reaction mixture was heated to reflux for 1 hour. The reaction solution was purified by silica gel column chromatography (hexane:ethyl acetate=2:1-1:20) to obtain a crude product, and the crude product was washed with diisopropyl ether to obtain the title compound as a white solid (502 mg).

¹H NMR (400 MHz, DMSO-d₆) δ: 3.49-3.59 (2H, m), 3.70 (3H, s), 3.89 (1H, t, J=7.9 Hz), 4.00 (1H, dd, J=8.5, 6.1 Hz), 4.15 (1H, t, J=8.5 Hz), 4.51-4.57 (1H, m), 5.89 (1H, d, J=8.5 Hz), 6.87 (2H, d, J=8.5 Hz), 7.15 (2H, d, J=8.5 Hz), 7.20 (2H, d, J=9.1 Hz), 7.28 (2H, d, J=9.1 Hz), 8.43 (1H, s).

MS (ESI+) m/z: 347 (MH)⁺.

The following Examples 1-2 to 1-11 were obtained using each corresponding aromatic amine in the same method as in Example 1-1.

The structures and spectral data thereof are shown in Tables 13 to 16.

TABLE 13

| Ex. No | Str. | Chemical name | P.D. |
|---|---|---|---|
| 1-2 | (structure with 3-fluorophenyl, MeO-phenyl, tetrahydrofuran) (±)-cis | (±)-cis-1-(3-fluorophenyl)-3-[4-(4-methoxyphenyl)tetrahydrofuran-3-yl]urea | ¹H-NMR (400 MHz, DMSO-d₆) δ: 3.49-3.60 (2H, m), 3.69 (3H, s), 3.89 (1H, dd, J = 8.6, 7.3 Hz), 4.01 (1H, dd, J = 8.6, 5.5 Hz), 4.15 (1H, dd, J = 8.6, 7.3 Hz), 4.50-4.58 (1H, m), 5.94 (1H, d, J = 8.6 Hz), 6.66 (1H, td, J = 8.6, 2.4 Hz), 6.87 (3H, d, J = 8.6 Hz), 7.13-7.23 (3H, m), 7.33 (1H, dt, J = 12.2, 2.4 Hz), 8.52 (1H, s) MS (ESI+) m/z: 331 (MH⁺) |

TABLE 13-continued

| Ex. No | Str. | Chemical name | P.D. |
|---|---|---|---|
| 1-3 | | (±)-cis-1-(2-fluorophenyl)-3-[4-(4-methoxyphenyl)tetrahydrofuran-3-yl]urea | $^1$H-NMR (400 MHz, DMSO-$d_6$) δ: 3.48-3.60 (2H, m), 3.69 (3H, s), 3.89 (1H, dd, J = 8.6, 7.3 Hz), 4.00 (1H, dd, J = 8.6, 5.8 Hz), 4.15 (1H, dd, J = 8.6, 7.3 Hz), 4.50-4.59 (1H, m), 5.94 (1H, d, J = 8.6 Hz), 6.66 (1H, td, J = 8.6, 1.8 Hz), 6.87 (3H, d, J = 8.6 Hz), 7.12-7.22 (3H, m), 7.33 (1H, dt, J = 12.2, 2.4 Hz), 8.52 (1H, s)<br>MS (ESI+) m/z: 331 (MH$^+$) |
| 1-4 | | (±)-cis-1-(2,4-difluorophenyl)-3-[4-(4-methoxyphenyl)tetrahydrofuran-3-yl]urea | $^1$H-NMR (400 MHz, DMSO-$d_6$) δ: 3.47-3.59 (2H, m), 3.69 (3H, s), 3.88 (1H, dd, J = 8.6, 7.9 Hz), 4.00 (1H, dd, J = 8.6, 6.1 Hz), 4.16 (1H, dd, J = 8.6, 7.3 Hz), 4.51-4.58 (1H, m), 6.40 (1H, d, J = 8.6 Hz), 6.86 (2H, d, J = 8.6 Hz), 6.90-6.96 (1H, m), 7.14 (2H, d, J = 8.6 Hz), 7.17-7.22 (1H, m), 7.95 (1H, td, J = 9.2, 6.1 Hz), 8.15 (1H, d, J = 1.8 Hz)<br>MS (ESI+) m/z: 349 (MH$^+$) |

TABLE 14

| Ex. No | Str. | Chemical name | P.D. |
|---|---|---|---|
| 1-5 | | (±)-cis-1-(3,4-difluorophenyl)-3-[4-(4-methoxyphenyl)tetrahydrofuran-3-yl]urea | $^1$H-NMR (400 MHz, DMSO-$d_6$) δ: 3.49-3.59 (2H, m), 3.70 (3H, s), 3.89 (1H, dd, J = 8.6, 7.3 Hz), 4.00 (1H, dd, J = 8.6, 6.1 Hz), 4.14 (1H, dd, J = 8.6, 7.3 Hz), 4.49-4.58 (1H, m), 5.93 (1H, d, J = 8.6 Hz), 6.87 (3H, d, J = 8.6 Hz), 7.14 (2H, d, J = 8.6 Hz), 7.22 (1H, dt, J = 11.0, 9.2 Hz), 7.49 (1H, ddd, J = 13.4, 7.3, 2.4 Hz), 8.50 (1H, s)<br>MS (ESI+) m/z: 349 (MH$^-$) |
| 1-6 | | (±)-cis-1-(4-cyanophenyl)-3-[4-(4-methoxyphenyl)-tetrahydrofuran-3-yl]urea | $^1$H-NMR (400 MHz, DMSO-$d_6$) δ: 3.50-3.62 (2H, m), 3.69 (3H, s), 3.89 (1H, dd, J = 8.6, 7.3 Hz), 4.01 (1H, dd, J = 8.6, 5.8 Hz), 4.16 (1H, dd, J = 8.6, 7.3 Hz), 4.51-4.59 (1H, m), 6.10 (1H, d, J = 8.6 Hz), 6.86 (2H, d, J = 8.6 Hz), 7.15 (2H, d, J = 8.6 Hz), 7.43 (2H, d, J = 8.6 Hz), 7.61 (2H, d, J = 8.6 Hz), 8.81 (1H, s)<br>MS (ESI+) m/z: 338 (MH$^+$) |

TABLE 14-continued

| Ex. No | Str. | Chemical name | P.D. |
|---|---|---|---|
| 1-7 | | (±)-cis-1-(5-chlorothiophen-2-yl)-3-[4-(4-methoxyphenyl)-tetrahydrofuran-3-yl]urea | ¹H-NMR (400 MHz, DMSO-d₆) δ: 3.49-3.60 (2H, m), 3.70 (3H, s), 3.89 (1H, dd, J = 8.6, 7.3 Hz), 4.00 (1H, dd, J = 8.6, 6.1 Hz), 4.13 (1H, dd, J = 8.6, 7.3 Hz), 4.47-4.56 (1H, m), 5.99 (1H, d, J = 8.6 Hz), 6.12 (1H, d, J = 3.7 Hz), 6.70 (1H, d, J = 3.7 Hz), 6.87 (2H, d, J = 9.2 Hz), 7.13 (2H, d, J = 9.2 Hz), 9.38 (1H, s) MS (ESI−) m/z: 353 (MH⁻) |

TABLE 15

| Ex. No | Str. | Chemical name | P.D. |
|---|---|---|---|
| 1-8 | | (±)-cis-1-[4-(2,6-difluoro-4-methoxyphenyl)-tetrahydrofuran-3-yl]-3-(4-fluorophenyl)urea | ¹H-NMR (400 MHz, DMSO-d₆) δ: 3.54 (1H, dd, J = 9.2, 4.9 Hz), 3.69 (3H, s), 3.76 (1H, q, J = 8.4 Hz), 3.98 (1H, t, J = 8.9 Hz), 4.04-4.12 (2H, m), 4.51-4.60 (1H, m), 6.04 (1H, d, J = 9.2 Hz), 6.66 (2H, d, J = 10.4 Hz), 6.98 (2H, t, J = 9.2 Hz), 7.14-7.21 (2H, m), 8.36 (1H, s) MS (ESI+) m/z: 367 (MH⁺) |
| 1-9 | | (±)-trans-1-(4-chlorophenyl)-3-[4-(4-methoxyphenyl)tetrahydrofuran-3-yl]urea | ¹H-NMR (400 MHz, CDCl₃) δ: 3.21 (1H, m), 3.51 (1H, dd, J = 8.6, 5.5 Hz), 3.66 (1H, t, J = 8.0 Hz), 3.71 (3H, s), 4.02-4.15 (2H, m), 4.18-4.24 (1H, m), 6.57 (1H, d, J = 7.3 Hz), 6.88 (2H, d, J = 9.2 Hz), 7.20-7.26 (4H, m), 7.34 (2H, d, J = 9.2 Hz), 8.51 (1H, s) MS (ESI+) m/z: 347 (MH⁺) |
| 1-10 | | (±)-1-(4-chlorophenyl)-3-[4-(4-methoxyphenyl)-1,1-dioxide-terrahydro-thiophen-3-yl]urea | ¹H-NMR (400 MHz, DMSO-d₆) δ: 3.10 (1H, ddd, J = 13.3, 6.7, 1.2 Hz), 3.31 (1H, dd, J = 13.3, 9.7 Hz), 3.52-3.59 (1H, m), 3.63-3.71 (1H, m), 3.74-3.80 (1H, m), 3.81 (3H, s), 4.57-4.66 (1H, m), 5.14 (1H, d, J = 6.7 Hz), 6.43 (1H, s), 6.91 (2H, d, J = 9.1 Hz), 7.16 (2H, d, J = 9.1 Hz), 7.22-7.27 (4H, m) MS (ESI+) m/z: 395 (MH⁻) |

TABLE 16

| Ex. No | Str. | Chemical name | P.D. |
|---|---|---|---|
| 1-11 | (±)-trans | (±)-trans-1-(4-chlorophenyl)-3-[4-(4-methoxyphenyl)-2-oxopiperidin-3-yl]urea | $^1$H-NMR (400 MHz, DMSO-$d_6$) δ: 1.80-1.89 (1H, m), 1.95-2.06 (1H, m), 3.14-3.30 (3H, m), 3.69 (3H, s), 4.13 (1H, dd, J = 12.1, 8.5 Hz), 6.17 (1H, d, J = 8.5 Hz), 6.83 (2H, d, J = 8.5 Hz), 7.17 (2H, d, J = 8.5 Hz), 7.20 (2H, d, J = 8.5 Hz), 7.34 (2H, d, J = 8.5 Hz), 7.60 (1H, s), 8.52 (1H, s) MS (ESI+) m/z: 374 (MH$^+$) |

Example 2-1

[Chem. 75]

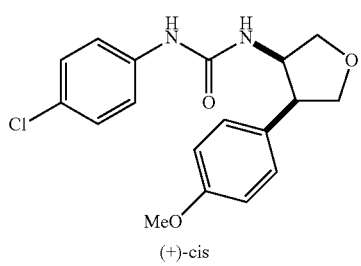

(+)-cis

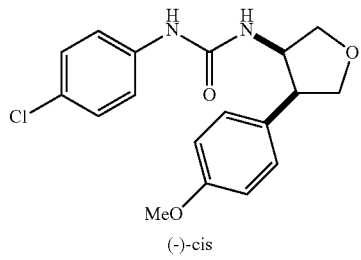

(−)-cis (+)-cis-1-(4-Chlorophenyl)-3-[4-(4-methoxyphenyl)tetrahydrofuran-3-yl]urea (−)-cis-1-(4-Chlorophenyl)-3-[4-(4-methoxyphenyl)tetrahydrofuran-3-yl]urea (±)-cis-1-(4-Chlorophenyl)-3-[4-(4-methoxyphenyl)tetrahydrofuran-3-yl]urea that was obtained in Example 1-1 was subjected to optical resolution by high performance liquid chromatography (methyl tert-butyl ether:ethanol:hexane=65:3:32, flow rate: 20.0 mL) using a column for separation of enantiomers (CHIRALPAK ID) to obtain the title compounds of two isomers as a white solid: Isomer A (+) with a retention time of 26.20 minutes, and Isomer B (−) with a retention time of 41.76 minutes.

Isomer A (+):
$^1$H NMR (400 MHz, DMSO-$d_6$) δ: 3.49-3.59 (2H, m), 3.70 (3H, s), 3.89 (1H, t, J=7.9 Hz), 4.00 (1H, dd, J=8.5, 6.1 Hz), 4.15 (1H, t, J=8.5 Hz), 4.51-4.57 (1H, m), 5.89 (1H, d, J=8.5 Hz), 6.87 (2H, d, J=8.5 Hz), 7.15 (2H, d, J=8.5 Hz), 7.20 (2H, d, J=9.1 Hz), 7.28 (2H, d, J=9.1 Hz), 8.43 (1H, s).
MS (ESI+) m/z: 347 (MH)$^+$.
$[α]_D^{24}$+130 (c 0.35, EtOH).

Isomer B (−):
$^1$H NMR (400 MHz, DMSO-$d_6$) δ: 3.49-3.59 (2H, m), 3.70 (3H, s), 3.89 (1H, t, J=7.9 Hz), 4.00 (1H, dd, J=8.5, 6.1 Hz), 4.15 (1H, t, J=8.5 Hz), 4.51-4.57 (1H, m), 5.89 (1H, d, J=8.5 Hz), 6.87 (2H, d, J=8.5 Hz), 7.15 (2H, d, J=8.5 Hz), 7.20 (2H, d, J=9.1 Hz), 7.28 (2H, d, J=9.1 Hz), 8.43 (1H, s).
MS (ESI+) m/z: 347 (MH)$^+$.
$[α]_D^{24}$−129 (c 0.35, EtOH).

Example 3-1

[Chem. 76]

Isomer A

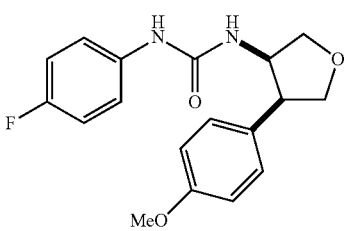

(+)-cis

Isomer B

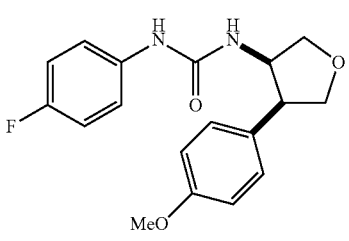

(−)-cis (+)-cis-1-(4-Fluorophenyl)-3-[4-(4-methoxyphenyl)tetrahydrofuran-3-yl]urea (−)-cis-1-(4-Fluorophenyl)-3-[4-(4-methoxyphenyl)tetrahydrofuran-3-yl]urea (±)-cis-1-(4-Fluorophenyl)-3-[4-(4-methoxyphenyl)tetrahydrofuran-3-yl]urea that was obtained in the same method as in Example 1-1 using 4-fluoroaniline instead of 4-chloroaniline was subjected to optical resolution by high performance liquid chromatography (methyl tert-butyl ether:ethanol=95:5, flow rate: 20.0 mL) using a column for separation of enantiomers (CHIRALPAK ID) to obtain the title compounds of two isomers as a white solid: Isomer A (+) with a retention time of 11.44 minutes, and Isomer B (−) with a retention time of 14.50 minutes.

Isomer A (+):
$^1$H NMR (400 MHz, DMSO-$d_6$) δ: 3.49-3.58 (2H, m), 3.70 (3H, s), 3.89 (1H, dd, J=8.5, 7.3 Hz), 4.00 (1H, dd, J=8.5, 6.1 Hz), 4.15 (1H, dd, J=8.5, 7.3 Hz), 4.50-4.57 (1H, m), 5.82 (1H, d, J=9.1 Hz), 6.87 (2H, d, J=9.1 Hz), 6.96-7.03 (2H, m), 7.15 (2H, d, J=9.1 Hz), 7.22-7.28 (2H, m), 8.32 (1H, s).
MS (ESI+) m/z: 331 (MH)$^+$.
$[α]_D^{24}$+101 (c 0.35, EtOH).

Isomer B (−):
$^1$H NMR (400 MHz, DMSO-$d_6$) δ: 3.49-3.58 (2H, m), 3.70 (3H, s), 3.89 (1H, dd, J=8.5, 7.3 Hz), 4.00 (1H, dd, J=8.5, 6.1 Hz), 4.15 (1H, dd, J=8.5, 7.3 Hz), 4.50-4.57 (1H, m), 5.82 (1H, d, J=9.1 Hz), 6.87 (2H, d, J=9.1 Hz), 6.96-7.03 (2H, m), 7.15 (2H, d, J=9.1 Hz), 7.22-7.28 (2H, m), 8.32 (1H, s). MS (ESI+) m/z: 331 (MH)$^+$.
$[α]_D^{24}$−104 (c 0.35, EtOH).

Example 4-1

[Chem. 77]

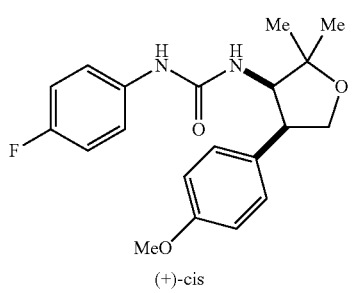

Isomer A
(+)-cis

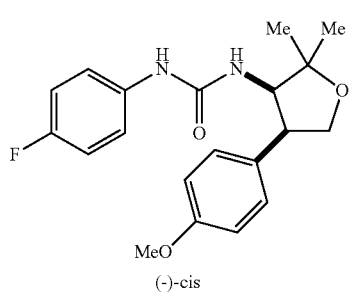

Isomer B
(−)-cis (+)-cis-1-(4-Fluorophenyl)3-[4-(4-methoxyphenyl)-2,2-dimethyltetrahydrofuran-3-yl]urea (−)-cis-1-(4-Fluorophenyl)3-[4-(4-methoxyphenyl)-2,2-dimethyltetrahydrofuran-3-yl]urea (±)-cis-1-(4-Fluorophenyl)3-[4-(4-methoxyphenyl)-2,2-dimethyltetrahydrofuran-3-yl]urea that was obtained in the same method as in Example 1-1 using (±)-cis-4-(4-methoxyphenyl)-2,2-dimethyltetrahydrofuran-3-carboxylic acid instead of (±)-cis-4-(4-methoxyphenyl)tetrahydrofuran-3-carboxylic acid was subjected to optical resolution by high performance liquid chromatography (ethanol:hexane=20:80, flow rate: 10.0 mL) using a column for separation of enantiomers (CHIRALPAK IA) to obtain the title compounds of two isomers as a white solid: Isomer A (+) with a retention time of 12 minutes, and Isomer B (−) with a retention time of 14 minutes.

Isomer A (+):
$^1$H NMR (400 MHz, DMSO-$d_6$) δ: 1.09 (3H, s), 1.28 (3H, s), 3.69 (3H, s), 3.73-3.81 (1H, m), 3.89 (1H, t, J=8.8 Hz), 4.12 (1H, dd, J=8.8, 7.3 Hz), 4.27 (1H, dd, J=10.3, 6.7 Hz), 5.86 (1H, d, J=10.3 Hz), 6.85 (2H, d, J=8.5 Hz), 6.96-7.03 (2H, m), 7.15 (2H, d, J=8.5 Hz), 7.24-7.28 (2H, m), 8.32 (1H, s).
MS (FD+) m/z: 358 (M)$^+$.
$[α]_D^{24}$+102 (c 0.33, EtOH).

Isomer B (−):
$^1$H NMR (400 MHz, DMSO-$d_6$) δ 1.09 (3H, s), 1.28 (3H, s), 3.69 (3H, s), 3.73-3.81 (1H, m), 3.89 (1H, t, J=8.8 Hz), 4.12 (1H, dd, J=8.8, 7.3 Hz), 4.27 (1H, dd, J=10.3, 6.7 Hz), 5.86 (1H, d, J=10.3 Hz), 6.85 (2H, d, J=8.5 Hz), 6.96-7.03 (2H, m), 7.15 (2H, d, J=8.5 Hz), 7.24-7.28 (2H, m), 8.32 (1H, s).
MS (FD+) m/z: 358 (M)$^+$.
$[α]_D^{24}$−103 (c 0.37, EtOH).

Example 5-1

[Chem. 78]

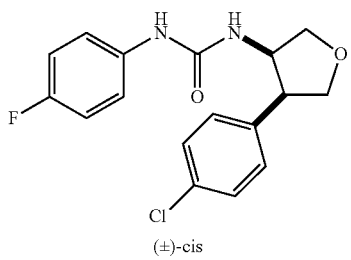

(±)-cis (±)-cis-1-[4-(4-Chlorophenyl)tetrahydrofuran-3-yl]-3-(4-fluorophenyl)urea Under an argon atmosphere, to a solution of (±)-cis-4-(4-chlorophenyl)tetrahydrofuran-3-amine (200 mg) in tetrahydrofuran (5 mL) under ice-cooling was added 4-fluorophenyl isocyanate (0.115 mL) to produce a reaction solution. The reaction solution was stirred at room temperature for 1 hour. The reaction solution was concentrated under reduced pressure, and the obtained residue was then purified by silica gel column chromatography (ethyl acetate:hexane=1:1) to obtain the title compound as a white solid (270 mg).

¹H-NMR (400 MHz, DMSO-d₆) δ 3.53-3.62 (2H, m), 3.91 (1H, dd, J=8.5, 7.3 Hz), 4.02 (1H, dd, J=8.5, 6.7 Hz), 4.16 (1H, dd, J=8.5, 7.3 Hz), 4.55-4.64 (1H, m), 5.91 (1H, d, J=8.5 Hz), 7.00 (2H, t, J=8.5 Hz), 7.20-7.27 (4H, m), 7.36 (2H, d, J=8.5 Hz), 8.24 (1H, s).

MS (ESI+) m/z: 335 (MH)⁺.

The following Examples 5-2 to 5-4 were obtained using each corresponding aromatic amine in the same method as in Example 5-1.

The structures and spectral data thereof are shown in Table 17.

(±)-trans-1-(4-Fluorophenyl)-3-[3-(4-methoxyphenyl)-5-oxopyrrolidin-2-yl]urea

To a solution of tert-butyl (±)-trans-[3-(4-methoxyphenyl)-5-oxopyrrolidin-2-yl]carbamate (30 mg) in dichloromethane (0.5 mL) was added trifluoroacetic acid (0.5 mL) to produce a reaction solution. The reaction solution was stirred under ice-cooling for 1.5 hours. The reaction solution was concentrated under reduced pressure. To the obtained residue were added ethyl acetate and a saturated aqueous sodium hydrogen carbonate solution, and the pH in the

TABLE 17

| Ex. No | Str. | Chemical name | P.D. |
|---|---|---|---|
| 5-2 | | (±)-cis-1-[4-(4-fluorophenyl)-tetrahydrofuran-3-yl]-3-(4-fluorophenyl)urea | ¹H-NMR (400 MHz, DMSO-d₆) δ: 3.53-3.62 (2H, m), 3.89 (1H, dd, J = 8.6, 7.3 Hz), 4.00 (1H, dd, J = 8.6, 6.1 Hz), 4.14 (1H, dd, J = 8.6, 7.3 Hz), 4.52-4.61 (1H, m), 5.91 (1H, d, J = 8.6 Hz), 6.99 (2H, t, J = 8.6 Hz), 7.11 (2H, t, J = 8.6 Hz), 7.20-7.27 (4H, m), 8.23 (1H, s) MS (ESI+) m/z: 319 (MH⁺) |
| 5-3 | | (±)-cis-1-[4-(4-cyanophenyl)tetrahydrofuran-3-yl]-3-(4-fluorophenyl)urea | ¹H-NMR (400 MHz, DMSO-d₆) δ: 3.59 (1H, dd, J = 8.6, 4.3 Hz), 3.70 (1H, q, J = 7.3 Hz), 3.95 (1H, dd, J = 8.6, 7.3 Hz), 4.03 (1H, dd, J = 8.6, 6.1 Hz), 4.17 (1H, dd, J = 8.6, 7.3 Hz), 4.61-4.69 (1H, m), 6.02 (1H, d, J = 8.6 Hz), 7.00 (2H, t, J = 9.2 Hz), 7.18-7.25 (2H, m), 7.43 (2H, d, J = 7.9 Hz), 7.77 (2H, d, J = 8.6 Hz), 8.18 (1H, s) MS (ESI+) m/z: 326 (MH⁺) |
| 5-4 | | (±)-1-(4-chlorophenyl)-3-[4-(4-methoxyphenyl)-2-oxooxazolidin-3-yl]urea | ¹H-NMR (400 MHz, DMSO-d₆) δ: 3.72 (3H, s), 4.09 (1H, s), 4.70 (1H, t, J = 8.5 Hz), 5.02 (1H, s), 6.93 (2H, d, J = 8.5 Hz), 7.28 (2H, d, J = 8.5 Hz), 7.43 (4H, d, J = 8.5 Hz), 8.51 (1H, s), 8.89 (1H, s). MS (ESI+) m/z: 362 (MH⁺) |

Example 6-1

[Chem. 79]

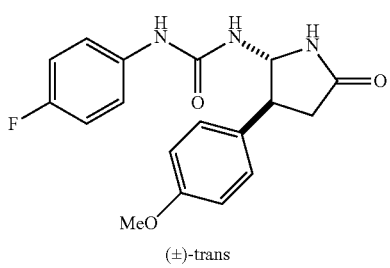

(±)-trans aqueous layer thereof was adjusted to 9. To the bilayer solution was added 4-fluorophenyl isocyanate (20 μL), and the reaction mixture was stirred at room temperature for 1 hour and then extracted with ethyl acetate. The organic layer was washed with water and then a brine, and dried over anhydrous sodium sulfate. The solvent was removed under reduced pressure, and the residue was then purified by silica gel column chromatography (ethyl acetate:hexane=4:1-ethyl acetate-ethyl acetate:methanol=95:5) to obtain the title compound as a white solid (26 mg).

¹H NMR (400 MHz, DMSO-d₆) δ: 2.33 (1H, dd, J=16.5, 9.2 Hz), 2.61 (1H, dd, J=16.5, 9.2 Hz), 3.22-3.35 (1H, m), 3.71 (3H, s), 5.24 (1H, t, J=9.2 Hz), 6.84-6.94 (3H, m), 7.04 (2H, t, J=8.9 Hz), 7.24 (2H, d, J=8.6 Hz), 7.37 (2H, dd, J=9.2, 5.5 Hz), 8.18 (1H, s), 8.52 (1H, s).

Example 7-1

[Chem. 80]

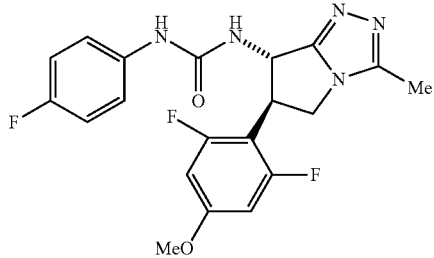

(−)-1-[(6R*,7S*)-6-(2,6-Difluoro-4-methoxyphenyl)-3-methyl-6,7-dihydro-5H-pyrrolo[2,1-c][1,2,4]triazol-7-yl]-3-(4-fluorophenyl)urea To a solution of benzyl [(6R*,7S*)-6-(2,6-difluoro-4-methoxyphenyl)-3-methyl-6,7-dihydro-5H-pyrrolo[2,1-c][1,2,4]triazol-7-yl]carbamate (10 mg) in ethanol (0.5 mL) was added 10% palladium carbon (2 mg), and the mixture was stirred under a hydrogen atmosphere for 3 hours. The reaction solution was filtered over Celite, and the solvent of the filtrate was removed to obtain (6R*,7S*)-6-(2,6-difluoro-4-methoxyphenyl)-3-methyl-6,7-dihydro-5H-pyrrolo[2,1-c][1,2,4]triazol-7-amine that is an intermediate compound as a colorless oil. To a solution of the obtained (6R*,7S*)-6-(2,6-difluoro-4-methoxyphenyl)-3-methyl-6,7-dihydro-5H-pyrrolo[2,1-c][1,2,4]triazol-7-amine (7.3 mg) in tetrahydrofuran (0.5 mL) was added 4-fluorophenyl isocyanate (2.7 µL) to produce a reaction solution. The reaction solution was stirred at room temperature for 20 minutes. The reaction solution was concentrated under reduced pressure, and the obtained residue was then purified by silica gel column chromatography (hexane:ethyl acetate=4:1-ethyl acetate) to obtain the title compound as a white solid (5.4 mg).

$^1$H NMR (400 MHz, DMSO-$d_6$) δ: 2.32 (3H, s), 3.77 (3H, s), 3.91 (1H, dd, J=10.4, 8.6 Hz), 4.31-4.46 (2H, m), 5.38 (1H, t, J=7.9 Hz), 6.79 (2H, d, J=11.0 Hz), 6.88-6.95 (1H, m), 7.03 (2H, t, J=9.2 Hz), 7.32-7.37 (2H, m), 8.85 (1H, s).
MS (ESI+) m/z: 418 (MH)$^+$.
$[α]_D^{27}$ −79 (c 0.20, EtOH).

The following Examples 7-2 to 7-7 were obtained using each corresponding Cbz compound in the same method as in Example 7-1.

The structures and spectral data thereof are shown in Tables 18 and 19.

TABLE 18

| Ex. No | Str. | Chemical name | P.D. |
|---|---|---|---|
| 7-2 | | (−)-1-[(6R*,7S*)-6-(2,6-difluoro-4-methoxyphenyl)-6,7-dihydro-5H-pyrrolo[1,2-a]imidazol-7-yl]-3-(4-fluorophenyl)urea | $^1$H-NMR (400 MHz, DMSO-$d_6$) δ: 3.78 (3H, s), 3.93 (1H, dd, J = 10.4, 8.6 Hz), 4.22 (1H, q, J = 8.6 Hz), 4.43 (1H, t, J = 10.4 Hz), 5.30 (1H, t, J = 7.9 Hz), 6.74-6.83 (3H, m), 7.00 (1H, s), 7.04 (2H, t, J = 8.6 Hz), 7.16 (1H, s), 7.31-7.38 (2H, m), 8.67 (1H, s) MS (ESI+) m/z; 403 (MH$^+$) $[α]_D^{29}$ −121 (c 0.098, EtOH) |
| 7-3 | | (−)-1-(4-fluorophenyl)-3-[(6R*,7S*)-6-(4-methoxyphenyl)-6,7-dihydro-5H-pyrrolo[1,2-d]tetrazol-7-yl]urea | $^1$H-NMR (400 MHz, DMSO-$d_6$) δ: 3.74 (3H, s), 4.28-4.41 (2H, m), 4.86 (1H, dd, J = 9.7, 7.3 Hz), 5.50 (1H, dd, J = 9.1, 9.1 Hz), 6.90-6.95 (3H, m), 7.04 (2H, m), 7.37 (2H, m), 7.43 (2H, d, J = 8.5 Hz), 8.83 (1H, s) MS (ESI+) m/z: 369 (MH$^+$) $[α]_D^{28.5}$ −183 (c 0.311, EtOH) |

TABLE 18-continued

| Ex. No | Str. | Chemical name | P.D. |
|---|---|---|---|
| 7-4 | | (−)-1-[(6R*,7S*)-6-(2,6-difluoro-4-methoxyphenyl)-6,7-dihydro-5H-pyrrolo[1,2-d]tetrazol-7-yl]-3-(4-fluorophenyl)urea | $^1$H-NMR (400 MHz, DMSO-$d_6$) δ: 3.77 (3H, s), 4.36 (1H, dd, J = 11.6, 7.9 Hz), 4.64-4.72 (1H, m), 4.89 (1H, J = 11.6 Hz), 5.42 (1H, t, J = 7.9 Hz), 6.81 (2H, d, J = 10.4 Hz), 6.99-7.07 (3H, m), 7.30-7.36 (2H, m), 9.10 (1H, s) MS (ESI+) m/z: 405 (MH$^+$) $[α]_D^{29}$ −51 (c 0.067, EtOH) |

TABLE 19

| Ex. No | Str. | Chemical name | P.D. |
|---|---|---|---|
| 7-5 | | (−)-1-[(6R*,7S*)-6-(6-fluoro-2,3-dihydrobenzofuran-5-yl)-6,7-dihydro-5H-pyrrolo[1,2-d]tetrazol-7-yl]-3-(4-fluorophenyl)urea | $^1$H-NMR (400 MHz, CDCl$_3$) δ: 3.18 (2H, t, J = 8.9 Hz), 4.35 (1H, dd, J = 11.0, 7.9 Hz), 4.55-4.60 (1H, m), 4.63 (2H, t, J = 8.9 Hz), 4.83-4.89 (1H, m), 5.38 (1H, t, J = 7.6 Hz), 6.49 (1H, d, J = 7.3 Hz), 6.56 (1H, d, J = 11.0 Hz), 6.78-6.83 (2H, m), 7.09-7.14 (3H, m), 7.33 (1H, s) MS (ESI+) m/z: 399 (MH$^+$) $[α]_D^{24}$ −107 (c 0.15, EtOH) |
| 7-6 | | (−)-1-[(7R*,8S*)-7-(2,6-difluoro-4-methoxyphenyl)-2,3,4,6,7,8-hexahydropyrrolo[1,2-a]pyrimidin-8-yl]-3-(4-fluorophenyl)urea | $^1$H-NMR (400 MHz, DMSO-$d_6$) δ: 1.19-1.31 (2H, m), 1.66-1.79 (2H, m), 3.15-3.60 (5H, m), 3.76 (3H, s), 4.84-4.86 (1H, m), 6.24-6.43 (1H, m), 6.73 (2H, d, J = 11 Hz), 7.02 (2H, t, J = 8.6 Hz), 7.26-7.34 (2H, m), 8.75 (1H, s) MS (ESI+) m/z: 419 (MH$^+$) $[α]_D^{29}$ −261 (c 0.12, EtOH) |

TABLE 19-continued

| Ex. No | Str. | Chemical name | P.D. |
|---|---|---|---|
| 7-7 | | 1-[(7R*,8S*)-7-(2,6-difluoro-4-methoxyphenyl)-4,6,7,8-tetrahydro-3H-pyrrolo[2,1-c][1,2,4]oxadiazin-8-yl]-3-(4-fluorophenyl)urea | $^{1}$H-NMR (400 MHz, DMSO-$d_6$) δ: 3.35-3.38 (3H, m), 3.55 (1H, t, J = 9.1 Hz), 3.61-3.70 (2H, m), 3.75 (3H, s), 3.83-3.90 (1H, m), 5.13 (1H, t, J = 9.4 Hz), 6.55 (1H, d, J = 7.9 Hz), 6.73 (2H, d, J = 10.9 Hz), 7.00 (2H, t, J = 9.1 Hz), 7.27-7.33 (2H, m), 8.62 (1H, s) MS (ESI+) m/z: 421 (MH$^+$) |

Example 8-1

[Chem. 81]

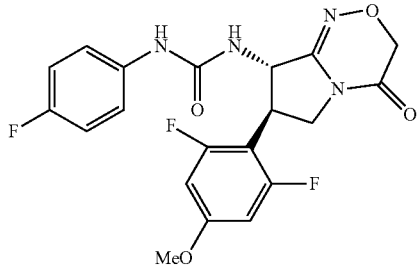

(−)-1-[(7R*,8S*)-7-(2,6-Difluoro-4-methoxyphenyl)-4-oxo-4,6,7,8-tetrahydro-3H-pyrrolo[2,1-c][1,2,4]oxadiazin-8-yl]-3-(4-fluorophenyl)urea Using ethyl 2-(((Z)-{(3S*,4R*)-3-[(benzyloxycarbonyl)amino]-4-(2,6-difluoro-4-methoxyphenyl)pyrrolidin-2-ylidene}amino)oxy)acetate instead of benzyl [(6R*,7S*)-6-(2,6-difluoro-4-methoxyphenyl)-3-methyl-6,7-dihydro-5H-pyrrolo[2,1-c][1,2,4]triazol-7-yl]carbamate, the same method as in Example 7-1 was performed to obtain the title compound.

$^{1}$H NMR (400 MHz, CDCl$_3$) δ: 3.77 (3H, s), 3.78-3.86 (2H, m), 4.06-4.18 (2H, m), 4.25-4.34 (1H, m), 5.03-5.10 (1H, m), 6.47 (2H, d, J=10.4 Hz), 6.88-6.96 (2H, m), 7.34-7.40 (2H, m), 7.70 (1H, d, J=2.4 Hz), 8.69 (1H, s).

MS (ESI+) m/z: 435 (MH$^+$).

[α]$_D^{25}$ −89 (c 0.12, EtOH).

Example 9-1

[Chem. 82]

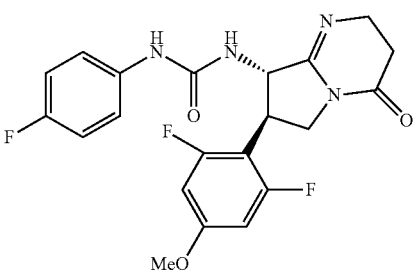

(−)-1-[(7R*,8S*)-7-(2,6-Difluoro-4-methoxyphenyl)-4-oxo-2,3,4,6,7,8-hexahydropyrrolo[1,2-a]pyrimidin-8-yl]-3-(4-fluorophenyl)urea To a solution of ethyl 3-((Z)-{(3S*,4R*)-4-(2,6-difluoro-4-methoxyphenyl)-3-[3-(4-fluorophenyl)ureido]pyrrolidin-2-ylidene}amino)propionate (12 mg) in N,N-dimethylformamide (0.3 mL) was added cesium carbonate (9.8 mg), and the mixture was stirred at room temperature for a day. To the reaction solution was added ethyl acetate. The organic layer was washed with water and then a brine, and dried over anhydrous sodium sulfate. The solvent was removed under reduced pressure, and the obtained residue was washed with diisopropyl ether to obtain the title compound as a white solid (10 mg).

$^{1}$H-NMR (400 MHz, CDCl$_3$) δ: 2.51-2.59 (2H, m), 3.70-3.74 (4H, m), 3.75 (3H, s), 4.12 (1H, d, J=9.2 Hz), 5.22 (1H, s), 6.50 (2H, d, J=10.4 Hz), 6.88-6.96 (2H, m), 7.13-7.21 (2H, m).

MS (ESI+) m/z: 433 (MH)$^+$.

[α]$_D^{25}$ −108 (c 0.10, EtOH).

Example 10-1

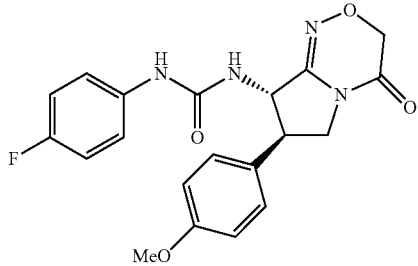

1-(4-Fluorophenyl)-3-[(7R*,8S*)-7-(4-methoxyphenyl)-4-oxo-4,6,7,8-tetrahydro-3H-pyrrolo[2,1-c][1,2,4]oxadiazin-8-yl]urea To a solution of (−)-1-(4-fluorophenyl)-3-[(3S*,4R*,Z)-2-(2-hydroxyimino)-4-(4-methoxyphenyl)pyrrolidin-3-yl]urea (84 mg) in N,N-dimethylformamide (0.6 mL) was added cesium carbonate (91 mg) to produce a reaction solution. The reaction solution was stirred at room temperature for 30 minutes. Then, ethyl bromoacetate (31 µL) was added to the reaction solution, and the reaction mixture was stirred at room temperature for 1 day. To the reaction solution was added ethyl acetate. The organic layer was washed with water and then a brine, and dried over anhydrous sodium sulfate. The solvent was removed under reduced pressure, and the obtained residue was washed with diisopropyl ether to obtain the title compound as a white solid (59 mg).

$^1$H-NMR (400 MHz, DMSO-$d_6$) δ: 3.44-3.58 (2H, m), 3.72 (3H, s), 4.11 (1H, m), 4.21 (1H, d, J=15.7 Hz), 4.44 (1H, d, J=15.7 Hz), 5.30 (1H, m), 6.64 (1H, d, J=9.1 Hz), 6.91 (2H, d, J=9.1 Hz), 7.03 (2H, m), 7.31-7.37 (4H, m), 8.65 (1H, s).

MS (ESI+) m/z: 399 (MH)$^+$.

Next, results in support of utility of the compound of the present invention will be shown with reference to Test Examples.

Test Example 1

Measurement test of agonist activity on human FPRL1

(1-1) Construction of Human FPRL1 Expression Vector

Human FPRL (SEQ ID NO: 3) was amplified in a PCR reaction from cDNA derived from a monocytic leukemia cell line THP-1 (TIB-202, ATCC) as a template using a forward primer shown in SEQ ID NO: 1, a reverse primer shown in SEQ ID NO: 2, and KOD-plus-ver. 2 (KOD-211, TOYOBO CO., LTD.). The amplified PCR product and pCMV-script vector (212220, STRATAGENE) were digested with Hind III (1060A, Takara Bio Inc.) and XhoI (1094A, Takara Bio Inc.), and the resultant digest was ligated with Ligation high ver. 2 (LGK-201, TOYOBO CO., LTD.). The ligation product was transformed into DH5α (DNA-901, TOYOBO CO., LTD.), cultured on a 100 µg/mL kanamycin-containing LB medium, and purified with HiSpeed Plasmid Maxi Kit (12662, QIAGEN).

(1-2) Construction of Human Gα15 Expression Vector

Human Gα15 (SEQ ID NO: 6) was amplified in a PCR reaction from cDNA derived from a myeloid leukemia cell line HL-60 (CCL-240, ATCC) as a template using a forward primer shown in SEQ ID NO: 4, a reverse primer shown in SEQ ID NO: 5, and KOD-plus-ver. 2. The amplified PCR product and pCMV-script vector were digested with Hind III and XhoI, and the resultant digest was ligated with Ligation high ver. 2. The ligation product was transformed into DH5α, cultured on a 100 µg/mL kanamycin-containing LB medium, and purified with HiSpeed Plasmid Maxi Kit.

(2-1) Method for Culturing and Subculturing HEK293

HEK293 (JCRB9068, NIBIO) was cultured in an incubator at 5% $CO_2$ and 37° C. using DMEM (11885-092, GIBCO) containing 10% FBS and 1cPenicillin-Streptomycin (15140-122, GIBCO). Subculture was carried out as followings: The cells that reached 80 to 90% confluency were washed with PBS(−), separated using 0.25% Trypsin-EDTA (25200-072, GIBCO), centrifuged, resuspended in a fresh medium, and then seeded in Collagen Type 1 Coated dish (4020-010, IWAKI) at a split ratio of 1:8 (cultured for 3 days).

(2-2) Introduction of Human FPRL1 and Gal5 Expression Vectors

HEK293 that reached 80 to 90% confluency was washed with PBS(−), separated using 0.25% Trypsin-EDTA, centrifuged, and re-suspended in a fresh medium excluding 1×Penicillin-Streptomycin. The cells were inoculated in a Collagen Type 1 coated 6-well plate (4810-010, IWAKI) to 5×10$^5$ cells/2.5 mL/well and cultured overnight. On the next day, human FPRL1 and Gα15 expression vectors were introduced using Lipofectamine 2000 transfection reagent (11668-019, Life technologies). First, the human FPRL1 and Gal5 expression vectors were diluted with Opti-MEM I Reduced Serum Medium (31985-070, GIBCO) to 2 µg/250 µL/well and Lipofectamine 2000 transfection reagent was diluted with Opti-MEM I Reduced Serum Medium to be 4 µL/250 µL/well. The vectors and reagent were softly diffused, and incubated at room temperature for 5 minutes. The vector solution was mixed with Lipofectamine 2000 transfection reagent in equal amounts. In order to form a complex of the vectors and Lipofectamine 2000 transfection reagent, the mixture was incubated at room temperature for 20 minutes, and added at 500 µL/well to the medium of inoculated cells. The treated cells were cultured for 24 hours, inoculated in Poly-D-Lysine coated 96-well plate (356640, BD Biosciences) at a cell density of 7×10$^4$ cells/100 µL/well, and cultured for another 24 hours. The resultant cells were used in a measurement test of calcium mobilization in the cells.

(3) Evaluation of Agonist Activity on Human FPRL1 (Test of Calcium Mobilization in Cell)

An appropriate amount of each test compound was first weighed, and dissolved to 10$^{-2}$ M by addition of dimethyl sulfoxide (DMSO). For calculation of an $EC_{50}$ value for agonist activity, each compound solution was serially diluted with DMSO by 10-fold increments to make eight solutions having a concentration of 10$^{-2}$ M to 10$^{-9}$ M. The formed compound solution having each concentration was diluted 100 times with an assay buffer that was contained in Fluo-4 NW Calcium Assay Kit (F36206, Life technologies), and dispensed in an amount of 100 µL into a 96-well plate with a V-bottom shape. The plate dispensed with compound solutions was set in Flexstation (Molecular Devices, LLC.) until measurement.

Subsequently, 10 mL of assay buffer and 100 µL of probenecid solution (dissolved by addition of 1 mL of assay buffer to a 250 mM stock) were sufficiently mixed and dissolved in Fluo-4 NW dye mix. The medium of cells inoculated on the previous day was removed, the dissolved Fluo-4 NW dye mix was added in an amount of 90 μL/well, and a reaction was caused in the dark at 37° C. for 45 minutes. The cells after the reaction and chips for addition of the compound were set in Flexstation, and variation in fluorescence intensity over time after addition of the compound was measured [amount of added compound=10 μL (final concentration: $10^{-5}$ M to $10^{-12}$ M), excitation wavelength: 485 nm, measured wavelength: 525 nm, 1.5 sec×54 read]. A value was calculated by subtracting a base value during addition of DMSO from the maximum value of relative fluorescence unit, and analyzed. All the measurement data were analyzed with Prism 4 that was a data analysis tool. As an $EC_{50}$ value, a molar concentration that resulted in 50% maximum activation was calculated. The $EC_{50}$ values of the resultant test compounds are shown in Table I.

TABLE I

| Compound to be tested | Efficacy $EC_{50}$ (nM) |
|---|---|
| Example 1-1 | 0.25 |
| Example 1-5 | 12 |
| Example 1-6 | 10 |
| Example 1-7 | 5.2 |
| Example 1-8 | 3.78 |
| Example 1-9 | 2.3 |
| Example 1-10 | 0.29 |
| Example 1-11 | 0.11 |
| Example 2-1 Isomer A | 0.54 |
| Example 3-1 Isomer A | 0.62 |
| Example 5-1 | 14 |
| Example 5-4 | 2.6 |
| Example 6-1 | 5.6 |
| Example 7-1 | 0.05 |
| Example 7-2 | 0.25 |
| Example 7-3 | 0.6 |
| Example 7-4 | 0.36 |
| Example 7-5 | 2.5 |
| Example 7-6 | 0.97 |
| Example 7-7 | 0.02 |
| Example 8-1 | 0.03 |
| Example 9-1 | 0.03 |
| Example 10-1 | 0.29 |

As seen from Table I, the compounds (I) of the present invention or pharmacologically acceptable salts thereof show a superior FPRL1 agonist effect.

Test Example 2

Effect of lipopolysaccharide induction on neutrophilic infiltration in mouse lung A compound to be tested was orally administered to a mouse (BALB/c, male), and after 30 minutes, the mouse was placed in a plastic container. Lipopolysaccharide (0.3 mg/mL) dissolved in physiological saline was aerosolized with an ultrasonic wave nebulizer (NE-U17, OMRON Corporation), and exposed to the mouse for 10 minutes. After 5 hours, the anesthetized mouse was sacrificed by exsanguination. A cannula was inserted in the respiratory tract and bronchoalveolar lavage (BAL) with 1 mL of 0.85% NaCl liquid containing 0.4% sodium citrate was carried out. This operation was repeated 3 times, to obtain a BAL fluid. The BAL fluid was centrifuged at 4° C. and ×200 g for 5 minutes, and the pellet was suspended in a physiological saline containing 0.1% BSA. The number of white blood cells was counted using Turks solution with a microscope, and the total white blood cell count was calculated. The white blood cells were fixed on a glass slide using Cytospin 3 (Thermo BioAnalysis Japan K. K.). The cells were stained with Diff-Quik (SYSMEX INTERNATIONAL REAGENTS CO., LTD.), and the number thereof was counted with a microscope, and the neutrophil ratio was calculated. The neutrophil ratio was multiplied by the total white blood cell count to calculate the total neutrophil count. An effect of the compound to be tested represents a percentage (%) of suppression ratio relative to the neutrophil count in a control. The suppression ratios of the resultant test compounds are shown in Table II.

TABLE II

| Compound to be tested | Suppression Ratio (%) | Dose (mg/kg) |
|---|---|---|
| Example 2-1 Isomer A | 82 | 3 |
| Example 3-1 Isomer A | 80 | 3 |
| Example 7-7 | 97 | 1 |

As seen from Table II, the compounds (I) of the present invention or pharmacologically acceptable salts thereof had a superior action of suppressing neutrophil infiltration.

INDUSTRIAL APPLICABILITY

The compound of the present invention has a superior action of suppressing neutrophil infiltration due to a superior FPRL1 agonist effect, and therefore is useful as a therapeutic or prophylactic agent for inflammatory disease, chronic airway diseases, cancers, septicemia, allergic symptoms, HIV retrovirus infection, circulatory disorders, neuroinflammation, nervous disorders, pains, prion diseases, amyloidosis, immune disorders and the like.

SEQUENCE LISTING FREE TEXT

<Sequence Listing 1>

SEQ ID NO: 1 is a sequence of a forward primer used for amplification of DNA of human FPRL1 (SEQ ID NO: 3), and is supplemented with a Hind III recognition site.

<Sequence Listing 2>

SEQ ID NO: 2 is a sequence of a reverse primer used for amplification of DNA of human FPRL1 (SEQ ID NO: 3), and is supplemented with an XhoI recognition site.

<Sequence Listing 3>

SEQ ID NO: 3 is an open reading frame (ORF) of human FPRL1, and is a DNA sequence of a site translated into an amino acid.

<Sequence Listing 4>

SEQ ID NO: 4 is a sequence of a forward primer used for amplification of DNA of human Gα15 (SEQ ID NO: 6), and is supplemented with a Hind III recognition site.

<Sequence Listing 5>

SEQ ID NO: 5 is a sequence of a reverse primer used for amplification of DNA of human Gα15 (SEQ ID NO: 6), and is supplemented with an XhoI recognition site.

<Sequence Listing 6>

SEQ ID NO: 6 is an open reading frame (ORF) of human Gα15, and is a DNA sequence of a site translated into an amino acid.

The invention claimed is:
1. A compound represented by the formula (I) or a pharmacologically acceptable salt thereof:

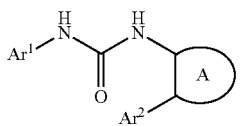

wherein,
in the formula (I), $Ar^1$ is a phenyl group optionally having substituent(S), a monocyclic aromatic heterocyclyl group optionally having substituent(S);
$Ar^2$ is a phenyl group optionally having substituent(S), provided that when A is A1, the phenyl group whose substituent(s) is only a halogen atom is excluded, a monocyclic aromatic heterocyclyl group optionally having substituent(S), or a bicyclic aromatic heterocyclyl group having 9 or 10 atoms and optionally having substituent(s);
A is a group selected from the group consisting of the following A1), A2), A3), A4), and A5):

A1)

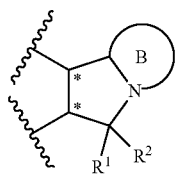

A2)

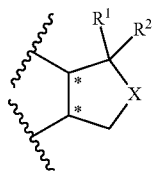

A3)

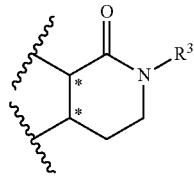

A4)

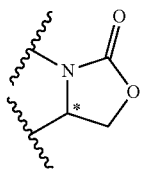

A5)

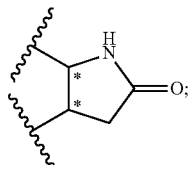

wherein $R^1$ and $R^2$ are independently a hydrogen atom or a $C_1$ to $C_6$ alkyl group optionally having substituent(S), or $R^1$ and $R^2$ together form a $C_2$ to $C_6$ alkylene group;
$R^3$ is a hydrogen atom or a $C_1$ to $C_6$ alkyl group optionally having substituent(S);
X is an oxygen atom, a sulfur atom, or $SO_2$;
B is a heterocyclyl group optionally having substituent (S); and
each carbon atom marked with an asterisk is an asymmetric carbon atom.

2. The compound according to claim 1 or a pharmacologically acceptable salt thereof, wherein
in the formula (I), A is a group selected from the group consisting of the following A1a), A1b), and A1c):

A1a)

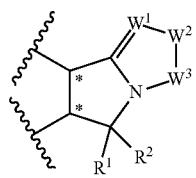

A1b)

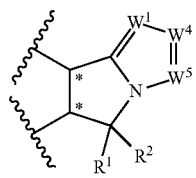

A1c)

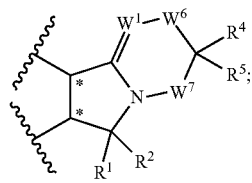

wherein $W^1$ is C—$R^6$ or a nitrogen atom;
$W^2$ is $CR^7R^8$ or N—$R^9$;
$W^3$ is $CR^{10}R^{11}$ or C=O;
$W^4$ is C—$R^{12}$ or a nitrogen atom;
$W^5$ is C—$R^{13}$ or a nitrogen atom;
$W^6$ is $CR^{14}R^{15}$, an oxygen atom, or C=O;
$W^7$ is $CR^{16}R^{17}$ or C=O;
$R^4$, $R^5$, $R^7$, $R^8$, $R^{10}$, $R^{11}$, $R^{14}$, $R^{15}$, $R^{16}$, and $R^{17}$ are independently a hydrogen atom or a $C_1$ to $C_6$ alkyl group optionally having substituent(S), or $R^4$ and $R^5$, $R^7$ and $R^8$, $R^{10}$ and $R^{11}$, $R^{14}$ and $R^{15}$, or $R^{16}$ and $R^{17}$ can together form a $C_3$ to $C_6$ cycloalkyl group or a 3- to 10-membered heterocycloalkyl group; and
$R^6$, $R^9$, $R^{12}$, and $R^{13}$ are independently a hydrogen atom, a halogen atom, a cyano group, a hydroxy group, a $C_1$ to $C_6$ alkyl group optionally having substituent(S), a $C_1$ to $C_6$ alkoxy group optionally having substituent(S), a $C_1$ to $C_6$ alkoxycarbonyl group optionally having substituent(S), a $C_1$ to $C_6$ acyl group optionally having substituent(S), a $C_1$ to $C_6$ alkylsulfanyl group optionally having substituent(S), a $C_1$ to $C_6$ alkylsulfinyl group optionally having substituent(S), a $C_1$ to $C_6$ alkylsulfonyl group optionally having substituent(S), a heterocyclyl group optionally having substituent(S), —$CONR^{18}R^{19}$, or —$NR^{18}R^{19}$, wherein when $R^6$, $R^9$, $R^{12}$, and/or $R^{13}$ are —$CONR^{18}R^{19}$ or —$NR^{18}R^{19}$, $R^{18}$ is a hydrogen atom, a $C_1$ to $C_6$ alkyl group optionally having substituent(S), a $C_1$ to $C_6$ acyl group optionally having substituent(S), or a $C_1$ to $C_6$ alkylsulfonyl group optionally having substituent(S), and $R^{19}$ is a hydrogen atom or a $C_1$ to $C_6$ alkyl group optionally having substituent(S), or $R^{18}$ and $R^{19}$ together form 3- to 10-membered heterocycloalkyl group.

3. The compound according to claim 1 or a pharmacologically acceptable salt thereof, wherein
in the formula (I), A is a group selected from the groups consisting of the following A1ba), A1bb), A1bc), A1ca), A1cb), A1cc), A1cd), A2), A3), A4), and A5):

A1ba)
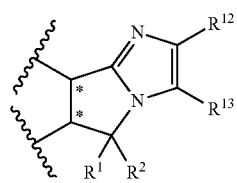

A1bb)
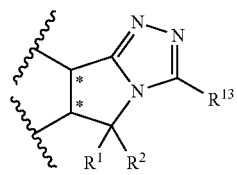

A1bc)
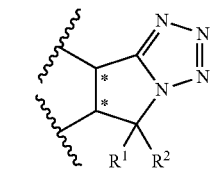

A1ca)
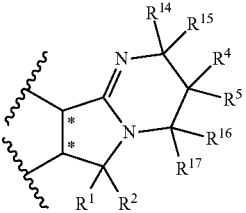

A1cb)
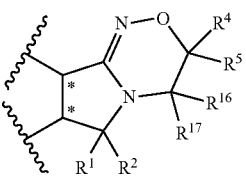

A1cc)
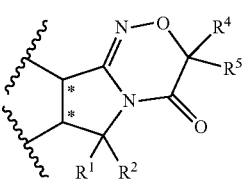

A1cd)
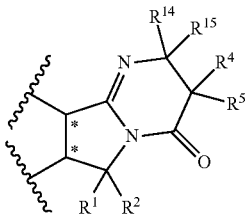

A2)
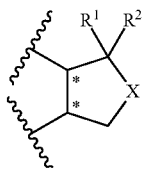

A3)
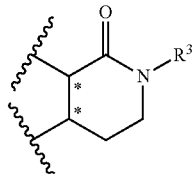

A4)
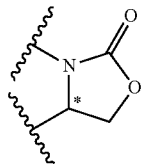

A5)
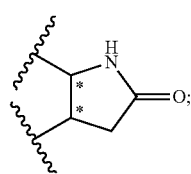

wherein $R^1$ and $R^2$ are independently a hydrogen atom or a $C_1$ to $C_3$ alkyl group;
$R^3$ is a hydrogen atom or a $C_1$ to $C_3$ alkyl group;
$R^4$, $R^5$, $R^{14}$, $R^{15}$, $R^{16}$, and $R^{17}$ are independently a hydrogen atom or a $C_1$ to $C_6$ alkyl group, or $R^4$ and $R^5$, $R^{14}$ and $R^{15}$, or $R^{16}$ and $R^{17}$ can together form a $C_3$ to $C_6$ cycloalkyl group or a 3- to 10-membered heterocycloalkyl group;
$R^{12}$ and $R^{13}$ are independently a hydrogen atom, a halogen atom, a cyano group, a hydroxy group, a $C_1$ to $C_3$ alkyl group, a $C_1$ to $C_6$ alkoxy group, a $C_1$ to $C_6$ alkoxycarbonyl group, a $C_1$ to $C_6$ acyl group, a $C_1$ to $C_6$ alkylsulfanyl group, a $C_1$ to $C_6$ alkylsulfinyl group, a $C_1$ to $C_6$ alkylsulfonyl group, —$CONR^{18}R^{19}$, or —$NR^{18}R^{19}$, wherein when $R^{12}$ and/or $R^{13}$ are —$CONR^{18}R^{19}$ or —$NR^{18}R^{19}$, $R^{18}$ is a hydrogen atom, a $C_1$ to $C_6$ alkyl group, a $C_1$ to $C_6$ acyl group, or a $C_1$ to $C_6$ alkylsulfonyl group, and $R^{19}$ is a hydrogen atom or a $C_1$ to $C_6$ alkyl group, or $R^{18}$ and $R^{19}$ together form 3- to 10-membered heterocycloalkyl group; and
X is an oxygen atom or $SO_2$.

4. The compound according to claim 1 or a pharmacologically acceptable salt thereof, wherein in the formula (I), $Ar^2$ is a group selected from the group consisting of the following B1), B2), B3), and B4):

B1)
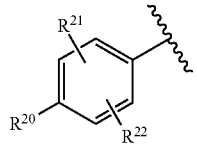

B2)
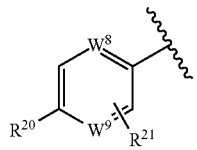

B3)
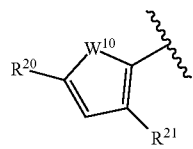

B4)
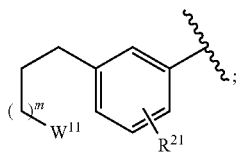

wherein one of $W^8$ and $W^9$ is a nitrogen atom, and the other one is CH or a nitrogen atom;
$W^{10}$ is an oxygen atom, a sulfur atom, or $N-R^{22}$;
$W^{11}$ is C=O, $CH_2$, $CF_2$, CHOH, $N-R^{23}$, an oxygen atom, or a sulfur atom;
$R^{20}$ is a hydrogen atom, a halogen atom, a hydroxy group, a cyano group, a $C_1$ to $C_6$ alkyl group optionally having substituent(S), a $C_1$ to $C_6$ alkoxy group optionally having substituent(S), a halo-$C_1$ to $C_6$ alkoxy group having substituent(S), a $C_1$ to $C_6$ acyl group optionally having substituent(S), a $C_1$ to $C_6$ alkylsulfanyl group optionally having substituent(S), a $C_1$ to $C_6$ alkylsulfinyl group optionally having substituent(S), a $C_1$ to $C_6$ alkylsulfonyl group optionally having substituent(S), a heterocyclyl group optionally having substituent(S), $-CONR^{18}R^{19}$, or $-NR^{18}R^{19}$, wherein when $R^{20}$ is $-CONR^{18}R^{19}$ or $-NR^{18}R^{19}$, $R^{18}$ is a hydrogen atom, a $C_1$ to $C_6$ alkyl group optionally having substituent(S), a $C_1$ to $C_6$ acyl group optionally having substituent(S), or a $C_1$ to $C_6$ alkylsulfonyl group optionally having substituent(S), and $R^{19}$ is a hydrogen atom or a $C_1$ to $C_6$ alkyl group optionally having substituent(S), or $R^{18}$ and $R^{19}$ together form 3- to 10-membered heterocycloalkyl group;
$R^{21}$ is a hydrogen atom, a halogen atom, a hydroxy group, cyano group, a $C_1$ to $C_6$ alkyl group optionally having substituent(S), or a $C_1$ to $C_6$ alkoxy group optionally having substituent(S);
$R^{22}$ is a hydrogen atom, a halogen atom, or a $C_1$ to $C_6$ alkyl group optionally having substituent(S);
m is 0 or 1; and
provided that when $Ar^2$ is B1), $R^{20}$, $R^{21}$, and $R^{22}$ are not a combination of a hydrogen atom and a halogen atom.

5. The compound according to claim 1 or a pharmacologically acceptable salt thereof, wherein
in the formula (I), $Ar^1$ is a group selected from the group consisting of the following C1), C2), C3), and C4):

C1)
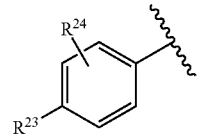

C2)
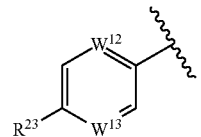

C3)
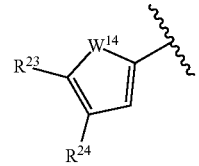

wherein one of $W^{12}$ and $W^{13}$ is a nitrogen atom, and the other one is CH or a nitrogen atom;
$W^{14}$ is an oxygen atom, a sulfur atom or $N-R^{22}$;
$R^{23}$ is a hydrogen atom, a halogen atom, a cyano group, a $C_1$ to $C_6$ alkyl group optionally having substituent(S), a $C_1$ to $C_6$ alkoxy group optionally having substituent (S), a $C_3$ to $C_6$ cycloalkyl group optionally having substituent(S), a $C_1$ to $C_6$ acyl group optionally having substituent(S), a $C_2$ to $C_6$ alkenyl group optionally having substituent(S), an alkynyl group optionally having substituent(S), a $C_1$ to $C_6$ alkoxycarbonyl group optionally having substituent(S), a $C_1$ to $C_6$ alkylsulfanyl group optionally having substituent(S), a $C_1$ to $C_6$ alkylsulfinyl group optionally having substituent(S), a $C_1$ to $C_6$ alkylsulfonyl group optionally having substituent(S), an aryloxy group optionally having substituent(S), a heterocyclyl group optionally having substituent(S), $-CONR^{18}R^{19}$, or $-NR^{18}R^{19}$, wherein when $R^{23}$ is $-CONR^{18}R^{19}$ or $-NR^{18}R^{19}$, $R^{18}$ is a hydrogen atom, a $C_1$ to $C_6$ alkyl group optionally having substituent(S), a $C_1$ to $C_6$ acyl group optionally having substituent(S), or a $C_1$ to $C_6$ alkylsulfonyl group optionally having substituent(S), and $R^{19}$ is a hydrogen atom or a $C_1$ to $C_6$ alkyl group optionally having substituent(S), or $R^{18}$ and $R^{19}$ together form 3- to 10-membered heterocycloalkyl group; and
$R^{24}$ is a hydrogen atom, a halogen atom, hydroxy group, or a $C_1$ to $C_6$ alkyl group.

6. The compound according to claim 1 or a pharmacologically acceptable salt thereof, wherein
in the formula (I), $Ar^2$ is a group selected from the group consisting of the following B1a), B3a), and B4a):

B1a)

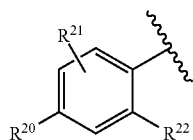

B3a)

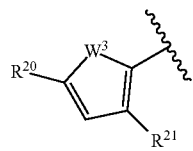

B4a)

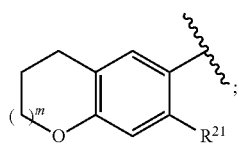

wherein $R^{20}$ is a fluorine atom, a chlorine atom, a cyano group, a $C_1$ to $C_6$ alkyl group, a $C_1$ to $C_6$ alkoxy group, a halo-$C_1$ to $C_6$ alkoxy group, a $C_1$ to $C_6$ alkylsulfanyl group, a $C_1$ to $C_6$ alkylsulfinyl group, —$CONR^{18}R^{19}$, or —$NR^{18}R^{19}$, wherein when $R^{20}$ is —$CONR^{18}R^{19}$ or —$NR^{18}R^{19}$, $R^{18}$ is a hydrogen atom, a $C_1$ to $C_6$ alkyl group, a $C_1$ to $C_6$ acyl group, or a $C_1$ to $C_6$ alkylsulfonyl group, and $R^{19}$ is a hydrogen atom or a $C_1$ to $C_6$ alkyl group, or $R^{18}$ and $R^{19}$ together form 3- to 10-membered heterocycloalkyl group;
$R^{21}$ is a hydrogen atom or a halogen atom;
$R^{22}$ is a hydrogen atom or a halogen atom;
m is 0 or 1; and
provided that when $Ar^2$ is B1a), $R^{20}$, $R^{21}$, and $R^{22}$ are not a combination of a hydrogen atom and a halogen atom.

7. The compound according to claim 1 or a pharmacologically acceptable salt thereof, wherein
in the formula (I), $Ar^1$ is C1):

C1)

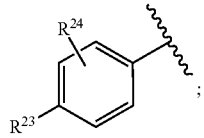

wherein $R^{23}$ is a hydrogen atom, a halogen atom, a cyano group, a trifluoromethyl group, or a $C_1$ to $C_3$ alkyl group; and
$R^{24}$ is a hydrogen atom, a halogen atom, or a hydroxy group.

8. The compound according to claim 1 or a pharmacologically acceptable salt thereof, wherein
in the formula (I), $Ar^2$ is B1aa):

B1aa)

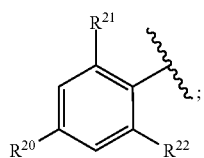

wherein $R^{20}$ is a cyano group, an ethyl group, or a $C_1$ to $C_3$ alkoxy group;
$R^{21}$ is a hydrogen atom, a fluorine atom, or a chlorine atom; and
$R^{22}$ is a hydrogen atom, a fluorine atom, or a chlorine atom.

9. The compound according to claim 1 or a pharmacologically acceptable salt thereof, wherein
the compound represented by the formula (I) is
(±)-cis-1-(4-chlorophenyl)-3-[4-(4-methoxyphenyl)tetrahydrofuran-3-yl]urea,
(±)-cis-1-(3-fluorophenyl)-3-[4-(4-methoxyphenyl)tetrahydrofuran-3-yl]urea,
(±)-cis-1-(2-fluorophenyl)-3-[4-(4-methoxyphenyl)tetrahydrofuran-3-yl]urea,
(±)-cis-1-(2,4-difluorophenyl)-3-[4-(4-methoxyphenyl)tetrahydrofuran-3-yl]urea,
(±)-cis-1-(3,4-difluorophenyl)-3-[4-(4-methoxyphenyl)tetrahydrofuran-3-yl]urea,
(±)-cis-1-(4-cyanophenyl)-3-[4-(4-methoxyphenyl)tetrahydrofuran-3-yl]urea,
(±)-cis-1-(5-chlorothiophen-2-yl)-3-[4-(4-methoxyphenyl)tetrahydrofuran-3-yl]urea,
(±)-cis-1-[4-(2,6-difluoro-4-methoxyphenyl)tetrahydrofuran-3-yl]-3-(4-fluorophenyl)urea,
(±)-trans-1-(4-chlorophenyl)-3-[4-(4-methoxyphenyl)tetrahydrofuran-3-yl]urea,
(±)-1-(4-chlorophenyl)-3-[4-(4-methoxyphenyl)-1,1-dioxidotetrahydrothiophen-3-yl]urea,
(±)-trans-1-(4-chlorophenyl)-3-[4-(4-methoxyphenyl)-2-oxopiperidin-3-yl]urea,
(±)-cis-1-(4-chlorophenyl)-3-[4-(4-methoxyphenyl)tetrahydrofuran-3-yl]urea,
(±)-cis-1-(4-fluorophenyl)-3-[4-(4-methoxyphenyl)tetrahydrofuran-3-yl]urea,
(±)-cis-1-(4-fluorophenyl)3-[4-(4-methoxyphenyl)-2,2-dimethyltetrahydrofuran-3-yl]urea,
(±)-cis-1-[4-(4-chlorophenyl)tetrahydrofuran-3-yl]-3-(4-fluorophenyl)urea,
(±)-cis-1-[4-(4-fluorophenyl)tetrahydrofuran-3-yl]-3-(4-fluorophenyl)urea,
(±)-cis-1-[4-(4-cyanophenyl)tetrahydrofuran-3-yl]-3-(4-fluorophenyl)urea,
(±)-1-(4-chlorophenyl)-3-[4-(4-methoxyphenyl)-2-oxoxazolidin-3-yl]urea,
(±)-trans-1-(4-fluorophenyl)-3-[3-(4-methoxyphenyl)-5-oxopyrrolidin-2-yl]urea,
(−)-1-[(6R*, 7S*)-6-(2,6-difluoro-4-methoxyphenyl)-3-methyl-6,7-dihydro-5H-pyrrolo[2,1-c][1,2,4]triazol-7-yl]-3-(4-fluorophenyl)urea,
(−)-1-[(6R*, 7S*)-6-(2,6-difluoro-4-methoxyphenyl)-6,7-dihydro-5H-pyrrolo[1,2-a]imidazol-7-yl]-3-(4-fluorophenyl)urea,
(−)-1-(4-fluorophenyl)-3-[(6R*, 7S*)-6-(4-methoxyphenyl)-6,7-dihydro-5H-pyrrolo[1,2-d]tetrazol-7-yl]urea,
(−)-1-[(6R*, 7S*)-6-(2,6-difluoro-4-methoxyphenyl)-6,7-dihydro-5H-pyrrolo[1,2-d]tetrazol-7-yl]-3-(4-fluorophenyl)urea,
(−)-1-[(6R*, 7S*)-6-(6-fluoro-2,3-dihydrobenzofuran-5-yl)-6,7-dihydro-5H-pyrrolo[1,2-d]tetrazol-7-yl]-3-(4-fluorophenyl)urea,
(−)-1-[(7R*,8S*)-7-(2,6-difluoro-4-methoxyphenyl)-2,3,4,6,7,8-hexahydropyrrolo[1,2-a]pyrimidin-8-yl]-3-(4-fluorophenyl)urea,
1-[(7R*,8S*)-7-(2,6-difluoro-4-methoxyphenyl)-4,6,7,8-tetrahydro-3H-pyrrolo[2,1-c][1,2,4]oxadiazin-8-yl]-3-(4-fluorophenyl)urea, (−)-1-[(7R*,8S*)-7-(2,6-difluoro-4-methoxyphenyl)-4-oxo-4,6,7,8-tetrahydro-3H-pyrrolo[2,1-c][1,2,4]oxadiazin-8-yl]-3-(4-fluorophenyl)urea, (−)-1-[(7R*,8S*)-7-(2,6-difluoro-4-methoxyphenyl)-4-oxo-2,3,4,6,7,8-hexahydropyrrolo[1,2-a]pyrimidin-8-yl]-3-(4-fluorophenyl)urea, or 1-(4-fluorophenyl)-3-[(7R*,8S*)-7-(4-methoxyphenyl)-4-oxo-4,6,7,8-tetrahydro-3H-pyrrolo[2,1-c][1,2,4]oxadiazin-8-yl]urea.

10. A pharmaceutical comprising, as an active ingredient, the compound according to claim 1 or a pharmacologically acceptable salt thereof.

11. An FPRL1 agonist comprising, as an active ingredient, the compound according to claim 1 or a pharmacologically acceptable salt thereof.

12. A method of treating septicemia, allergic symptoms, myocardial infarction, and immune disorders in a patient in need thereof, comprising administering the compound according to claim 1 or a pharmacologically acceptable salt thereof to the patient.

13. A pharmaceutical composition containing the compound according to claim 1 or a pharmacologically acceptable salt thereof and a pharmaceutically acceptable carrier.

\* \* \* \* \*